United States Patent
Chambers et al.

(10) Patent No.: US 7,592,456 B2
(45) Date of Patent: Sep. 22, 2009

(54) ARYLSULFONYLNAPHTHALENE DERIVATIVES AS 5HT$_{2A}$ ANTAGONISTS

(75) Inventors: Mark Stuart Chambers, Puckeridge (GB); Neil Roy Curtis, Buntingford (GB); Emanuela Gancia, Royston (GB); Myra Gilligan, Hoddesdon (GB); Alexander Charles Humphries, Stevenage (GB); Tamara Ladduwahetty, London (GB); Robert James Maxey, Amersham (GB); Kevin John Merchant, Ware (GB)

(73) Assignee: Merck Sharp & Dohme Limited, Hoddesdon, Hertfordshire (GB)

( * ) Notice: Subject to any disclaimer, the term of this patent is extended or adjusted under 35 U.S.C. 154(b) by 30 days.

(21) Appl. No.: 11/791,195

(22) PCT Filed: Nov. 28, 2005

(86) PCT No.: PCT/GB2005/050215

§ 371 (c)(1),
(2), (4) Date: May 18, 2007

(87) PCT Pub. No.: WO2006/059149

PCT Pub. Date: Jun. 8, 2006

(65) Prior Publication Data

US 2007/0281952 A1 Dec. 6, 2007

(30) Foreign Application Priority Data

Dec. 1, 2004 (GB) .................. 0426313.3

(51) Int. Cl.
*C07D 215/00* (2006.01)
*C07D 401/02* (2006.01)
*C07D 401/00* (2006.01)
*C07D 401/10* (2006.01)
*C07C 305/00* (2006.01)

(52) U.S. Cl. .................. 546/153; 546/157; 546/18; 558/37

(58) Field of Classification Search ............... 514/263.1, 514/256, 277, 299, 363, 383, 396, 403, 709; 544/128, 363, 242, 264; 546/7, 112, 134, 546/154, 167, 172, 177, 178; 568/328, 28; 548/240, 262.2, 300.1, 356.1

See application file for complete search history.

(56) References Cited

U.S. PATENT DOCUMENTS

| 4,128,552 A | 12/1978 | Wise et al. |
| 4,218,455 A | 8/1980 | Wise et al. |
| 4,812,461 A | 3/1989 | Antoku et al. |
| 4,948,799 A | 8/1990 | Antoku et al. |
| 4,977,165 A | 12/1990 | Oinuma et al. |
| 5,082,850 A | 1/1992 | Oinuma et al. |
| 5,162,347 A | 11/1992 | Oinuma et al. |
| 5,246,946 A | 9/1993 | Oinuma et al. |
| 5,753,679 A | 5/1998 | Riemer |
| 6,559,166 B1 | 5/2003 | Blurton et al. |
| 6,777,430 B2 | 8/2004 | Blurton et al. |
| 6,852,718 B2 | 2/2005 | Burkamp et al. |
| 7,094,777 B2 | 8/2006 | Chambers et al. |
| 2005/0124628 A1* | 6/2005 | Ahmend et al. .......... 514/253.07 |
| 2006/0211735 A1 | 9/2006 | Gilligan et al. |

FOREIGN PATENT DOCUMENTS

| EP | 0330826 | | 1/1989 |
| WO | WO03076422 | * | 9/2003 |
| WO | WO 2004/101518 | | 11/2004 |

OTHER PUBLICATIONS

S. R. Fletcher et al., "4-(Phenylsulfonyl)Piperidines: Novel, Selective, and Bioavailable 5-HT2A Receptor Antagonists", J. Med. Chem., 2002, vol. 45, pp. 492-503.

* cited by examiner

*Primary Examiner*—Brian-Yong S Kwon
*Assistant Examiner*—Bong-Sook Baek
(74) *Attorney, Agent, or Firm*—J. Eric Thies; William Krovatin

(57) ABSTRACT

Compounds of formula (I) are potent and selective 5-HT$_{2A}$ antagonists, useful in treatment of a variety of adverse conditions of the CNS.

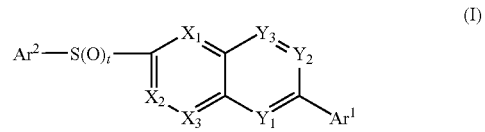

10 Claims, No Drawings

ARYLSULFONYLNAPHTHALENE DERIVATIVES AS 5HT$_{2A}$ ANTAGONISTS

CROSS REFERENCE TO RELATED APPLICATIONS

This application is a U.S. National Phase application under 35 U.S.C. §371 of PCT Application No. PCT/GB2005/050215, filed Nov. 28, 2005, which claims priority under 35 U.S.C. §119 from GB Application No. 0426313.3, filed Dec. 1, 2004.

The present invention relates to a class of sulphonyl derivatives which act on serotonin receptors (also known as 5-hydroxytryptamine or 5-HT receptors). More particularly, the invention concerns arylsulphonylnaphthalenes and derivatives thereof. These compounds are potent and selective antagonists of the human 5-HT$_{2A}$ receptor and are therefore useful as pharmaceutical agents, especially in the treatment and/or prevention of adverse conditions of the central nervous system, including sleep disorders such as insomnia, psychotic disorders such as schizophrenia and psychiatric disorders such as anxiety.

Compounds of the invention typically display more effective binding to the human 5-HT$_{2A}$ receptor than to other human receptors such as D$_2$, 5HT$_{2C}$ and IKr receptors. They can therefore be expected to manifest fewer side-effects than compounds which do not discriminate in their binding affinity between such receptors. In particular these compounds have lower effects on the IKr receptors and there is a separation of the desired effect from side effects such as cardiac effects.

By virtue of their potent human 5-HT$_{2A}$ receptor antagonist activity, the compounds of the present invention are effective in the treatment of neurological conditions including sleep disorders such as insomnia, psychotic disorders such as schizophrenia, and also depression, anxiety, panic disorder, obsessive-compulsive disorder, pain, eating disorders such as anorexia nervosa, and dependency or acute toxicity associated with narcotic agents such as LSD or MDMA; and moreover are beneficial in controlling the extrapyramidal symptoms associated with the administration of neuroleptic agents. They may further be effective in the lowering of intraocular pressure (and hence in treatment of glaucoma), and may also be effective in treating menopausal symptoms, in particular hot flushes (see Waldinger et al, *Maturitas*, 2000, 36, 165-8).

Various classes of compounds containing inter alia a sulphonyl moiety are described in WO 2005/047246, WO 2004/101518, WO 01/74797, WO 00/43362, WO 96/35666, EP-A-0261688, EP-0304888, and U.S. Pat. Nos. 4,218,455 and 4,128,552, DE-A-3901735 and Fletcher et al, *J. Med. Chem.*, 2002, 45, 492-503. None of these publications, however, discloses or suggests the particular class of compounds provided by the present invention.

The compounds according to the present invention are potent and selective 5-HT$_{2A}$ receptor antagonists, suitably having a human 5-HT$_{2A}$ receptor binding affinity (K$_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor and/or the human IKr and/or 5-HT$_{2C}$ receptors. Preferred compounds show selectivities of at least 100-fold relative to the human 5-HT$_{2C}$ receptor.

In accordance with the invention there is provided a compound of formula I:

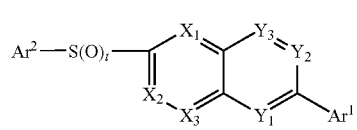

or a pharmaceutically acceptable salt or hydrate thereof, wherein:

t is 1 or 2;

X1, X2, X3, Y1, Y2 and Y3 each represents CH or N, provided that not more than one of X1, X2 and X3 represents N and not more than one of Y1, Y2 and Y3 represents N;

Ar$^1$ represents phenyl or 6-membered heteroaryl comprising up to 2 ring nitrogen atoms, said phenyl or heteroaryl bearing 0 to 3 substituents selected from halogen, CN, CF$_3$, OCF$_3$, C$_{1-6}$alkyl, OH, C$_{1-6}$alkoxy or hydroxyC$_{1-6}$alkyl;

Ar$^2$ represents phenyl or 5- or 6-membered heteroaryl in which up to 3 ring atoms are selected from N, O and S, said phenyl or heteroaryl bearing 0 to 3 substituents selected from halogen, CN, nitro, R$^a$, OR$^a$, SR$^a$, SOR$^a$, SO$_2$R$^a$, SO$_2$NR$^a$R$^b$, (CH$_2$)$_x$NR$^a$R$^b$, (CH$_2$)$_x$NR$^a$COR$^b$, (CH$_2$)$_x$NR$^a$CO$_2$R$^b$, (CH$_2$)$_x$NR$^a$CONR$^a$R$^b$, (CH$_2$)$_x$NR$^a$SOR$^b$, (CH$_2$)$_x$NR$^a$SO$_2$R$^b$, (CH$_2$)$_x$NR$^a$SO$_2$NR$^a$R$^b$, (CH$_2$)$_x$COR$^a$, (CH$_2$)$_x$CO$_2$R$^a$, (CH$_2$)$_x$CONR$^a$R$^b$, N=CHN(CH$_3$)$_2$, and (CH$_2$)$_x$CR$^a$=NOR$^b$, where x is 0 or 1, or said phenyl or heteroaryl may be substituted with (CH$_2$)$_x$Ar$^3$, COAr$^3$ or CH(OH)Ar$^3$ where Ar$^3$ represents a five- or six-membered heteroaromatic ring optionally bearing up to 2 substituents selected from halogen, CN, CF$_3$, OH, C$_{1-6}$alkyl, C$_{1-6}$alkoxy, C$_{1-6}$alkylthio, amino, C$_{1-6}$alkylamino and di(C$_{1-6}$)alkylamino;

R$^a$ and R$^b$ independently represent H or a hydrocarbon group of up to 7 carbon atoms which is optionally substituted with up to 3 halogen atoms or with up to 2 substituents selected from CN, OH, C$_{1-4}$alkoxy, C$_{1-4}$alkylthio, amino, C$_{1-4}$alkylamino and di(C$_{1-4}$)alkylamino; or R$^a$ and R$^b$, when linked through a nitrogen atom, together represent the residue of a heterocyclic ring of 4, 5 or 6 members, optionally bearing up to 3 substituents selected from halogen, CN, CF$_3$, oxo, OH, C$_{1-4}$alkyl and C$_{1-4}$alkoxy; or two R$^a$ groups, when attached to adjacent carbon atoms of Ar$^2$, may complete a fused ring of 5 or 6 members, 0-3 of which are selected from N, O and S while the remainder are carbon, said ring optionally bearing up to 3 substituents selected from halogen CN, CF$_3$, oxo, OH, C$_{1-4}$alkyl and C$_{1-4}$alkoxy;

and wherein any nitrogen atom forming part of a heteroaromatic ring may be in the form of the N-oxide.

In a particular embodiment, Ar$^2$ represents phenyl or 6-membered heteroaryl comprising up to 2 ring nitrogen atoms, said phenyl or heteroaryl bearing 0 to 3 substituents selected from halogen, CN, nitro, R$^a$, OR$^a$, SR$^a$, SOR$^a$, SO$_2$R$^a$, SO$_2$NR$^a$R$^b$, NR$^a$R$^b$, CH$_2$NR$^a$R$^b$, NR$^a$COR$^b$, NR$^a$CO$_2$R$^b$, NR$^a$CO$_2$NR$^a$R$^b$, NR$^a$SO$_2$NR$^a$R$^b$, COR$^a$, CO$_2$R$^a$, CONR$^a$R$^b$, CH=NOR$^a$ or a five- or six-membered heteroaromatic ring optionally bearing up to 2 substituents selected from halogen, CN, CF$_3$, C$_{1-6}$alkyl, C$_{1-6}$alkoxy, C$_{1-6}$alkylthio, amino, C$_{1-6}$alkylamino and di(C$_{1-6}$)alkylamino; and R$^a$ and R$^b$ independently represent H or a hydrocarbon group of up to 7 carbon atoms which is optionally substituted with up to 3 halogen atoms or with CN, OH, C$_{1-4}$alkoxy, C$_{1-4}$alkylthio, amino, C$_{1-4}$alkylamino or di(C$_{1-4}$)alkylamino; or R$^a$ and R$^b$, when linked through a nitrogen atom, together represent the residue of a heterocyclic ring of 4, 5 or 6 members, optionally bearing up to 3 substituents selected from halogen, CN, $CF_3$, oxo, OH, $C_{1-4}$alkyl and $C_{1-4}$alkoxy.

Where a variable occurs more than once in formula I or in a substituent group thereof, the individual occurrences of that variable are independent of each other, unless otherwise specified.

As used herein, the expression "hydrocarbon group" refers to groups consisting solely of carbon and hydrogen atoms. Such groups may comprise linear, branched or cyclic structures, singly or in any combination consistent with the indicated maximum number of carbon atoms, and may be saturated or unsaturated, including aromatic when the indicated maximum number of carbon atoms so permits unless otherwise indicated.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl" and "$C_{1-6}$alkoxy" are to be construed in an analogous manner. Most suitably, the number of carbon atoms in such groups is not more than 6.

The term "halogen" as used herein includes fluorine, chlorine, bromine and iodine, of which fluorine and chlorine are preferred and fluorine particularly preferred.

The expression "$C_{3-6}$cycloalkyl" as used herein refers to nonaromatic monocyclic hydrocarbon ring systems comprising from 3 to 6 ring atoms. Examples include cyclopropyl, cyclobutyl, cyclopentyl, cyclohexyl and cyclohexenyl.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

When the compounds according to the invention have one or more asymmetric centres, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, t is 1 or 2. In a particular embodiment t is 2.

In formula I, X1, X2, X3, Y1, Y2 and Y3 each represents CH or N, provided that not more than one of X1, X2 and X3 represents N and not more than one of Y1, Y2 and Y3 represents N. In a particular embodiment, not more than one of X1, X2, X3, Y1, Y2 and Y3 represents N. Within this embodiment, preferably X1 or Y1 represents N, or each of X1, X2, X3, Y1, Y2 and Y3 represents CH. In a further embodiment, one of X1, X2 and X3 represents N and one of Y1, Y2 and Y3 represents N. Within this embodiment, X3 and Y1 most suitably represent N.

$Ar^1$ represents phenyl or 6-membered heteroaryl comprising up to 2 nitrogen atoms, optionally substituted as defined previously. Suitable heteroaryl rings include pyridine, pyrimidine, pyrazine and pyridazine, but $Ar^1$ preferably represents optionally substituted phenyl or pyridyl, most preferably optionally substituted phenyl. $Ar^1$ preferably comprises 1 or 2 substituents which are suitably selected from halogen (preferably F or Cl, most preferably F), CN, $C_{1-4}$alkyl (especially methyl), hydroxymethyl, OH and $C_{1-4}$alkoxy (e.g. methoxy). Suitable embodiments of $Ar^1$ include phenyl, 2-fluorophenyl, 3-fluorophenyl, 4-fluorophenyl, 2,4-difluorophenyl, 3-cyanophenyl, 4-cyanophenyl, 2-chloro-4-fluorophenyl, 4-fluoro-2-methylphenyl, 4-fluoro-2-hydroxyphenyl, 4-chlorophenyl, 2-hydroxyphenyl, 2-cyano-4-fluorophenyl, 4-fluoro-2-methoxyphenyl, 4-fluoro-2-hydroxymethylphenyl, 2-methylphenyl and 5-fluoropyridin-2-yl. In a particular embodiment, $Ar^1$ represents 4-fluorophenyl or 2,4-difluorophenyl.

$Ar^2$ represents phenyl or 5- or 6-membered heteroaryl in which up to 3 ring atoms are selected from N, O and S, said phenyl or heteroaryl bearing 0 to 3 substituents as defined previously. Suitable 6-membered heteroaryl rings include pyridine, pyrimidine, pyrazine and pyridazine, in particular pyridine and pyrimidine. Suitable 5-membered rings include thiophene, furan, pyrrole, pyrazole, imidazole, triazole, thiazole, oxazole, isothiazole and isoxazole, in particular thiophene and imidazole. $Ar^2$ very suitably represents optionally substituted phenyl, pyridyl, pyrimidinyl, thiophenyl or imidazol-2-yl, in particular optionally substituted phenyl or 2-pyridyl. $Ar^2$ typically comprises 1 or 2 substituents, and in a particular embodiment $Ar^2$ bears 1 substituent. When $Ar^2$ bears more than 1 substituent, the additional substituent(s) are preferably halogen (e.g. F or Cl) or $C_{1-4}$alkyl (e.g. methyl). Typical substituents include halogen, CN, $R^a$, $OR^a$, $SR^a$, $SOR^a$, $SO_2R^a$, $SO_2NR^aR^b$, $NR^aR^b$, $CH_2NR^aR^b$, $COR^a$, $CO_2R^a$, $CH_2CO_2R^a$, $CONR^aR^b$, $CR^a=NOR^b$, $NR^aCOR^b$, $NR^aSO_2R^b$, $CH_2NR^aSOR^b$, $N=CHN(Me)_2$, $CH(OH)Ar^3$, $Ar^3$ and $CH_2Ar^3$. Very suitably, $Ar^2$ bears a substituent selected from halogen, CN, $R^a$, $OR^a$, $SR^a$, $SOR^a$, $SO_2R^a$, $COR^a$, $CO_2R^a$, $CONR^aR^b$, and $Ar^3$. When $Ar^2$ bears a single substituent, it is very suitably attached in the ortho position relative to the $S(O)_t$ group.

When $Ar^3$ represents an optionally substituted five-membered heteroaromatic ring, this is suitably an imidazole, pyrazole, 1,2,3-triazole, 1,2,4-triazole, tetrazole, isoxazole, 1,2,4-oxadiazole, 1,3,4-oxadiazole or thiazole ring, any of which optionally is substituted, e.g. by methyl. Such rings may be attached via a carbon atom or a nitrogen atom. Examples include pyrazol-1-yl, imidazol-1-yl, imidazol-2-yl, 2-methyl-1,2,4-triazol-3-yl, isoxazol-5-yl, isoxazol-3-yl, 1,2,4-triazol-2-yl, 1,3,4-oxadiazol-2-yl, 3-methyl-1,2,4-oxadiazol-5-yl, 2-methyl-1,3,4-oxadiazol-5-yl, 3-methylisoxazol-5-yl, 4-methylisoxazol-3-yl, 4-methylthiazol-2-yl, 1,2,4-triazol-3-yl, 1,2,3-triazol-4-yl and imidazol-5-yl.

When $Ar^3$ represents an optionally substituted six-membered heteroaromatic ring, this is suitably a pyridine, pyrazine, pyrimidine, pyridazine or triazine ring, any of which optionally is substituted, e.g. by methyl, methoxy, hydroxy or halogen. Examples include 2-pyridyl, pyrimidin-2-yl, 6-methoxy-3-pyridyl, pyrazin-2-yl, 6-hydroxy-3-pyridyl, and 6-methylpyrimidin-2-yl.

When Ar² bears a substituent represented by CH₂Ar³, Ar³ typically represents an optionally substituted 5-membered heteroaryl ring bonded through nitrogen, such as 1,2,4-triazol-2-yl.

$R^a$ and $R^b$ typically independently represent H, optionally substituted $C_{1-6}$alkyl (such as methyl, ethyl, CF₃, propyl, 2,2,2-trifluoroethyl, 2-cyanoethyl, 1-hydroxyethyl and 2-hydroxyethyl), optionally-substituted $C_{3-6}$cycloalkyl (such as cyclopropyl and 1-hydroxycyclobutyl) or $C_{3-6}$cycloalkyl$C_{1-4}$ alkyl (such as cyclopropylmethyl); or $R^a$ and $R^b$, when linked through a nitrogen atom, may together represent the residue of a heterocyclic ring of 4, 5 or 6 members optionally bearing up to 3 substituents as defined previously. Such rings may be saturated or partially unsaturated, and typically comprise at most two heteroatoms selected from N, O and S, inclusive of the nitrogen atom connecting $R^a$ and $R^b$, for example azetidine, pyrrolidine, piperidine, dihydropyridine, tetrahydropyridine, piperazine, morpholine and thiomorpholine. Typical examples of cyclic groups represented by $NR^aR^b$ include azetidin-1-yl, 3,3-difluoroazetidin-1-yl, 3-hydroxyazetidin-1-yl, pyrrolidin-1-yl, 3-hydroxypyrrolidin-1-yl, 3-fluoropyrrolidin-1-yl, 2-trifluoromethylpyrrolidin-1-yl, piperidin-1-yl, 4-trifluoromethylpiperidin-1-yl, 3-trifluoromethylpiperidin-1-yl, 3-fluoropiperidin-1-yl, 3,3,-difluoropiperidin-1-yl, 4,4-difluoropiperidin-1-yl, 4-trifluoromethyl-1,2,3,6-tetrahydropyridin-1-yl, 4-methylpiperazin-1-yl, 3-oxo-piperazin-1-yl, morpholin-4-yl, 2,6-dimethylmorpholin-4-yl, 1,1-dioxo-thiomorpholin-4-yl, 2-oxo-1,2-dihydropyridin-1-yl and 2-oxopyrrolidin-1-yl.

When $R^a$ is present as a substituent on Ar², $R^a$ very suitably represents substituted $C_{1-6}$ alkyl, in particular hydroxy$C_{1-6}$alkyl such as hydroxymethyl, 1-hydroxyethyl or 2-hydroxyprop-2-yl, or substituted $C_{3-6}$cycloalkyl such as 1-hydroxycyclobutyl.

In a further alternative, two $R^a$ groups attached to adjacent carbon atoms of Ar² complete a fused ring of 5 or 6 members, 0-3 of which are selected from N, O and S while the remainder are carbon, said ring optionally bearing up to 3 substituents selected from halogen CN, CF₃, oxo, OH, $C_{1-4}$alkyl and $C_{1-4}$alkoxy. Said ring may thus be carbocyclic or heterocyclic, and may be aromatic or nonaromatic. In a particular embodiment, the two $R^a$ groups complete a 5-membered heteroaromatic ring such as imidazole or triazole. Examples of groups represented by Ar² within this embodiment include 9H-purine-6-yl, benzimidazol-4-yl and benzotriazol-4-yl.

Specific examples of groups represented by Ar² include phenyl, 2-cyanophenyl, 3-cyanophenyl, 4-cyanophenyl, 2-carbamoylphenyl, 3-carbamoylphenyl, 4-carbamoylphenyl, 2-(1-hydroxyethyl)phenyl, 2-(hydroxymethyl)phenyl, 2-(2-hydroxyprop-2-yl)phenyl, 2-acetylphenyl, 2-formylphenyl, 2-methylthiophenyl, 2-methylsulfinylphenyl, 2-methylsulfonylphenyl, 2-(1-hydroxycyclobutyl)phenyl, and 6-(1-hydroxyethyl)pyrid-2-yl. Further specific examples of groups represented by Ar² include pyrid-2-yl, pyrid-3-yl, 2-methoxycarbonylphenyl, 6-methoxycarbonylpyrid-2yl, 6-(1-hydroxycyclobutyl)pyrid-2-yl, 4-(1-hydroxycyclobutyl)pyrid-3-yl, 2-acetyl-6-methylphenyl, 4-(hydroxymethyl)pyrid-3-yl, 2-(1-hydroxyethyl)-6-methylphenyl, 2-acetylpyrid-3-yl, 2-(1-hydroxyethyl)pyrid-3-yl, 2-(1,2-dihydroxyethyl)phenyl and 2-(1-hydroxy-2-methoxyethyl)phenyl, 2-thienyl, 3-(hydroxymethyl)-2-thienyl, 4-(hydroxymethyl)-3-thienyl, 4-(1-hydroxyethyl)-3-thienyl, 1-methylimidazol-2-yl and 1-(2-hydroxyethyl)imidazol-2-yl.

In a particular aspect, the invention provides a compound of formula II:

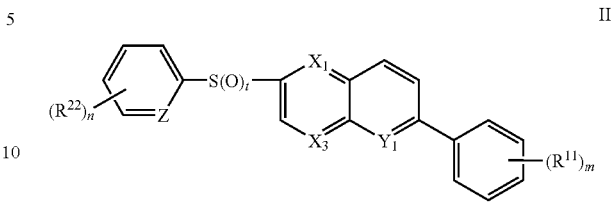

or a pharmaceutically acceptable salt or hydrate thereof;

where m and n are independently 0, 1 or 2;

t is 1 or 2;

X1, X3 and Y1 each represents CH or N provide that X1 and X3 do not both represent N and provided that X1 and Y1 do not both represent N;

Z represents CH or N, or when n is 1 or more Z may represent $CR^{22}$;

$R^{11}$ represents halogen, CN, $C_{1-4}$alkyl, hydroxymethyl, OH or $C_{1-4}$alkoxy;

$R^{22}$ represents halogen, CN, $R^a$, $OR^a$, $SR^a$, $SOR^a$, $SO_2R^a$, $SO_2NR^aR^b$, $NR^aR^b$, $CH_2NR^aR^b$, $COR^a$, $CO_2R^a$, $CH_2CO_2R^a$, $CONR^aR^b$, $CR^a=NOR^b$, $NR^aCOR^b$, $NR^aSO_2R^b$, $CH_2NR^aSOR^b$, $N=CHN(Me)_2$, $CH(OH)Ar^3$, Ar³ or $CH_2Ar^3$; provided that when n is 2 at least one $R^{22}$ group is halogen or $C_{1-4}$alkyl; and Ar³, $R^a$ and $R^b$ have the same definitions and may have the same specific identities as recited previously.

In a particular subset of the compounds of formula II, X3 is H and $R^{22}$ represents halogen, CN, $R^a$, $OR^a$, $SR^a$, $SOR^a$, $SO_2R^a$, $SO_2NR^aR^b$, $NR^aR^b$, $CH_2NR^aR^b$, $COR^a$, $CO_2R^a$, $CONR^aR^b$, or $CH=NOR^a$.

In formula II, m is preferably 1 or 2 and $R^{11}$ is attached at the 2- and/or 4-positions. Each $R^{11}$ is preferably independently selected from F, Cl, CN, methyl, hydroxymethyl and methoxy, of which F is particularly preferred. In a particular embodiment, $(R^{11})_m$ represents 4-fluoro- or 2,4-difluoro-substitution.

In formula II, n is typically 0 or 1, in particular 1. When n is 2, at least one of the $R^{22}$ groups is halogen (e.g. F or Cl) or $C_{1-4}$alkyl (e.g. methyl). In a particular embodiment, n is 1 and $R^{22}$ is selected from CN, hydroxy$C_{1-6}$alkyl (in particular hydroxymethyl, 1-hydroxyethyl or 2-hydroxyprop-2-yl), substituted $C_{3-6}$cycloalkyl (in particular 1-hydroxycyclobutyl), $C_{1-6}$ alkylthio (in particular methylthio), $C_{1-6}$ alkylsulfinyl (in particular methylsulfinyl), $C_{1-6}$ alkylsulfonyl (in particular methanesulfonyl), $C_{1-6}$ alkylcarbonyl (in particular acetyl), formyl, $CONR^aR^b$ (in particular $CONH_2$), $CO_2R^a$ (in particular methoxycarbonyl), $NR^aR^b$ (in particular where $R^a$ and $R^b$ complete a heterocyclic ring such as 2-oxopyrrolidin-1-yl and 2-oxo-1,2-dihydropyridin-1-yl) or Ar³.

Specific compounds of this invention include those compounds exemplified hereinafter and their pharmaceutically acceptable salts.

The compounds of the present invention have an activity as antagonists of the human 5-HT$_{2A}$ receptor and hence find use in the treatment or prevention of disorders mediated by 5-HT$_{2A}$ receptor activity.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient typically is mixed with a pharmaceutical carrier, e.g. conventional tableting ingredients such as corn starch, lactose, sucrose, sorbitol, talc, stearic acid, magnesium stearate and dicalcium phosphate, or gums, dispersing agents, suspending agents or surfactants such as sorbitan monooleate and polyethylene glycol, and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of formula I or a pharmaceutically acceptable salt thereof for use in a method of treatment of the human body. Preferably the treatment is for a condition mediated by $5\text{-HT}_{2A}$ receptor activity.

The present invention further provides the use of a compound of formula I or a pharmaceutically acceptable salt thereof in the manufacture of a medicament for treating or preventing a condition mediated by $5\text{-HT}_{2A}$ receptor activity.

Also disclosed is a method of treatment of a subject suffering from or prone to a condition mediated by $5\text{-HT}_{2A}$ receptor activity which comprises administering to that subject an effective amount of a compound according to formula I or a pharmaceutically acceptable salt thereof.

In one aspect of the invention, the condition mediated by $5\text{-HT}_{2A}$ receptor activity is sleep disorder, in particular insomnia. In a further aspect of the invention, the condition mediated by $5\text{-HT}_{2A}$ receptor activity is selected from psychotic disorders (such as schizophrenia), depression, anxiety, panic disorder, obsessive-compulsive disorder, pain, glaucoma, eating disorders (such as anorexia nervosa), dependency or acute toxicity associated with narcotic agents such as LSD or MDMA, and hot flushes associated with the menopause.

In the treatment envisaged herein, for example of insomnia or schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day but preferably once per day, for example before going to bed.

If desired, the compounds according to this invention may be co-administered with another sleep inducing or anti-schizophrenic or anxiolytic medicament. Such co-administration may be desirable where a patient is already established on sleep inducing or anti-schizophrenic or anxiolytic treatment regime involving other conventional medicaments. In particular, for the treatment of sleep disorders, the compounds of the invention may be co-administered with a $\text{GABA}_A$ receptor agonist such as zopiclone, eszopiclone, gaboxadol, or with a short term and/or rapid-onset hypnotic such as zolpidem, or a benzodiazepine, a barbiturate, a prokineticin modulator, an antihistamine, trazodone, or derivative of trazodone as disclosed in WO 03/068148.

According to a further aspect of the invention, there is provided the combination of a compound of formula I or a pharmaceutically acceptable salt or hydrate thereof and gaboxadol for use in treatment or prevention of sleep disorders, schizophrenia or depression.

Also according to the invention, there is provided a method of treatment or prevention of sleep disorders, schizophrenia or depression comprising administering to a subject in need thereof a compound of formula I or a pharmaceutically acceptable salt or hydrate thereof in combination with gaboxadol.

As used herein, the expression "in combination with" requires that therapeutically effective amounts of both a compound of formula I or a pharmaceutically acceptable salt or hydrate thereof and gaboxadol are administered to the subject, but places no restriction on the manner in which this is achieved. Thus, the two species may be combined in a single dosage form for simultaneous administration to the subject, or may be provided in separate dosage forms for simultaneous or sequential administration to the subject. Sequential administration may be close in time or remote in time, e.g. one species administered in the morning and the other in the evening. The separate species may be administered at the same frequency or at different frequencies, e.g. one species once a day and the other two or more times a day. The separate species may be administered by the same route or by different routes, e.g. one species orally and the other parenterally, although oral administration of both species is preferred, where possible.

According to a further aspect of the invention there is provided a pharmaceutical composition comprising, in a pharmaceutically acceptable carrier, a compound of formula I or a pharmaceutically acceptable salt or hydrate thereof and gaboxadol.

The invention further provides the use, for the manufacture of a medicament for treatment or prevention of sleep disorders, schizophrenia or depression, of a compound of formula I or a pharmaceutically acceptable salt or hydrate thereof and gaboxadol.

The invention further provides a kit comprising a first medicament comprising a compound of formula I or a pharmaceutically acceptable salt or hydrate thereof and a second medicament comprising gaboxadol together with instructions for administering said medicaments sequentially or simultaneously to a patient suffering from a sleep disorder, schizophrenia or depression.

As used herein, the term "gaboxadol" is inclusive of 4,5,6,7-tetrahydroisoxazolo[5,4-c]pyridin-3-ol in free base or zwitterionic form and also of pharmaceutically acceptable acid addition salts thereof such as the hydrochloride salt. Most suitably, gaboxadol is in the form of a crystalline monohydrate of the zwitterionic form.

Compounds of formula I may be prepared by oxidation of sulfides (1):

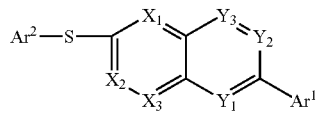

(1)

where $Ar^1$, $Ar^2$, X1-X3 and Y1-Y3 have the same meanings as before. Suitable oxidants include m-chloroperoxybenzoic acid and oxone. Use of one molar equivalent of oxidant provides sulfoxides (i.e. t=1 in formula I), while use of two or more equivalents provides the sulfones (t=2 in formula I).

Sulfides (1) may be obtained by reaction of $Ar^2$—Q1 with compounds (2):

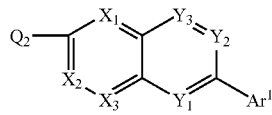

(2)

where one of Q1 and Q2 is SH and the other is a leaving group such Cl, Br, I or triflate, and $Ar^1$, $Ar^2$, X1-X3 and Y1-Y3 have the same meanings as before. The reaction may be carried out in an alcoholic solvent (e.g. isopropanol) at about 80° C. in the presence of CuI and a base such as potassium carbonate. Alternatively, the reaction may be carried out at reflux in an ether solvent (such as dioxan) in the presence of base, a Pd(0) catalyst and a triarylphosphine.

Compounds (2) in which Q2 represents SH may be obtained by reaction of the corresponding bromides (2) (Q2=Br) with triisopropylsilyl sulfide and treatment of the product with a tetraalkylammonium fluoride. The initial reaction takes place in the presence of sodium hydride and $(Ph_3P)_4Pd(0)$ in an anhydrous solvent such as THF, initially at 0° C. and then at reflux. Treatment with the tetraalkylammonium fluoride (e.g. tetrabutylammonium fluoride) may be carried out at 0° C. in THF.

Alternatively, compounds (2) in which Q2 represents SH may be obtained by conversion of the corresponding phenols (2) (Q2=OH) to the corresponding dimethylthiocarbamates (e.g. by treatment with N,N-dimethylthiocarbamoyl chloride in DMF in the presence of sodium hydride), followed by heating to about 250° C. and alkaline hydrolysis.

Compounds (2) may be obtained by Suzuki coupling of compounds (3):

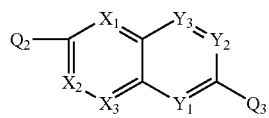

(3)

with boronic acids $Ar^1$—$B(OH)_2$, where Q3 represents a leaving group such as Cl, Br, I or triflate, and $Ar^1$, Q2, X1-X3 and Y1-Y3 have the same meanings as before (but Q2 is preferably not SH). The coupling takes place under standard Suzuki conditions, e.g. in a solvent such as toluene, dioxan or dimethoxyethane at elevated temperature in the presence of a base such as an alkali metal carbonate or phosphate, a Pd(0) or Pd(II) catalyst and a triaryl phosphine catalyst. If desired, the coupling may be "reversed" by replacing Q3 in (3) with a boronic acid or boronate ester group, and reacting this with $Ar^1$—Q3 where Q3 has the same meaning as before. In the case where Y1 represents N and X1-X3, Y2 and Y3 represent CH, compounds (2) may alternatively be obtained by treatment of compounds (3) (Q3=H) with $Ar^1MgHal$ and $MnO_2$, where Hal represents Cl, Br or I.

Compounds (2) in which X3 represents N and X1, X3 and Y1-Y3 represent CH, and Q2 is Br, may be obtained by Suzuki coupling of 7-(4,4,5,5-tetramethyl-1,3,2-dioxaborolan-2-yl)quinoline (WO 2005/047279) with $Ar^1$—Q3, formation of the hydrochloride salt, then treatment with bromine in nitrobenzene at about 140° C.

Compounds (2) (Q2=Br) in which X3 and Y1 are N and X2, X3, Y1 and Y2 are CH are available by condensation of 2-amino-5-bromonicotinaldehyde with $Ar^1COCH_3$ (e.g. in refluxing aqueous-ethanolic KOH).

In a variation of the above route, compounds (3) are reacted first with $Ar^2$—Q1, followed by oxidation of the resulting thioether, then Suzuki coupling with $Ar^1$—$B(OH)_2$.

An alternative route to compounds of formula I in which t is 2 comprises reaction of $Ar^2$—Q4 with a compound of formula (4):

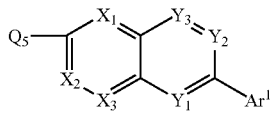

(4)

where one of Q4 and Q5 represents $SO_2M$ where M is an alkali metal (e.g. sodium) and the other is a leaving group such as Cl, Br, I or triflate, and $Ar^1$, $Ar^2$, X1-X3 and Y1-Y3 have the same meanings as before. The reaction takes place in DMSO at elevated temperatures in the presence of CuI, or alternatively in toluene at elevated temperature in the presence of tris(dibenzylideneacetone)dipalladium(0) and a phosphine catalyst (e.g. 4,5-bis(diphenylphosphino)-9,9-dimethylxanthene).

Compounds (4) in which Q5 represents $SO_2M$ may be prepared from the corresponding compounds (2) in which Q2 represents SH by reaction with acrylonitrile to form the corresponding cyanoethyl sulfide, oxidation (e.g. with m-chloroperoxybenzoic acid) and treatment of the resulting sulfone with sodium methoxide.

Alternatively, the said compounds may be obtained by treatment of compounds (2) (Q2=Br) with an alkyl ester (e.g. methyl) of mercaptopropionic acid, followed by oxidation of the resulting thioether (e.g. with oxone and moist alumina in refluxing chloroform), then treatment of the resulting sulfone with sodium methoxide. The reaction with mercaptopropionate ester takes place in refluxing dioxan in the presence of a Pd(0) catalyst and a triarylphosphine (i.e. Suzuki coupling conditions).

If desired, the above route may be modified so as to attach the $Ar^2SO_2$ moiety to the bicyclic core prior to attaching the $Ar^1$ group, simply by reversing the order in which the steps are carried out.

An alternative route to compounds of formula I in which Y1 represents N and Y2, Y3 and X1-X3 represent CH comprises reaction of an iodoaniline (5) with an alkenol (6):

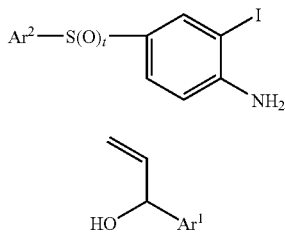

where t, $Ar^1$ and $Ar^2$ have the same meanings as before. The reaction takes place in hexamethylphosphoramide at elevated temperature (e.g. about 140° C.) in the presence of base (such as sodium hydrogen carbonate), a Pd(II) salt (e.g. the diacetate) and a phosphine (e.g. triphenylphosphine).

It will be appreciated that any compound of formula I initially obtained from any of the above processes may, where appropriate, subsequently be elaborated into a further desired compound of formula I using techniques known from the art. For example, a bromo substituent present on $Ar^1$ or $Ar^2$ may be replaced by cyano by treatment with copper(I) cyamide in the presence of 1-methyl-2-pyrrolidinone (NMP), or with zinc cyamide in the presence of tetrakis(triphenylphosphine)palladium(0). The cyano group thereby obtained may in turn be converted into carboxamido by heating in mineral acid, e.g. 85% sulphuric acid at 100° C., or by treatment with potassium trimethylsilanolate, typically in tetrahydrofuran at reflux, or by treatment with alkaline hydrogen peroxide. Similarly, a fluoro substituent present on $Ar^2$ may be replaced by $NR^aR^b$ or an optionally substituted N-linked heteroaryl moiety, e.g. imidazol-1-yl, pyrazol-1-yl, 1,2,3-triazol-1-yl or 1,2,4-triazol-1-yl, by treatment with $HNR^aR^b$ or the appropriate optionally substituted N-containing heteroaryl compound, typically with heating in DMSO. Similarly, a bromo substituent present on $Ar^2$ may be replaced by an optionally substituted C-linked five-membered heteroaromatic ring, e.g. 2-methyltetrazol-5-yl or 1-methyl-1,2,4-triazol-5-yl, by reaction with a tributylstannyl derivative of the appropriate heteroaromatic compound, e.g. 2-methyl-5-tributylstannyltetrazole or 1-methyl-5-tributylstannyl-1,2,4-triazole, in the presence of a transition metal catalyst such as tetrakis(triphenylphosphine)palladium(0), typically with heating in a solvent such as N,N-dimethylformamide. A cyano substituent present on $Ar^2$ may be converted to CHO by diisobutylaluminium hydride (DIBAL-H) reduction and hydrolysis. A CHO substituent present on $Ar^2$ may be converted to $CH_2NR^aR^b$ by treatment with $HNR^aR^b$ and sodium triacetoxyborohydride or sodium cyanoborohydride. A substituent $COR^a$ present on $Ar^2$ may be converted to $CH(OH)R^a$ by reduction (e.g. using sodium borohydride) or to $CR^a(OH)R^b$ by treatment with $R^bMgHal$ where Hal is Cl, Br or I. A CHO or $CO_2R^a$ substituent on $Ar^2$ may be converted to a variety of heteroaryl groups via standard methods of heterocyclic synthesis, e.g. $CO_2R^a$ may be converted to 1,3,4-oxadiazol-2-yl by treatment with hydrazine hydrate. A nitro substituent on $Ar^2$ may be reduced to amino by standard reduction methods. Said amino group may be reacted with dimethylformamide and NaH to provide a $N=CHN(Me)_2$ substituent. An amino or aminomethyl substituent present on $Ar^2$ may be reacted with $R^aCOCl$, $R^aSO_2Cl$ or $R^aSOCl$ to proide the corresponding amides, sulfonamides and sulfinamides. A CHO substituent present on $Ar^2$ may be treated with $Ar^3$—Li or $Ar^3MgHal$ to provide $CH(OH)Ar^3$.

Such processes may also be used to prepare appropriately-substituted precursors of the compounds of formula I such as $Ar^2$—Q1 and $Ar^2$—Q4.

Any nitrogen atom forming part of a heteroaryl ring may be converted to the N-oxide by oxidation, e.g. with m-chloroperbenzoic acid.

Where they are not themselves commercially available, the starting materials and reagents described above may be obtained from commercially available precursors by means of well known synthetic procedures and/or the methods disclosed in the Examples section herein.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as di-p-toluoyl-D-tartaric acid and/or di-p-toluoyl-L-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Compounds were tested for their binding to the 5-$HT_{2A}$ receptor and to other receptors such as 5-$HT_{2C}$ and IKr using the methodology described in Fletcher et al, *J. Med. Chem.*, 2002, 45, 492-503.

EXAMPLES

Example 1

2-(4-Fluorophenyl)-6-(phenylsulfonyl)naphthalene

Step 1: 6-(4-Fluorophenyl)-2-naphthol

Dioxane (100 mL) and 2M sodium carbonate solution (15 mL) were added to a mixture of 6-bromo-2-naphthol (2.3 g, 10 mmol), 4-fluorobenzeneboronic acid (2.2 g, 15 mmol) and tetrakis(triphenylphosphine)palladium(0) (0.6 g). The reaction was heated to 80° C. under nitrogen for 5 hours. The cooled reaction mixture was poured into dilute hydrochloric acid (200 mL) and extracted with ethyl acetate (x3). The combined organic layers were washed with water (x2) and brine, dried over $MgSO_4$ and evaporated in vacuo. The residue was purified by flash column chromatography on silica, eluting with 10-20% ethyl acetate/isohexane, to give 6-(4-fluorophenyl)-2-naphthol as a white solid (1.75 g, 74%). $^1H$ NMR (500 MHz, CDCl$_3$) δ 7.91 (1H, s), 7.80 (1H, d, J=8.8 Hz), 7.75 (1H, d, J=8.5 Hz), 7.65-7.63 (3H, m), 7.18-7.12 (4H, m), 4.97 (1H, s).

Step 2: 6-(4-Fluorophenyl)-2-naphthyl trifluoromethanesulfonate

Trifluoromethanesulfonic anhydride (1.3 mL, 7.74 mmol) was added over 5 minutes to a stirred solution of 6-(4-fluorophenyl)-2-naphthol (Step 1, 1.75 g, 7.35 mmol) in dichloromethane (25 mL) and pyridine (15 mL) at 0° C. under nitrogen. The reaction was stirred at 0° C. for 1 hour then allowed to warm to room temperature. The solvent was removed in vacuo and the residue partitioned between ethyl acetate and water. The combined organic layers were washed with water and brine, dried over MgSO$_4$ and evaporated in vacuo to give 6-(4-fluorophenyl)-2-naphthyl trifluoromethanesulfonate (2.34 g, 86%). $^1$H NMR (500 MHz, CDCl$_3$) δ 8.03 (1H, s), 7.96 (2H, dd, J=9.1, 13.1 Hz), 7.81-7.77 (2H, m), 7.67-7.65 (2H, m), 7.41 (1H, dd, J=2.4, 9.0 Hz), 7.21-7.17 (2H, m).

Step 3: 2-(4-Fluorophenyl)-6-(phenylsulfonyl)naphthalene

A mixture of 6-(4-fluorophenyl)-2-naphthyl trifluoromethanesulfonate (Step 2, 260 mg, 0.7 mmol), cesium carbonate (345 mg, 1.06 mmol), sodium benzenesulfinate (140 mg, 0.85 mmol), tris(dibenzylideneacetone)dipalladium(0) (16 mg), 4,5-bis(diphenylphosphino)-9,9-dimethylxanthene (20 mg) and tert-butylammonium chloride (235 mg, 0.84 mmol) in toluene (5 mL) was heated to 120° C. under nitrogen for 5 hours. The cooled reaction mixture was poured into water and extracted with ethyl acetate (x3). The combined organic layers were washed with water and brine, dried over MgSO$_4$ and evaporated in vacuo. The residue was purified by flash column chromatography on silica, eluting with 20% ethyl acetate/isohexane, followed by trituration with 10% diethyl ether/isohexane to give the title compound as an off-white solid (180 mg, 71%). $^1$H NMR (500 MHz, CDCl$_3$) δ 8.59 (1H, s), 8.05-7.95 (5H, m), 7.88 (1H, dd, J=1.8, 8.6 Hz), 7.81 (1H, dd, J=1.7, 8.5 Hz), 7.67-7.65 (2H, m), 7.57-7.49 (3H, m), 7.20-7.16 (2H, m).

Example 2

2-{[6-(2,4-Difluorophenyl)-2-naphthyl]sulfonyl}benzonitrile

Step 1: 2-Bromo-6-(2,4-difluorophenyl)naphthalene

A mixture of 2,6-dibromonaphthalene (12.49 g, 43.7 mmol), 2,4-difluorobenzeneboronic acid (3.44 g, 21.8 mmol), sodium carbonate (4.63 g, 45.7 mmol), palladium acetate (245 mg, 1.09 mmol) and tri-o-tolylphosphine (667 mg, 2.19 mmol) in water (15 mL) and ethylene glycol dimethyl ether (90 mL) was degassed and heated to 80° C. overnight. The cooled reaction mixture was partitioned between water and ethyl acetate. The aqueous layer was extracted with ethyl acetate. The combined organic layers were washed with brine, dried over MgSO$_4$ and evaporated in vacuo. The residue was purified by flash column chromatography on silica, eluting with isohexane, to give 2-bromo-6-(2,4-difluorophenyl)naphthalene (1.24 g, contains 10% 2,6-dibromonaphthalene). $^1$H NMR (500 MHz, CDCl$_3$) δ 8.04 (1H, s), 7.93 (1H, s), 7.82 (1H, d, J=8.5 Hz), 7.75 (1H, d, J=8.6 Hz), 7.62 (2H, dd, J=8.4, 31.8 Hz), 7.50 (1H, m), 7.04-6.91 (2H, m).

Step 2: 6-(2,4-Difluorophenyl)-2-naphthyl hydrosulfide

Sodium hydride (60% dispersion in mineral oil, 0.25 g, 6.25 mmol) was added to a solution of triisopropylsilyl sulfide (1.2 mL, 5.59 mmol) in tetrahydrofuran (15 mL) at 0° C. The reaction was stirred at 0° C. for 5 minutes then at room temperature for 20 minutes. 2-Bromo-6-(2,4-difluorophenyl)naphthalene (Step 1, 1.63 g, 5.11 mmol) in toluene (30 mL) and tetrakis(triphenylphosphine)palladium(0) (310 mg) were added and the mixture degassed. The reaction was heated to reflux for 3 hours. The cooled reaction mixture was partitioned between water and ethyl acetate. The combined organic layers were washed with brine, dried over MgSO$_4$ and evaporated in vacuo. The residue was suspended in isohexane and silica added. The mixture was filtered, washing the silica with isohexane. The filtrate was evaporated in vacuo and the residue dissolved in tetrahydrofuran (6 mL) and cooled to 0° C. A solution of tetrabutylammonium fluoride (1M in tetrahydrofuran, 3 mL) was added and the reaction stirred at 0° C. for 30 minutes. Water was added then 2M hydrochloric acid. The reaction mixture was extracted with diethyl ether. The combined organic layers were washed with brine, dried over MgSO$_4$ and evaporated in vacuo. The residue was purified by filtration through a plug of silica, eluting with 10% dichloromethane/isohexane, to give 6-(2,4-difluorophenyl)-2-naphthyl hydrosulfide (0.78 g, contains some impurities). $^1$H NMR (500 MHz, CDCl$_3$) δ 7.89 (1H, s), 7.77-7.74 (3H, m), 7.62-7.59 (1H, m), 7.52-7.46 (1H, m), 7.37 (1H, dd, J=1.8, 8.5 Hz), 7.01-6.93 (2H, m), 3.62 (1H, s).

Step 3: 2-{[6-(2,4-Difluorophenyl)-2-naphthyl]thio}benzonitrile 6-(2,4-Difluorophenyl)-2-naphthyl hydrosulfide (Step 2, 0.78 g) was dissolved in isopropyl alcohol (15 mL). 2-Iodobenzonitrile (0.66 g, 2.88 mmol), copper(I) iodide (29 mg, 0.15 mmol), potassium carbonate (0.8 g, 5.79 mmol) and ethylene glycol (320 µL) were added and the reaction heated to 80° C. under nitrogen overnight. Ethyl acetate was added to the cooled reaction mixture and stirred for 15 minutes. The mixture was filtered and the filtrate evaporated in vacuo. The residue was purified by flash column chromatography on silica, eluting with 10-20% ethyl acetate/isohexane, followed by recrystallisation from ethyl acetate/isohexane, to give 2-{[6-(2,4-difluorophenyl)-2-naphthyl]thio}benzonitrile (216 mg, 20%). $^1$H NMR (500 MHz, CDCl$_3$) δ 8.04 (1H, s), 7.97 (1H, s), 7.88 (2H, t, J=7.8 Hz), 7.68 (2H, d, J=8.0 Hz), 7.54-7.48 (2H, m), 7.43-7.39 (1H, m), 7.28 (1H, t, J=7.6 Hz), 7.19 (1H, d, J=7.9 Hz), 7.03-6.95 (2H, m).

Step 4: 2-{[6-(2,4-Difluorophenyl)-2-naphthyl]sulfonyl}benzonitrile

A solution of 2-{[6-(2,4-difluorophenyl)-2-naphthyl]thio}benzonitrile (Step 3, 212 g, 0.57 mmol) in dichloromethane (10 mL) was cooled to 0° C. 3-Chloroperoxybenzoic acid (77%, 387 mg) was added and the reaction stirred at 0° C. for 2 minutes then at room temperature for 23 hours. The reaction mixture was diluted with dichloromethane and washed with saturated sodium hydrogencarbonate solution (x2). The combined aqueous layers were extracted with dichloromethane. The combined organic layers were dried over MgSO$_4$ and evaporated. The residue was purified by flash column chromatography on silica, eluting with 3:1 dichloromethane:isohexane then dichloromethane, followed by recrystallisation from ethyl acetate/isohexane, to give the title compound (93 mg, 40%). $^1$H NMR (500 MHz, CDCl$_3$) δ 8.81 (1H, s), 8.42 (1H, d, J=8.0 Hz), 8.11 (1H, d, J=8.6 Hz), 8.01-7.93 (3H, m), 7.83-7.76 (3H, m), 7.70-7.68 (1H, m), 7.53-7.47 (1H, m), 7.03-6.95 (2H, m).

Example 3

2-{[6-(2,4-Difluorophenyl)-2-naphthyl]sulfonyl}benzamide

A solution of potassium carbonate (96 mg, 0.69 mmol) in water (0.5 mL) was added to 2-{[6-(2,4-difluorophenyl)-2-naphthyl]sulfonyl}benzonitrile (Example 2, 138 mg, 0.34 mmol) in N,N-dimethylformamide (6 mL). Hydrogen peroxide (35 wt %, 120 μL, 1.37 mmol) was added dropwise. The reaction was stirred at room temperature overnight. The reaction mixture was diluted with water (60 mL). The resulting precipitate was collected by filtration and recrystallised from ethyl acetate/isohexane to give the title compound (118 mg, 82%). $^1$H NMR (500 MHz, d$_6$-DMSO) δ 8.68 (1H, s), 8.22 (1H, d, J=8.6 Hz), 8.16 (3H, dd, J=6.9, 15.7 Hz), 8.02 (1H, d, J=8.8 Hz), 7.98 (1H, s), 7.81 (1H, d, J=8.5 Hz), 7.75-7.69 (2H, m), 7.66 (1H, t, J=7.2 Hz), 7.60 (1H, s), 7.47 (1H, d, J=7.2 Hz), 7.45-7.39 (1H, m), 7.27-7.23 (1H, m); m/z (ES$^+$) 407 [(M-NH$_2$)$^+$]

Example 4

(1R,S)-1-(2-{[6-(2,4-Difluorophenyl)-2-naphthyl]sulfonyl}phenyl)ethanol

A solution of 2-{[6-(2,4-difluorophenyl)-2-naphthyl]sulfonyl}benzonitrile (Example 2, 77 mg, 0.19 mmol) in dichloromethane (5 mL) was cooled to −3° C. Diisobutylaluminium hydride (1M in toluene, 290 μL, 0.29 mmol) was added dropwise, maintaining the internal temperature below −1° C. The reaction was stirred at −3 to +5° C. for 2 hours, then at room temperature for 3 hours. The reaction mixture was recooled to −1° C. and further diisobutylaluminium hydride (1.5M, 190 μL, 0.29 mmol) was added. The reaction was stirred at −3 to +5° C. for 1.5 hours, then at room temperature overnight. The reaction was quenched with methanol and 5M hydrochloric acid added. The mixture was stirred vigorously for 2 hours. Water and 5M hydrochloric acid were added and the aqueous layer extracted with dichloromethane. The combined organic layers were washed with saturated sodium hydrogencarbonate solution, dried over MgSO$_4$ and evaporated in vacuo to give a mixture of 2-{[6-(2,4-difluorophenyl)-2-naphthyl]sulfonyl}benzaldehyde and starting 2-{[6-(2,4-difluorophenyl)-2-naphthyl]sulfonyl}benzonitrile (75 mg) which was dissolved in toluene (2 mL). Methyl magnesium bromide (1.4M in toluene/tetrahydrofuran, 390 μL, 0.546 mmol) was added and the reaction heated to 85° C. under nitrogen for 1.5 hours. 5M Hydrochloric acid (1 mL) was added dropwise to the cooled reaction mixture then stirred at 85° C. for 30 minutes. The cooled reaction mixture was diluted with water and extracted with ethyl acetate. The combined organic layers were washed with brine, dried over MgSO$_4$ and evaporated. The residue was dissolved in methanol (4 mL) and treated with sodium borohydride (19 mg, 0.5 mmol) then stirred at room temperature for 30 minutes. Further sodium borohydride (28 mg, 0.74 mmol) was added and stirring continued for 2 hours. Further sodium borohydride (15 mg, 0.39 mmol) was added and stirring continued for 1 hour. The solvent was removed in vacuo. The residue was partitioned between dilute hydrochloric acid and dichloromethane. The organic layer was dried over MgSO$_4$ and evaporated in vacuo. The residue was purified by preparative TLC, eluting with dichloromethane, followed by flash column chromatography, eluting with 1:2 ethyl acetate/isohexane, to give the title compound (36 mg). $^1$H NMR (500 MHz, CDCl$_3$) δ 8.56 (1H, s), 8.17 (1H, d, J=8.0 Hz), 8.06 (1H, d, J=8.5 Hz), 8.02 (1H, s), 7.98 (1H, d, J=8.7 Hz), 7.78-7.76 (3H, m), 7.66 (1H, t, J=7.6 Hz), 7.54-7.48 (2H, m), 7.04-6.96 (2H, m), 5.65 (1H, q, J=6.4 Hz), 1.35 (3H, d, J=6.3 Hz); m/z (ES$^+$) 407 [(M-OH)$^+$].

Example 5

(1R,S)-(2-{[6-(4-Fluorophenyl)-2-naphthyl]sulfonyl}phenyl)ethanol

Step 1:
O-(6-Bromo-2-naphthyl)dimethylthiocarbamate

Sodium hydride (60% dispersion in mineral oil, 2.66 g, 66.5 mmol) was added portionwise to a solution of 6-bromo-2-naphthol (15.2 g, 66.1 mmol) in N,N-dimethylformamide (120 mL) under nitrogen. The reaction was stirred at room temperature for 1.5 hours. N,N-Dimethylthiocarbamoyl chloride (14.3 g, 112 mmol) was added slowly. The reaction was stirred for 1.5 hours. The mixture was poured into water and extracted with ethyl acetate (x3). The combined organic layers were washed with water and brine, dried over MgSO$_4$ and evaporated in vacuo. The residue was triturated with diethyl ether/isohexane to give O-(6-bromo-2-naphthyl)dimethylthiocarbamate (11.3 g, 55%). $^1$H NMR (500 MHz, CDCl$_3$) δ 8.01 (1H, d, J=1.6 Hz), 7.76 (1H, d, J=8.9 Hz), 7.67 (1H, d, J=8.8 Hz), 7.55 (1H, dd, J=1.9, 8.7 Hz), 7.47 (1H, d, J=2.1 Hz), 7.27 (1H, dd, J=2.3, 8.9 Hz), 3.48 (3H, s), 3.40 (3H, s).

Step 2: 6-Bromo-2-naphthyl hydrosulfide

O-(6-Bromo-2-naphthyl)dimethylthiocarbamate (Step 1, 8 g, 25.8 mmol) was plunged into a pre-heated sandbath at 250° C. under nitrogen for 6.5 hours. After cooling, ethanol (90 mL) and sodium hydroxide (10% w/w in water, 30 mL) were added and the reaction heated to reflux for 5 hours. The cooled reaction mixture was poured into water and dichloromethane and acidified with conc. HCl. The organic layer was washed with water and brine, filtered, dried over MgSO$_4$ and evaporated in vacuo. The residue was triturated with 25% diethyl ether/isohexane to give 6-bromo-2-naphthyl hydrosulfide (3.8 g, 62%). $^1$H NMR (500 MHz, CDCl$_3$) δ 7.93 (1H, s), 7.71 (1H, s), 7.62 (1H, d, J=8.5 Hz), 7.57-7.51 (2H, m), 7.36 (1H, dd, J=1.8, 8.5 Hz), 3.60 (1H, s).

Step 3:
2-[(6-Bromo-2-naphthyl)sulfonyl]benzonitrile

A mixture of 6-bromo-2-naphthyl hydrosulfide (Step 2, 2.08 g, 8.7 mmol), 2-iodobenzonitrile (2 g, 8.56 mmol), copper(I) iodide (83 mg, 0.44 mmol) and potassium carbonate (2.4 g, 17.4 mmol) was degassed then isopropyl alcohol (10 mL) and ethylene glycol (0.97 mL, 17.4 mmol) added. The reaction was heated to 80° overnight. The cooled reaction mixture was poured into water and extracted with dichloromethane (x3). The combined organic layers were washed with ammonium chloride solution, water and brine, filtered, dried over MgSO$_4$ and evaporated in vacuo to give 2-[(6-bromo-2-naphthyl)thio]benzonitrile (2.85 g, containing some 2,2'-dithiobis(6-bromonaphthalene)). 2.19 g of this was treated according to the method of Example 2 Step 4 to give 2-[(6-bromo-2-naphthyl)sulfonyl]benzonitrile (1.33 g, 56%). $^1$H NMR (500 MHz, CDCl$_3$) δ 8.76 (1H, s), 8.41 (1H, d, J=8.0 Hz), 8.07 (1H, s), 7.94-7.79 (5H, m), 7.72-7.68 (2H, m); m/z (ES$^+$) 372, 374 [MH$^+$].

Step 4: 2-{[6-(4-Fluorophenyl)-2-naphthyl]sulfonyl}benzonitrile

Prepared from 2-[(6-bromo-2-naphthyl)sulfonyl]benzonitrile (Step 3) and 4-fluorobenzeneboronic acid according to the method of Example 2 Step 1. $^1$H NMR (500 MHz, CDCl$_3$) δ 8.80 (1H, s), 8.42 (1H, d, J=7.9 Hz), 8.11 (1H, d, J=8.6 Hz), 8.00 (2H, t, J=9.0 Hz), 7.93 (1H, dd, J=1.7, 8.7 Hz), 7.85-7.79 (3H, m), 7.70-7.64 (3H, m), 7.19 (2H, t, J=8.6 Hz).

Step 5: 2-{[6-(4-Fluorophenyl)-2-naphthyl]sulfonyl}benzaldehyde

A solution of 2-{[6-(4-fluorophenyl)-2-naphthyl]sulfonyl}benzonitrile (Step 4, 226 mg, 0.583 mmol) was cooled to 0° C. and diisobutylaluminium hydride (1.5M in toluene, 780 µL, 1.17 mmol) was added dropwise. The reaction was stirred at −2 to +4° C. under nitrogen for 1.5 hours then quenched with methanol (500 µL). 5M Hydrochloric acid was added and the mixture stirred vigorously overnight. The mixture was diluted with water and the aqueous layer extracted with dichloromethane. The combined organic layers were washed with saturated sodium hydrogencarbonate solution, dried over MgSO$_4$ and evaporated in vacuo. The residue was triturated with diethyl ether to give 2-{[6-(4-fluorophenyl)-2-naphthyl]sulfonyl}benzaldehyde (138 mg, 61%). $^1$H NMR (500 MHz, CDCl$_3$) δ 10.96 (1H, s), 8.56 (1H, s), 8.26 (1H, d, J=7.8 Hz), 8.06-7.98 (4H, m), 7.84 (1H, dd, J=1.6, 8.5 Hz), 7.81-7.77 (2H, m), 7.74 (1H, t, J=7.4 Hz), 7.67 (2H, dd, J=5.3, 8.7 Hz), 7.20-7.18 (2H, m).

Step 6: (1R,S)-(2-{[6-(4-Fluorophenyl)-2-naphthyl]sulfonyl}phenyl)ethanol

A solution of 2-{[6-(4-fluorophenyl)-2-naphthyl]sulfonyl}benzaldehyde (Step 5, 90 mg, 0.23 mmol) in tetrahydrofuran (3 mL) was cooled to −6° C. Methyl magnesium bromide (1.4M in toluene/tetrahydrofuran, 330 µL, 0.46 mmol) was added dropwise, maintaining the internal temperature below −4° C. The reaction was stirred at −6 to +4° C. for 1.5 hours then further methyl magnesium bromide (1.4M in toluene/tetrahydrofuran, 165 µL, 0.23 mmol) added and stirring continued for 20 hours, allowing the reaction to warm to room temperature. The reaction was quenched with saturated ammonium chloride, diluted with water and extracted with ethyl acetate. The combined organic layers were washed with brine, dried over MgSO$_4$ and evaporated. The residue was purified by flash column chromatography on silica eluting with 1:3 then 1:2 ethyl acetate/isohexane, followed by preparative TLC eluting with 2.5% ethyl acetate/dichloromethane, to give the title compound (36 mg). $^1$H NMR (500 MHz, CDCl$_3$) δ 8.55 (1H, s), 8.17 (1H, d, J=8.0 Hz), 8.04 (2H, t, J=9.9 Hz), 7.97 (1H, d, J=8.7 Hz), 7.84 (1H, dd, J=1.5, 8.5 Hz), 7.76 (2H, d, J=8.5 Hz), 7.69-7.63 (3H, m), 7.49 (1H, t, J=7.2 Hz), 7.19 (2H, t, J=8.6 Hz), 5.65 (1H, q, J=6.3 Hz), 2.49 (1H, s), 1.35 (3H, d, J=6.4 Hz).

Example 6

(1S)-1-(2-{[6-(2,4-Difluorophenyl)-2-naphthyl]sulfonyl}phenyl)ethanol

Step 1: 3-{[6-(2,4-Difluorophenyl)-2-naphthyl]thio}propanenitrile

A mixture of 6-(2,4-difluorophenyl)-2-naphthyl hydrosulfide (prepared from 6-bromo-2-naphthol according to the methods of Example 1 Steps 1 and 2 and Example 2 Step 2, 7.3 g, 24.7 mmol), acrylonitrile (2.6 mL, 39.5 mmol) and triethylamine (370 µL) in tetrahydrofuran (50 mL) was heated to 50° C. under nitrogen for 1 hour. The solvent was removed in vacuo. The residue was triturated with isohexane to give 3-{[6-(2,4-difluorophenyl)-2-naphthyl]thio}propanenitrile (5.58 g). $^1$H NMR (500 MHz, CDCl$_3$) δ 7.94 (1H, s), 7.90 (1H, s), 7.85 (2H, d, J=8.5 Hz), 7.66 (1H, d, J=8.3 Hz), 7.50 (2H, d, J=8.6 Hz), 7.00 (1H, dd, J=2.3, 8.6 Hz), 6.96 (1H, d, J=1.9 Hz), 3.24 (2H, t, J=7.2 Hz), 2.64 (2H, t, J=7.3 Hz).

Step 2: 3-{[6-(2,4-Difluorophenyl)-2-naphthyl]sulfonyl}propanenitrile

Prepared from 3-{[6-(2,4-difluorophenyl)-2-naphthyl]thio}propanenitrile (Step 1) according to the method of Example 2 Step 4. $^1$H NMR (500 MHz, CDCl$_3$) δ 8.54 (1H, s), 8.11-8.08 (3H, m), 7.90 (1H, dd, J=1.1, 8.5 Hz), 7.83 (1H, d, J=8.8 Hz), 7.54 (1H, d, J=8.6 Hz), 7.04 (1H, dd, J=2.2, 8.7 Hz), 6.99 (1H, d, J=2.0 Hz), 3.48 (2H, t, J=7.6 Hz), 2.87 (2H, t, J=7.7 Hz).

Step 3: Sodium 6-(2,4-difluorophenyl)naphthalene-2-sulfinate

Sodium methoxide (0.68 g, 12.6 mmol) was added to a solution of 3-{[6-(2,4-difluorophenyl)-2-naphthyl]sulfonyl}propanenitrile (Step 2, 4.04 g, 11.3 mmol) in tetrahydrofuran/methanol (1:1, 120 mL) and stirred at room temperature under nitrogen for 1 hour. The reaction mixture was diluted with diethyl ether (120 mL) and stirred for 30 minutes. The solid precipitate was collected by filtration to give sodium 6-(2,4-difluorophenyl)naphthalene-2-sulfinate (3.58 g). $^1$H NMR (500 MHz, CD$_3$OD) δ 8.14 (1H, s), 8.03-7.97 (3H, m), 7.84 (1H, d, J=8.4 Hz), 7.66 (2H, dd, J=8.6, 20.2 Hz), 7.10-7.08 (2H, m).

Step 4: (1S)-1-(2-{[6-(2,4-Difluorophenyl)-2-naphthyl]sulfonyl}phenyl)ethanol Sodium 6-(2,4-difluorophenyl)naphthalene-2-sulfinate (Step 3, 486 mg, 1.49 mmol), (1S)-1-(2-bromophenyl)ethanol (260 mg, 1.29 mmol) and copper(I) iodide (1.23 g, 6.46 mmol) were combined in dimethylsulfoxide (10 mL) and degassed. The reaction was heated to 110° C. for 2 hours. The cooled reaction mixture was poured into conc. ammonia solution and extracted with diethyl ether (x4). The combined organic layers were washed with brine, dried over MgSO$_4$ and evaporated in vacuo. The residue was purified by flash column chromatography on silica, eluting with 5% then 10% diethyl ether/dichloromethane, followed by trituration with isohexane. A second column, eluting with 60% diethyl ether/isohexane, followed by trituration with isohexane, gave the title compound (145 mg). $^1$H NMR (500 MHz, CDCl$_3$) δ 8.56 (1H, s), 8.17 (1H, d, J=7.9 Hz), 8.06-7.98 (3H, m), 7.79-7.76 (3H, m), 7.66 (1H, t, J=7.5 Hz), 7.54-7.48 (2H, m), 7.03-6.95 (2H, m), 5.65 (1H, q, J=6.2 Hz), 2.51 (1H, s), 1.35 (3H, d, J=6.3 Hz); m/z (ES$^+$) 407 [(M-OH)$^+$].

Example 7

(1R)-1-(2-{[6-(2,4-Difluorophenyl)-2-naphthyl]sulfonyl}phenyl)ethanol

Prepared according to the method of Example 6, using (1R)-1-(2-iodophenyl)ethanol in Step 4. $^1$H NMR (500 MHz, CDCl$_3$) δ 8.55 (1H, s), 8.17 (1H, d, J=8.0 Hz), 8.06-7.96 (3H, m), 7.79-7.75 (3H, m), 7.65 (1H, t, J=7.6 Hz), 7.54-7.48 (2H, m), 7.03-6.95 (2H, m), 5.65 (1H, q, J=6.3 Hz), 2.54 (1H, s), 1.35 (3H, d, J=6.4 Hz); m/z (ES$^+$) 407 [(M-OH)$^+$].

Example 8

1-(2-{[6-(4-Fluorophenyl)-2-naphthyl]sulfonyl}phenyl)ethanone

Prepared according to the method of Example 6, starting from 6-(4-fluorophenyl)-2-naphthyl hydrosulfide, and using 1-(2-bromophenyl)ethanone in Step 4. $^1$H NMR (400 MHz, CDCl$_3$) δ 8.55 (1H, d, J=1.6 Hz), 8.11 (1H, dd, J=1.0, 7.8 Hz), 8.08 (1H, d, J=8.6 Hz), 7.99-7.91 (3H, m), 7.80 (1H, dd, J=1.8, 8.6 Hz), 7.68-7.54 (4H, m), 7.31 (2H, dd, J=1.4, 7.5 Hz), 7.21-7.15 (2H, m), 2.73 (3H, s); m/z (ES$^+$) 405 [MH$^+$].

Example 9

2-(2-{[6-(4-Fluorophenyl)-2-naphthyl]sulfonyl}phenyl)propan-2-ol

Prepared from 1-(2-{[6-(4-fluorophenyl)-2-naphthyl]sulfonyl}phenyl)ethanone (Example 8) according to the method of Example 5 Step 6. $^1$H NMR (400 MHz, CDCl$_3$) δ 8.41 (1H, d, J=1.6 Hz), 8.22 (1H, dd, J=1.3, 8.1 Hz), 7.99 (2H, t, J=4.3 Hz), 7.93 (1H, d, J=8.8 Hz), 7.81-7.77 (2H, m), 7.67-7.63 (2H, m), 7.57-7.49 (2H, m), 7.43-7.39 (1H, m), 7.20-7.14 (2H, m), 5.00 (1H, s), 1.67 (6H, s); m/z (ES$^+$) 403 [(M-OH)$^+$].

Example 10

(1S)-1-(2-{[6-(4-Fluorophenyl)-2-naphthyl]sulfonyl}phenyl)ethanol

Step 1: (1S)-1-{2-[(6-Bromo-2-naphthyl)thio]phenyl}ethanol

A mixture of 6-bromo-2-naphthyl hydrosulfide (Example 5 Step 2, 1.80 g, 7.53 mmol), (1S)-1-(2-iodophenyl)ethanol (1.82 g, 7.34 mmol), copper(I) iodide (70 mg, 0.37 mmol) and potassium carbonate (2.02 g, 14.6 mmol) was degassed then isopropyl alcohol (10 mL) and ethylene glycol (0.82 mL, 14.7 mmol) added. The reaction was heated to 80° C. overnight. The cooled reaction mixture was diluted with ethyl acetate (40 mL), filtered and concentrated in vacuo. The residue was purified by flash column chromatography, eluting with a 10-20% ethyl acetate/isohexane gradient to give solid (1S)-1-{2-[(6-bromo-2-naphthyl)thio]phenyl}ethanol (2.30 g, 85%). $^1$H NMR (400 MHz, CDCl$_3$) δ 7.94 (1H, s), 7.68 (1H, dd, J 1.4, 7.8), 7.64 (1H, d, J 8.7 Hz), 7.58-7.50 (3H, m), 7.43-7.39 (1H, m), 7.36 (1H, dd, J 1.4, 7.8 Hz), 7.30 (1H, dd, J 1.8, 8.6 Hz), 7.27-7.23 (1H, m), 5.44 (1H, q, J 6.3 Hz), 1.46 (3H, d, J 6.4 Hz); m/z (ES$^+$) 341, 343 [(M-OH)$^+$].

Step 2: (1S)-1-{2-[(6-Bromo-2-naphthyl)sulfonyl]phenyl}ethanol

3-Chloroperoxybenzoic acid (2.85 g, 12.7 mmol) was added to a stirred solution of (1S)-1-{2-[(6-bromo-2-naphthyl)thio]phenyl}ethanol (2.28 g, 6.3 mmol) in dichloromethane (50 mL) at ambient temperature under nitrogen. Calcium hydroxide (1.50 g, 20.2 mmol) was added after 2 hours, stirred for a further 1 hour then filtered and concentrated in vacuo. Purification by flash column chromatography eluting with a 10-40% ethyl acetate/isohexane gradient followed by trituration using isohexane gave solid (1S)-1-{2-[(6-bromo-2-naphthyl)sulfonyl]phenyl}ethanol (1.47 g, 59%). $^1$H NMR (500 MHz, CDCl$_3$) δ 8.50 (1H, s), 8.16 (1H, d, J 7.9 Hz), 8.08 (1H, s), 7.90-7.82 (2H, m), 7.77-7.70 (3H, m), 7.67 (1H, t, J 7.5 Hz), 7.50 (1H, t, J 7.7 Hz), 5.60 (1H, q, J 6.3 Hz), 2.46 (1H, s), 1.33 (3H, d, J 6.3 Hz); m/z (ES$^+$) 373, 375 [(M-OH)$^+$].

Step 3: (1S)-1-(2-{[6-(4-Fluorophenyl)-2-naphthyl]sulfonyl}phenyl)ethanol

The title compound was prepared from (1S)-1-{2-[(6-bromo-2-naphthyl)sulfonyl]phenyl}ethanol (2.0 g, 5.1 mmol) and 4-fluorobenzeneboronic acid (1.1 g, 7.6 mmol) according to the methods of Example 2 Step 1. Crude product was first purified by flash column chromatography eluting with a 20-80% diethyl ether/isohexane gradient then a second flash column chromatography eluting with 10% diethyl ether/dichloromethane. Crystallisation from methanol/H$_2$O gave (1S)-1-(2-{[6-(4-fluorophenyl)-2-naphthyl]sulfonyl}phenyl)ethanol (1.73 g, 83%). $^1$H NMR (500 MHz, CDCl$_3$) δ 8.55 (1H, s), 8.17 (1H, d, J 8.0 Hz), 8.05 (1H, d, J 8.6 Hz), 8.02 (1H, s), 7.97 (1H, d, J 8.7 Hz), 7.84 (1H, dd, J 1.5, 8.5 Hz), 7.76 (2H, d, J 8.4 Hz), 7.69-7.63 (3H, m), 7.49 (1H, t, J 7.2 Hz), 7.19 (2H, t, 8.6 Hz), 5.68-5.62 (1H, m), 2.49 (1H, d, J 3.1 Hz), 1.35 (3H, d, J 6.3 Hz); m/z (ES$^+$) 389 [(M-OH)$^+$].

Example 10(a)

(1S)-1-(2-{[6-(4-Fluorophenyl)-2-naphthyl]sulfonyl}phenyl)ethanol (Alternative Route)

Step 1: Methyl 3-{[6-(4-fluorophenyl)-2-naphthyl]thio}propanoate

A mixture of 6-(4-fluorophenyl)-2-naphthyl trifluoromethanesulfonate [Example 1 Step 2] (834 mg, 2.25 mmol), methyl mercaptopropionate (0.27 mL, 2.4 mmol), N,N-diisopropylethylamine (0.78 mL, 4.5 mmol), tris(dibenzylideneacetone)dipalladium(0) (52 mg, 0.056 mmol) and 4,5-bis(diphenylphosphino)-9,9-dimethylxanthene (65 mg, 0.11 mmol) in 1,4-dioxane (12 mL) was degassed then heated at reflux under nitrogen for 15 hours. The reaction mixture was allowed to cool and concentrated in vacuo. The residue was purified by flash chromatography, eluting with 50-75% dichloromethane/isohexane, to afford methyl 3-{[6-(4-fluorophenyl)-2-naphthyl]thio}propanoate as an off-white solid (759 mg, 99%). $^1$H NMR (500 MHz, CDCl$_3$) δ 7.93 (1H, s), 7.81 (3H, m), 7.70-7.64 (3H, m), 7.47 (1H, dd, J=1.6, 8.7 Hz), 7.17 (2H, t, J=8.6 Hz), 3.69 (3H, s), 3.29 (2H, t, J=7.4 Hz), 2.69 (2H, t, J=7.4 Hz).

Step 2: Sodium 6-(4-fluorophenyl)naphthalene-2-sulfinate

3-Chloroperoxybenzoic acid (77%; 1.24 g, 5.44 mmol) was added portionwise to a solution of methyl 3-{[6-(4-fluorophenyl)-2-naphthyl]thio}propanoate (756 mg, 2.22 mmol) in dichloromethane (20 mL). The resulting mixture was stirred at room temperature under nitrogen for 2 hours. Calcium hydroxide (0.62 g, 8.4 mmol) was added, the mixture diluted with dichloromethane (5 mL) and the resulting slurry stirred for 30 minutes. The mixture was filtered and the filter cake washed thoroughly with dichloromethane. The filtrate was evaporated to afford a pale cream solid (864 mg). This solid was dissolved in tetrahydrofuran (20 mL) with gentle warming, diluted with methanol (5 mL) and treated with sodium methoxide (190 mg, 3.52 mmol). The resulting mixture was stirred at room temperature for 40 minutes, additional sodium methoxide (64 mg, 1.19 mmol) added and stirring continued for a further 25 minutes. The precipitate was collected under suction and washed with tetrahydrofuran. The solid was suspended in water (5 mL) and stirred for 1 hour. The solid was collected under suction, washed with a little water and dried in vacuo over phosphorus pentoxide to give sodium 6-(4-fluorophenyl)naphthalene-2-sulfinate (559 mg, 82%). $^1$H NMR (500 MHz, CD$_3$OD) δ 8.12 (1H, s), 8.09 (1H, s), 8.03-7.98 (2H, m), 7.84-7.76 (4H, m), 7.21 (2H, t, J=8.7 Hz).

Step 3: (1S)-1-(2-{[6-(4-Fluorophenyl)-2-naphthyl]sulfonyl}phenyl)ethanol

A mixture of sodium 6-(4-fluorophenyl)naphthalene-2-sulfinate (340 mg, 1.1 mmol), (1S)-1-(2-bromophenyl)ethanol (205 mg, 1.0 mmol) and copper(I) iodide (0.95 g, 4.99 mmol) in dimethyl sulfoxide (10 mL) was degassed and the flask placed in an oil bath at 110° C. The reaction mixture was stirred at this temperature for 2 hours. The cooled reaction mixture was poured into concentrated ammonia/water (1:1; 100 mL) and extracted with diethyl ether (4×50 mL). The extracts were washed with water then brine, combined, dried (MgSO$_4$) and evaporated. The residue was purified by two flash columns, the first eluting with 5-10% diethyl ether/dichloromethane and the second eluting with 40-60% diethyl ether/isohexane, to give the title compound (120 mg, 29%). $^1$H NMR (500 MHz, CDCl$_3$) δ 8.55 (1H, s), 8.17 (1H, d, J=8.0 Hz), 8.05 (1H, d, J=8.6 Hz), 8.02 (1H, s), 7.97 (1H, d, J=8.7 Hz), 7.84 (1H, dd, J=1.5, 8.5 Hz), 7.76 (2H, d, J=8.4 Hz), 7.69-7.63 (3H, m), 7.49 (1H, t, J=7.2 Hz), 7.19 (2H, t, 8.6 Hz), 5.68-5.62 (1H, m), 2.49 (1H, d, J=3.1 Hz), 1.35 (3H, d, J=6.3 Hz); m/z (ES$^+$) 389 [(M-OH)$^+$].

Example 11

(1R)-1-(2-{[6-(4-Fluorophenyl)-2-naphthyl]sulfonyl}phenyl)ethanol

Prepared according to the method of Example 6 using 6-(4-fluorophenyl)-2-naphthyl hydrosulfide, and using (1R)-1-(2-iodophenyl)ethanol in Step 4. $^1$H NMR (500 MHz, CDCl$_3$) δ 8.55 (1H, s), 8.17 (1H, d, J=7.9 Hz), 8.06 (1H, d, J=8.6 Hz), 8.03 (1H, s), 7.98 (1H, d, J=8.8 Hz), 7.84 (1H, d, J=8.3 Hz), 7.77 (2H, d, J=8.1 Hz), 7.69-7.63 (3H, m), 7.49 (1H, t, J=7.6 Hz), 7.19 (2H, t, J=8.3 Hz), 5.65 (1H, q, J=6.1 Hz), 2.49 (1H, s), 1.35 (3H, d, J=6.3 Hz); m/z (ES$^+$) 389 [(M-OH)$^+$].

Example 12

1-(2-{[6-(4-Fluorophenyl)-2-naphthyl]sulfonyl}pyridin-3-yl)ethanol

Step 1: 1-(2-Bromopyridin-3-yl)ethanol

Butyllithium (1.6M in hexanes, 26.7 mL, 42.7 mmol) was added over 15 minutes to a solution of diisopropylamine (6.0 mL, 42.8 mmol) in tetrahydrofuran (45 mL) at 0 to 5° C. under nitrogen, then stirred for 30 minutes. This solution was cooled to −78° C. and 2-bromopyridine (3.45 mL, 35.8 mmol) was added. The reaction was stirred at −78° C. for 1 hour. Acetaldehyde (2 mL, 35.6 mmol) was added and the reaction stirred at −78° C. for 1 hour then quenched with saturated ammonium chloride solution and allowed to warm to room temperature. The reaction mixture was diluted with water and extracted with ethyl acetate (x3). The combined organic layers were washed with water and brine, dried over MgSO$_4$ and evaporated in vacuo. The residue was purified by flash column chromatography on silica, eluting with 0-10% diethyl ether/dichloromethane, to give 1-(2-bromopyridin-3-yl)ethanol (2.65 g, 37%). $^1$H NMR (400 MHz, CDCl$_3$) δ8.27 (1H, dd, J=2.0, 4.7 Hz), 7.92 (1H, dd, J=2.0, 7.4 Hz), 7.31 (1H, dd, J=4.7, 7.8 Hz), 5.19 (1H, q, J=6.3 Hz), 2.18 (1H, s), 1.51 (3H, d, J=6.4 Hz).

Step 2: 1-(2-{[6-(4-Fluorophenyl)-2-naphthyl]sulfonyl}pyridin-3-yl)ethanol

The title compound was prepared according to the method of Example 6 using 6-(4-fluorophenyl)-2-naphthyl hydrosulfide, and using 1-(2-bromopyridin-3-yl)ethanol (Step 1) in Step 4. $^1$H NMR (500 MHz, CDCl$_3$) δ 8.64 (1H, s), 8.37 (1H, d, J=4.4 Hz), 8.19 (1H, d, J=8.0 Hz), 8.08-8.01 (3H, m), 7.97 (1H, d, J=8.7 Hz), 7.83 (1H, d, J=8.4 Hz), 7.69 (2H, dd, J=5.3, 8.6 Hz), 7.46 (1H, dd, J=4.6, 7.9 Hz), 7.20 (2H, t, J=8.6 Hz), 6.06 (1H, q, J=6.3 Hz), 2.92 (1H, s), 1.67 (3H, d, J=6.0 Hz); m/z (ES$^+$) 390 [(M-OH)$^+$].

Example 13

2-{[6-(2,4-Difluorophenyl)-2-naphthyl]sulfonyl}benzaldehyde

Prepared according to the method of Example 6, using 2-iodobenzaldehyde in Step 4. $^1$H NMR (500 MHz, CDCl$_3$) δ 10.96 (1H, s), 8.57 (1H, s), 8.26 (1H, d, J=7.7 Hz), 8.06-7.98 (4H, m), 7.81-7.73 (4H, m), 7.50 (1H, q, J=7.8 Hz), 7.03-6.95 (2H, m); m/z (ES$^+$) 409 [MH$^+$].

Example 14

2-(4-Fluorophenyl)-6-{[2-(methylthio)phenyl]sulfonyl}naphthalene

Prepared according to the method of Example 6, starting from 6-(4-fluorophenyl)-2-naphthyl hydrosulfide and using 1-iodo-2-(methylthio)benzene in Step 4. $^1$H NMR (400 MHz, CDCl$_3$) δ 8.67 (1H, s), 8.34 (1H, dd, J=1.5, 8.0 Hz), 8.06 (1H, d, J=8.6 Hz), 8.00 (1H, s), 7.93 (1H, d, J=8.8 Hz), 7.87-7.79 (2H, m), 7.68-7.64 (2H, m), 7.54-7.50 (1H, m), 7.37-7.33 (1H, m), 7.27-7.25 (1H, m), 7.21-7.17 (2H, m), 2.36 (3H, s); m/z (ES$^+$) 409 [MH$^+$].

Example 15

1-(2-{[6-(4-Fluorophenyl)-2-naphthyl]sulfonyl}phenyl)cyclobutanol

Prepared according to the method of Example 6, starting from 6-(4-fluorophenyl)-2-naphthyl hydrosulfide and using 1-(2-bromophenyl)cyclobutanol (prepared from 1,2-dibromobenzene and cyclobutanone according to the method of *Angew. Chem. Int. Ed.*, 2004, 43, 3333 and *JACS*, 1968, 90, 3404) in Step 4. $^1$H NMR (500 MHz, CDCl$_3$) δ 8.49 (1H, s), 8.06-7.99 (3H, m), 7.85-7.77 (3H, m), 7.68 (2H, dd, J=5.3, 8.4 Hz), 7.61-7.53 (2H, m), 7.38 (1H, t, J=7.6 Hz), 7.20 (2H, t, J=8.6 Hz), 4.79 (1H, s), 2.55-2.51 (2H, m), 2.48-2.42 (2H, m), 2.34-2.26 (1H, m), 1.70-1.64 (1H, m); m/z (ES$^+$) 415 [(M-OH)$^+$].

Example 16

2-(4-Fluorophenyl)-6-{[2-(methylsulfinyl)phenyl]sulfonyl}naphthalene

Step 1: 1-Iodo-2-(methylsulfinyl)benzene

3-Chloroperoxybenzoic acid (77%, 2.7 g, 11.99 mmol) was added to a solution of 2-iodothioanisole (3 g, 11.99 mmol) in dichloromethane (50 mL). The reaction was stirred for 1 hour. Calcium hydroxide (1.33 g, 18 mmol) was added and the mixture stirred for 15 minutes. The solid was removed by filtration through Hyflo®, washing well with dichloromethane. The filtrate was concentrated in vacuo. The residue was purified by flash column chromatography on silica, eluting with 20% then 40% ethyl acetate/isohexane, to give 1-iodo-2-(methylsulfinyl)benzene as a colourless oil (2.8 g, 88%). $^1$H NMR (500 MHz, CDCl$_3$) δ 7.92 (1H, d, J=7.8 Hz), 7.82 (1H, d, J=7.8 Hz), 7.62 (1H, t, J=7.6 Hz), 7.23-7.21 (1H, m), 2.79 (3H, s).

Step 2: 2-(4-Fluorophenyl)-6-{[2-(methylsulfinyl)phenyl]sulfonyl}naphthalene The title compound was prepared from 1-iodo-2-(methylsulfinyl)benzene (Step 1) and sodium 6-(4-fluorophenyl)naphthalene-2-sulfinate (prepared according to the method of Example 6 Steps 1-3). $^1$H NMR (500 MHz, CDCl$_3$) δ 8.61 (1H, s), 8.31 (1H, d, J=7.8 Hz), 8.21 (1H, d, J=7.8 Hz), 8.06 (1H, d, J=8.5 Hz), 8.01 (1H, s), 7.97 (1H, d, J=8.7 Hz), 7.88-7.82 (3H, m), 7.71-7.65 (3H, m), 7.19 (2H, t, J=8.6 Hz), 3.03 (3H, s); m/z (ES$^+$) 425 [MH$^+$].

Example 17

2-(4-Fluorophenyl)-6-{[2-(methylsulfonyl)phenyl]sulfonyl}naphthalene

Prepared from 2-(4-fluorophenyl)-6-{[2-(methylthio)phenyl]sulfonyl}naphthalene (Example 14) according to the method of Example 2 Step 4. $^1$H NMR (500 MHz, d$_6$-DMSO) δ 8.63 (1H, s), 8.55 (1H, d, J=6.6 Hz), 8.32 (1H, s), 8.25-8.21 (2H, m), 8.13 (1H, d, J=8.8 Hz), 8.08-7.98 (3H, m), 7.89 (2H, dd, J=5.4, 8.7 Hz), 7.84 (1H, dd, J=1.7, 8.7 Hz), 7.35 (2H, t, J=8.8 Hz), 3.53 (3H, s); m/z (ES$^+$) 441 [MH$^+$].

Example 18

(2-{[6-(2,4-Difluorophenyl)quinolin-2-yl]sulfonyl}phenyl)methanol

Step 1: {2-[(6-Chloroquinolin-2-yl)thio]phenyl}methanol

A mixture of 2-mercaptobenzyl alcohol (1.78 g, 12.7 mmol), 2,6-dichloroquinoline (2.48 g, 12.5 mmol) and potassium carbonate (1.73 g, 12.5 mmol) in N,N-dimethylformamide (25 mL) was stirred at room temperature under nitrogen for 3 hours, then at 60° C. for 17 hours. The cooled reaction mixture was poured into water and extracted with ethyl acetate (x2). The combined organic layers were washed with brine, dried over MgSO$_4$ and evaporated. The residue was purified by flash column chromatography on silica, eluting with 5-10% ethyl acetate/dichloromethane, to give {2-[(6-chloroquinolin-2-yl)thio]phenyl}methanol (0.37 g, 9%) as a colourless oil. $^1$H NMR (400 MHz, CDCl$_3$) δ 7.84 (1H, d, J=8.7 Hz), 7.72-7.66 (4H, m), 7.55-7.51 (2H, m), 7.39-7.35 (1H, m), 7.19 (1H, dd, J=1.2, 8.7 Hz), 4.84 (2H, s), 3.78 (1H, s); m/z (ES$^+$) 302, 304 [MH$^+$].

Step 2: {2-[(6-Chloroquinolin-2-yl)sulfonyl]phenyl}methanol

Prepared from {2-[(6-chloroquinolin-2-yl)thio]phenyl}methanol (Step 1) according to the method of Example 16 Step 1. $^1$H NMR (400 MHz, CDCl$_3$) δ 8.34 (1H, d, J=8.6 Hz), 8.25 (1H, d, J=8.6 Hz), 8.19 (1H, dd, J=1.2, 7.9 Hz), 8.03 (1H, d, J=9.1 Hz), 7.89 (1H, d, J=2.3 Hz), 7.73 (1H, dd, J=2.3, 9.1 Hz), 7.66-7.58 (2H, m), 7.53-7.49 (1H, m), 5.08 (2H, d, J=7.0 Hz), 3.97 (1H, t, J=7.1 Hz); m/z (ES$^+$) 334, 336 [MH$^+$].

Step 3: (2-{[6-(2,4-Difluorophenyl)quinolin-2-yl]sulfonyl}phenyl)methanol

A mixture of {2-[(6-chloroquinolin-2-yl)sulfonyl]phenyl}methanol (Step 2, 157 mg, 0.47 mmol), 2,4-difluorobenzeneboronic acid (173 mg, 1.09 mmol), palladium acetate (6 mg, 0.023 mmol), 2-dicyclohexylphosphino-2'-methylbiphenyl (18 mg, 0.05 mmol) and potassium phosphate (313 mg, 1.47 mmol) was degassed. Toluene (2 mL) was added and the mixture degassed again then heated to 90° C. under nitrogen for 1 hour. The cooled reaction mixture was poured into 1M sodium hydroxide solution and extracted with ethyl acetate (x2). The combined organic layers were washed with brine, dried over MgSO$_4$ and evaporated. The residue was purified by flash column chromatography on silica, eluting with 5-10% ethyl acetate/isohexane, followed by recrystallisation from ethyl acetate/isohexane to give the title compound (33 mg, 17%). $^1$H NMR (500 MHz, CDCl$_3$) δ 8.46 (1H, d, J=8.5 Hz), 8.27 (1H, d, J=8.5 Hz), 8.20 (1H, d, J=7.9 Hz), 8.16 (1H, d, J=8.9 Hz), 8.02 (1H, s), 7.94 (1H, d, J=8.8 Hz), 7.65-7.59 (2H, m), 7.53-7.47 (2H, m), 7.04-6.96 (2H, m), 5.12 (2H, d, J=7.0 Hz), 4.18 (1H, t, J=7.1 Hz); m/z (ES$^+$) 412 [MH$^+$].

Example 19

(1S)-1-(2-{[4-(4-Fluorophenyl)quinolin-6-yl]sulfonyl}phenyl)ethanol

Step 1: 6-Bromo-2-(4-fluorophenyl)quinoline

4-Fluorophenylmagnesium bromide (1.0M in tetrahydrofuran, 30 mL, 30 mmol) was added dropwise to a solution of 6-bromoquinoline (5.0 g, 24 mmol) in tetrahydrofuran (50 mL) at −5° C. The reaction was stirred, maintaining the temperature below 0° C. for 1.5 hours, then allowed to warm to room temperature for 70 hours. Further 4-fluorophenylmagnesium bromide was added and the reaction heated to reflux for 20 hours. The cooled reaction mixture was quenched with saturated ammonium chloride solution then poured into water and extracted with ethyl acetate (x2). The combined organic layers were washed with brine, dried over MgSO$_4$ and evaporated. The residue was dissolved in dichloromethane (100 mL). Manganese (IV) oxide (2.22 g, 25.5 mmol) was added and the reaction stirred at room temperature for 1 hour. Further manganese(IV) oxide (4.51 g) was added and stirring continued for 3.5 hours. The reaction mixture was filtered through a plug of silica, washing with dichloromethane. The filtrate was concentrated in vacuo. The residue was stirred in methanol (100 mL) for 5 minutes then removed by filtration to give 6-bromo-2-(4-fluorophenyl)quinoline (4.84 g, 67%). $^1$H NMR (500 MHz, CDCl$_3$) δ 8.17-8.11 (3H, m), 8.02-7.98

(2H, m), 7.85 (1H, d, J=8.6 Hz), 7.79 (1H, dd, J=2.1, 8.9 Hz), 7.21 (2H, t, J=8.6 Hz); m/z (ES$^+$) 302, 304 [MH$^+$].

Step 2: (1S)-1-(2-{[4-(4-Fluorophenyl)quinolin-6-yl]sulfonyl}phenyl)ethanol

The title compound was prepared from 6-bromo-2-(4-fluorophenyl)quinoline according to the methods of Example 2 Step 2 followed by Example 5 Step 3 using (1S)-1-(2-iodophenyl)ethanol. $^1$H NMR (500 MHz, CDCl$_3$) δ 8.52 (1H, d, J=2.0 Hz), 8.35 (1H, d, J=8.7 Hz), 8.22-8.18 (4H, m), 7.99-7.95 (2H, m), 7.78 (1H, d, J=7.8 Hz), 7.68 (1H, t, J=7.1 Hz), 7.53-7.49 (1H, m), 7.23 (2H, t, J=8.6 Hz), 5.65-5.61 (1H, m), 2.51 (1H, s), 1.34 (3H, d, J=6.3 Hz); m/z (ES$^+$) 408 [MH$^+$].

Examples 20 and 21

(1R)- and (1S)-1-(2-{[6-(4-Fluorophenyl)-2-naphthyl]sulfonyl}pyridin-3-yl)ethanol 1-(2-{[6-(4-Fluorophenyl)-2-naphthyl]sulfonyl}pyridin-3-yl)ethanol (Example 12) was separated into its enantiomers by chiral SFC: Chiralcel OJ-H column (250×10 mm i.d.), mobile phase CO$_2$/MeOH 50/50, flow rate 10 ml/min. Peak 1 retention time 4.48 min (Example 20). Peak 2 retention time 5.65 min (Example 21).

Example 20: $^1$H NMR (500 MHz, CDCl$_3$) δ 8.64 (1H, s), 8.37 (1H, dd, J=1.2, 4.4 Hz), 8.18 (1H, d, J=6.9 Hz), 8.09-8.02 (3H, m), 7.97 (1H, dd, J=1.6, 8.6 Hz), 7.83 (1H, dd, J=1.6, 8.5 Hz), 7.69 (2H, dd, J=5.3, 8.6 Hz), 7.46 (1H, dd, J=4.5, 7.9 Hz), 7.20 (2H, t, J=8.6 Hz), 6.08-6.02 (1H, m), 2.92 (1H, d, J=3.9 Hz), 1.67 (3H, d, J=6.2 Hz); m/z (ES$^+$) 408 [MH$^+$].

Example 21: $^1$H NMR (500 MHz, CDCl$_3$) δ 8.64 (1H, s), 8.36 (1H, dd, J=1.4, 4.6 Hz), 8.19 (1H, d, J=7.9 Hz), 8.09-8.02 (3H, m), 7.97 (1H, dd, J=1.5, 8.7 Hz), 7.83 (1H, dd, J=1.6, 8.5 Hz), 7.69 (2H, dd, J=5.3, 8.6 Hz), 7.45 (1H, dd, J=4.5, 7.9 Hz), 7.20 (2H, t, J=8.6 Hz), 6.09-6.03 (1H, m), 2.91 (1H, d, J=3.8 Hz), 1.67 (3H, d, J=6.5 Hz); m/z (ES$^+$) 408 [MH$^+$].

Example 22

2-(2,4-Difluorophenyl)-6-(phenylsulfonyl)quinoline

Step 1: [4-(Phenylsulfonyl)phenyl]amine

A mixture of sulfanilic acid (10 g, 0.52 mmol), benzene (4.7 g, 0.56 mmol) and trifluoroacetic anhydride (42 g) in trifluoroacetic acid (42 g) was heated to reflux for 3 days. The solvent was removed in vacuo and the residue taken up in 10% aqueous sodium hydroxide and heated to 100° C. for 15 minutes. The resulting white precipitate was filtered off, washed with water and dried to give [4-(phenylsulfonyl)phenyl]amine. $^1$H NMR (400 MHz, d$_6$-DMSO) δ 7.83-7.81 (2H, m), 7.61-7.51 (5H, m), 6.62-6.58 (2H, m), 6.15 (2H, s).

Step 2: [2-Iodo-4-(phenylsulfonyl)phenyl]amine

Iodine chloride (1.94 g, 12 mmol) in methanol (30 mL) was added to a mixture of [4-(phenylsulfonyl)phenyl]amine (Step 1, 2.33 g, 10 mmol) and calcium carbonate (2.0 g, 20 mmol) in methanol (20 mL). The reaction was stirred at room temperature for 72 hours. The reaction mixture was filtered and the filtrate evaporated. The residue was taken up in ethyl acetate and washed with sodium sulfite solution and brine, then evaporated. The residue was triturated with diethyl ether to give [2-iodo-4-(phenylsulfonyl)phenyl]amine (2.3 g). $^1$H NMR (400 MHz, d$_6$-DMSO) δ 7.99 (1H, d, J=2.1 Hz), 7.87-7.85 (2H, m), 7.64-7.54 (4H, m), 6.77 (1H, d, J=8.6 Hz), 6.24 (2H, s).

Step 3: 1-(2,4-Difluorophenyl)prop-2-en-1-ol 2,4-Difluorobenzaldehyde (1.42 g, 10 mmol) was dissolved in tetrahydrofuran (20 mL) and cooled to 0° C. Vinyl magnesium chloride (1M in tetrahydrofuran, 12 mL, 12 mmol) was added. The reaction was stirred for 30 minutes then quenched with saturated aqueous ammonium chloride. The mixture was extracted with ethyl acetate. The combined organic layers were washed with brine, dried over MgSO$_4$ and evaporated. The residue was purified by flash column chromatography on silica, eluting with 10% ethyl acetate/isohexane, to give 1-(2,4-difluorophenyl)prop-2-en-1-ol (1.15 g). $^1$H NMR (500 MHz, CDCl$_3$) δ 7.45-7.39 (1H, m), 6.90-6.86 (1H, m), 6.81-6.77 (1H, m), 6.07-6.00 (1H, m), 5.48 (1H, d, J=5.1 Hz), 5.35 (1H, d, J=17.1 Hz), 5.23-5.20 (1H, m), 2.06 (1H, s).

Step 4: 2-(2,4-Difluorophenyl)-6-(phenylsulfonyl)quinoline 1-(2,4-Difluorophenyl)prop-2-en-1-ol (Step 3, 260 mg, 1.41 mmol), [2-iodo-4-(phenylsulfonyl)phenyl]amine (Step 2, 359 mg, 1 mmol), palladium acetate (22 mg, 0.1 mmol), sodium hydrogencarbonate (162 mg, 3 mmol) and triphenylphosphine (26 mg, 0.1 mmol) were combined in hexamethylphosphoramide (5 mL) and heated to 140° C. for 16 hours. The reaction mixture was diluted with water and extracted with ethyl acetate. The combined organic layers were washed with brine (x5), dried over MgSO$_4$ and evaporated. The residue was purified by preparative HPLC to give the title compound (39 mg). $^1$H NMR (500 MHz, CDCl$_3$) δ 8.59 (1H, d), 8.32 (1H, d), 8.21-8.14 (2H, m), 8.10 (1H, dd, J=2.1, 8.9 Hz), 8.03-7.98 (3H, m), 7.61-7.52 (3H, m), 7.09-7.05 (1H, m), 6.99-6.94 (1H, m).

Examples 23-28

Using analogous procedures, the following were also prepared:

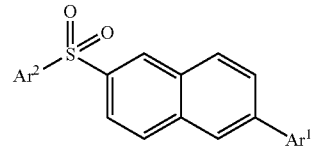

| Example | Ar$^1$ | Ar$^2$ | m/z (ES$^+$) [MH$^+$] |
|---|---|---|---|
| 23 | 4-fluorophenyl | 3-cyanophenyl | |
| 24 | 4-fluorophenyl | 2-cyanophenyl | 388 |
| 25 | 4-fluorophenyl | 2-carbamoylphenyl | 406 |
| 26 | 4-fluorophenyl | 3-carbamoylphenyl | 406 |
| 27 | 4-fluorophenyl | 4-carbamoylphenyl | 406 |
| 28 | 2,4-difluorophenyl | 2-acetylphenyl | 423 |

Example 29

(1S)-1-(2-{[7-(4-Fluorophenyl)quinolin-3-yl]sulfonyl}phenyl)ethanol

Step 1: 7-(4-Fluorophenyl)quinoline hydrochloride

A mixture of 7-(4,4,5,5-tetramethyl-1,3,2-dioxaborolan-2-yl)quinoline [prepared by the method of Hollingworth et al., WO 2005047279] (7.6 g, 30 mmol), 4-fluoro-1-iodobenzene (3.4 mL, 30 mmol), 2 M aqueous sodium carbonate (50 mL) and [1,1'-bis(diphenylphosphino)ferrocene]dichloropalladium(II) (1.22 g, 1.5 mmol) in 1,4-dioxane (150 mL) was degassed then stirred at 80° C. (oil bath temperature) under nitrogen for 18 hours. The reaction mixture was filtered and the filter cake washed with ethyl acetate. Water (150 mL) was added to the filtrate and the mixture extracted with ethyl acetate (2×250 mL). The extracts were washed with brine (100 mL), combined, dried (MgSO$_4$) and evaporated. The residue was purified by flash chromatography, eluting with dichloromethane then 5% ethyl acetate/dichloromethane, to afford a tan solid (3.42 g). This solid was dissolved in dichloromethane (30 mL) and the solution diluted with diethyl ether (30 mL). 1M Hydrogen chloride in diethyl ether (18 mL) was added with swirling to precipitate a solid. The mixture was further diluted with diethyl ether (42 mL) and left to stand for 20 minutes. The solid was collected under suction, washed with 25% dichloromethane/diethyl ether and dried in vacuo to afford 7-(4-fluorophenyl)quinoline hydrochloride (3.90 g, 50%). $^1$H NMR (500 MHz, CD$_3$OD) δ 9.24 (2H, d, J 6.5 Hz), 8.44 (1H, d, J 8.6 Hz), 8.41 (1H, s), 8.31 (1H, dd, J 1.6, 8.6 Hz), 8.10 (1H, m), 7.95-7.93 (2H, m), 7.34 (2H, t, J 8.7 Hz).

Step 2: 3-Bromo-7-(4-fluorophenyl)quinoline

A solution of bromine (0.9 mL, 17.6 mmol) in nitrobenzene (2.5 mL) was added dropwise over 15 minutes to a thick slurry of 7-(4-fluorophenyl)quinoline hydrochloride (3.80 g, 14.6 mmol) in nitrobenzene (7.5 mL) at 140° C. (oil bath temperature). The resulting mixture was stirred at 140° C. for 6 hours, allowed to cool to ca. 80° C., diluted with toluene (30 mL) and then cooled to room temperature. The orange solid was collected under suction and washed with toluene followed by diethyl ether. The solid was suspended in water (100 mL), the mixture basified with aqueous sodium carbonate and extracted with dichloromethane (2×50 mL). The combined extracts were dried (MgSO$_4$) and evaporated to give a yellow solid. This was purified by flash chromatography, eluting with 2:1 dichloromethane/isohexane, dichloromethane then 5% ethyl acetate/dichloromethane, to afford 3-bromo-7-(4-fluorophenyl)quinoline as an off-white solid (2.55 g, 58%). $^1$H NMR (500 MHz, CDCl$_3$) δ 8.93 (1H, d, J 2.2 Hz), 8.33 (1H, d, J 2.1 Hz), 8.24 (1H, s), 7.82-7.78 (2H, m), 7.71-7.69 (2H, m), 7.20 (2H, t, J 8.6 Hz).

Step 3: Methyl 3-{[7-(4-fluorophenyl)quinolin-3-yl]thio}propanoate

A mixture of 3-bromo-7-(4-fluorophenyl)quinoline (503 mg, 1.66 mmol), methyl mercaptopropionate (0.20 mL, 1.8 mmol), N,N-diisopropylethylamine (0.58 mL, 3.3 mmol), tris(dibenzylideneacetone)dipalladium(0) (39 mg, 0.043 mmol) and 4,5-bis(diphenylphosphino)-9,9-dimethylxanthene (50 mg, 0.087 mmol) in 1,4-dioxane (10 mL) was degassed then heated at reflux under nitrogen for 15 hours. The reaction mixture was allowed to cool, filtered and the filter cake washed with ethyl acetate. The residue after evaporation was purified by flash chromatography, eluting with 1:3 then 1:2 ethyl acetate/isohexane, to afford methyl 3-{[7-(4-fluorophenyl)quinolin-3-yl]thio}propanoate as an off-white solid (552 mg, 97%). $^1$H NMR (500 MHz, CDCl$_3$) δ 8.88 (1H, d, J 2.2 Hz), 8.24 (1H, s), 8.13 (1H, d, J 2.0 Hz), 7.82 (1H, d, J 8.4 Hz), 7.78 (1H, dd, J 1.6, 8.4 Hz), 7.71-7.69 (2H, m), 7.21-7.17 (2H, m), 3.69 (3H, s), 3.29 (2H, t, J 7.3 Hz), 2.70 (2H, t, J 7.3 Hz); m/z (ES$^+$) 342 [MH$^+$].

Step 4: Methyl 3-{[7-(4-fluorophenyl)quinolin-3-yl]sulfonyl}propanoate

3-Chloroperoxybenzoic acid (77%; 8.05 g, 36 mmol) was added portionwise to a solution of methyl 3-{[7-(4-fluorophenyl)quinolin-3-yl]thio}propanoate (5.57 g, 16 mmol) in dichloromethane (150 mL). The resulting mixture was stirred at room temperature under nitrogen for 1 hour. Calcium hydroxide (5.1 g, 69 mmol) was added portionwise and the resulting slurry stirred for 30 minutes. The mixture was filtered and the filter cake washed thoroughly with dichloromethane. The filtrate was evaporated and the residue purified by flash chromatography, eluting with 10-15% ethyl acetate/isohexane, to give methyl 3-{[7-(4-fluorophenyl)quinolin-3-yl]sulfonyl}propanoate as a white solid (5.09 g, 84%). $^1$H NMR (500 MHz, CDCl$_3$) δ 9.30 (1H, d, J 2.2 Hz), 8.77 (1H, d, J 2.0 Hz), 8.39 (1H, s), 8.06 (1H, d, J 8.5 Hz), 7.95 (1H, dd, J 1.7, 8.5 Hz), 7.77-7.73 (2H, m), 7.25-7.21 (2H, m), 3.61 (3H, s), 3.59 (2H, t, J 7.5 Hz), 2.86 (2H, t, J 7.5 Hz); m/z (ES$^+$) 374 [MH$^+$].

Step 5: Sodium 7-(4-fluorophenyl)quinoline-3-sulfinate

Methyl 3-{[7-(4-fluorophenyl)quinolin-3-yl]sulfonyl}propanoate (4.23 g, 11.3 mmol) was dissolved/suspended in hot tetrahydrofuran (240 mL). Methanol (60 mL) was added and the mixture allowed to cool to about 30° C., at which point sodium methoxide (0.91 g, 17 mmol) was added and the resulting mixture stirred for 1 hour. The solid present was collected under suction, washed with tetrahydrofuran and dried in vacuo to afford a first crop of sodium 7-(4-fluorophenyl)quinoline-3-sulfinate (2.1 g). The filtrate was concentrated and the residue triturated with tetrahydrofuran. The solid was collected under suction, washed successively with small volumes of tetrahydrofuran, ice-cold water then tetrahydrofuran, and dried in vacuo to give a second crop of product (0.87 g). The combined yield of the title product was 2.97 g (85%). $^1$H NMR (500 MHz, CD$_3$OD) δ 9.13 (1H, d, J 1.9 Hz), 8.52 (1H, d, J 1.6 Hz), 8.24 (1H, s), 8.11 (1H, d, J 8.5 Hz), 7.94 (1H, dd, J 1.7, 8.5 Hz), 7.84-7.82 (2H, m), 7.26 (2H, t, J 8.7 Hz).

Step 6: (1S)-1-(2-{[7-(4-Fluorophenyl)quinolin-3-yl]sulfonyl}phenyl)ethanol

Sodium 7-(4-fluorophenyl)quinoline-3-sulfinate (2.52 g, 8.15 mmol), (1S)-1-(2-iodophenyl)ethanol (2.18 g, 8.79 mmol) and copper(I) iodide (4.69 g, 24.6 mmol) were weighed into a 3-neck round-bottomed flask. A nitrogen atmosphere was established by evacuation and back-filling with nitrogen. Dimethyl sulfoxide (50 mL) was added and the flask placed in an oil bath at 110° C. The reaction mixture was stirred at this temperature for 1 hour. The cooled reaction mixture was poured into concentrated ammonia solution (250 mL) and extracted with ethyl acetate (2×250 ml). The extracts were washed with brine (250 mL), combined, dried (MgSO$_4$) and evaporated to an off-white solid. Recrystallisation from methanol gave the title compound (1.37 g, 41%). $^1$H NMR (500 MHz, DMSO-d$_6$) δ 9.16 (2H, s), 8.41 (1H, d, J 8.6 Hz), 8.39 (1H, s), 8.19 (1H, dd, J 1.0, 8.0 Hz), 8.15 (1H, dd, J 1.7, 8.5 Hz), 7.99-7.97 (2H, m), 7.84 (1H, dd, J 1.0, 7.8 Hz), 7.78 (1H, t, J 7.1 Hz), 7.62-7.58 (1H, m), 7.39 (2H, t, J 8.8 Hz), 5.52-5.46 (1H, m), 5.29 (1H, d, J 3.9 Hz), 1.20 (3H, d, J 6.2 Hz); m/z (ES$^+$) 408 [MH$^+$].

Example 30

Methyl 2-{[2-(4-fluorophenyl)quinolin-6-yl]sulfonyl}benzoate

Step 1: Methyl 2-{[2-(4-fluorophenyl)quinolin-6-yl]thio}benzoate

A mixture of 6-bromo-2-(4-fluorophenyl)quinoline (Example 19 Step 1; 758 mg, 2.51 mmol), methyl thiosalicylate (0.35 mL, 2.54 mmol), N,N-diisopropylethylamine (0.87 mL, 4.99 mmol), tris(dibenzylideneacetone)dipalladium(0) (58 mg, 0.063 mmol) and 4,5-bis(diphenylphosphino)-9,9-dimethylxanthene (74 mg, 0.128 mmol) in 1,4-dioxane (15 mL) was degassed then heated at reflux under nitrogen for 15 hours. The reaction mixture was allowed to cool, concentrated in vacuo and the residue purified by flash chromatography, eluting with 15-25% ethyl acetate/isohexane, to afford methyl 2-{[2-(4-fluorophenyl)quinolin-6-yl]thio}benzoate (0.876, 90%). $^1$H NMR (400 MHz, CDCl$_3$) δ 8.20-8.14 (4H, m), 8.08 (1H, d, J 1.9 Hz), 8.01 (1H, dd, J 1.6, 7.8 Hz), 7.88 (1H, d, J 8.6 Hz), 7.76 (1H, dd, J 2.0, 8.7 Hz), 7.23-7.15 (4H, m), 6.91 (1H, dd, J 0.9, 8.0 Hz), 3.97 (3H, s); m/z (ES$^+$) 390 [MH$^+$].

Step 2: Methyl 2-{[2-(4-fluorophenyl)quinolin-6-yl]sulfonyl}benzoate

3-Chloroperoxybenzoic acid (77%; 597 mg, 2.67 mmol) was added to a solution of methyl 2-{[2-(4-fluorophenyl)quinolin-6-yl]thio}benzoate (346 mg, 0.89 mmol) in dichloromethane (15 mL). The resulting mixture was stirred at room temperature under nitrogen for 1 hour 20 minutes. Calcium hydroxide (308 mg, 4.16 mmol) was added and the resulting slurry stirred for 1 hour 15 minutes. The mixture was filtered and the filter cake washed thoroughly with dichloromethane. The filtrate was evaporated and the residue given a preliminary purification by elution from a silica pad with dichloromethane then 2.5% ethyl acetate/dichloromethane to afford an oil. Crystallisation from diethyl ether gave the title compound, in two crops, as pale yellow crystals (301 mg, 80%). $^1$H NMR (500 MHz, CDCl$_3$) δ 8.57 (1H, d, J 1.7 Hz), 8.36 (1H, d, J 8.7 Hz), 8.25-8.15 (5H, m), 7.95 (1H, d, J 8.6 Hz), 7.67-7.65 (2H, m), 7.61 (1H, m), 7.22 (2H, t, J 8.6 Hz), 3.95 (3H, s); m/z (ES$^+$) 422 [MH$^+$].

Example 31

Methyl 2-{[2-(4-fluorophenyl)-1-oxidoquinolin-6-yl]sulfonyl}benzoate

3-Chloroperoxybenzoic acid (77%; 82 mg, 0.37 mmol) was added to a solution of methyl 2-{[2-(4-fluorophenyl)quinolin-6-yl]sulfonyl}benzoate [Example 30] (103 mg, 0.24 mmol) in dichloromethane (10 mL). The resulting mixture was stirred at room temperature under nitrogen for 2 days. Calcium hydroxide (308 mg, 4.16 mmol) was added and the resulting slurry stirred for 2 hours. The mixture was filtered and the filter cake washed thoroughly with dichloromethane. The filtrate was evaporated and the residue purified by flash chromatography, eluting with 10-25% diethyl ether/dichloromethane, followed by trituration with diethyl ether to give the title compound as a pale yellow solid (45 mg, 42%). $^1$H NMR (500 MHz, CDCl$_3$) δ 8.94 (1H, d, J 9.2 Hz), 8.60 (1H, s), 8.28 (1H, m), 8.19 (1H, dd, J 1.6, 9.2 Hz), 8.02 (2H, dd, J 5.4, 8.7 Hz), 7.87 (1H, d, J 8.7 Hz), 7.71-7.61 (4H, m), 7.22 (2H, t, J 8.6 Hz), 3.95 (3H, s); m/z (ES$^+$) 438 [MH$^+$].

Example 32

1-(2-{[2-(4-Fluorophenyl)quinolin-6-yl]sulfonyl}phenyl)ethanone

The title compound was prepared from 6-bromo-2-(4-fluorophenyl)quinoline (Example 19 Step 1) according to the methods of Example 2 Step 2 followed by Example 6, using 2'-iodoacetophenone in Step 4. $^1$H NMR (500 MHz, DMSO-d) δ 8.75 (1H, d, J 8.7 Hz), 8.70 (1H, d, J 1.7 Hz), 8.39 (2H, m), 8.34 (1H, d, J 8.7 Hz), 8.23 (1H, d, J 8.9 Hz), 8.20 (1H, d, J 7.9 Hz), 8.11 (1H, dd, J 1.9, 8.9 Hz), 7.82 (1H, t, J 7.4 Hz), 7.75 (1H, t, J 7.3 Hz), 7.68 (1H, d, J 7.4 Hz), 7.41 (2H, t, J 8.8 Hz), 2.64 (3H, s); m/z (ES$^+$) 406 [MH$^+$].

Example 33

(1S)-1-(2-{[7-(4-Fluorophenyl)-1,8-naphthyridin-3-yl]sulfonyl}phenyl)ethanol

Step 1:
6-Bromo-2-(4-fluorophenyl)-1,8-naphthyridine

A mixture of 2-amino-5-bromonicotinaldehyde [prepared by the method of Duggan et al., WO 9818461] (5.53 g, 27.5 mmol), 4-fluoroacetophenone (3.0 mL, 24.8 mmol) and 20% aqueous potassium hydroxide (3.5 mL) in ethanol (400 mL) was heated at reflux for 1 hour. The reaction mixture was allowed to stand at room temperature, the crystals formed collected under suction, washed with ethanol and dried in vacuo to afford 6-bromo-2-(4-fluorophenyl)-1,8-naphthyridine (4.86 g, 65%). $^1$H NMR (500 MHz, CDCl$_3$) δ 9.12 (1H, d, J 2.5 Hz), 8.34 (1H, d, J 2.5 Hz), 8.32-8.28 (2H, m), 8.18 (1H, d, J 8.5 Hz), 7.99 (1H, d, J 8.5 Hz), 7.25-7.19 (2H, m).

Step 2: (1S)-1-(2-{[7-(4-Fluorophenyl)-1,8-naphthyridin-3-yl]sulfonyl}phenyl)ethanol The title compound was prepared from 6-bromo-2-(4-fluorophenyl)-1,8-naphthyridine according to the methods of Example 29 Steps 3-6. $^1$H NMR (500 MHz, CDCl$_3$) δ 8.79 (1H, d, J 2.3 Hz), 8.56 (1H, s), 8.26-8.18 (4H, m), 7.91 (1H, d, J 7.8 Hz), 7.87 (1H, d, J 8.5 Hz), 7.79 (1H, t, J 7.5 Hz), 7.63 (1H, t, J 7.6 Hz), 7.25 (2H, m), 5.63 (1H, q, J 6.2 Hz), 3.47 (1H, br s), 1.51 (3H, d, J 6.2 Hz); m/z (ES$^+$) 409 [MH$^+$].

Example 34

Methyl 2-{[7-(4-fluorophenyl)-1,8-naphthyridin-3-yl]sulfonyl}benzoate

The title compound was prepared from 6-bromo-2-(4-fluorophenyl)-1,8-naphthyridine (Example 33 Step 1) according to the method of Example 30. $^1$H NMR (500 MHz, CDCl$_3$) δ 9.50 (1H, d, J 2.5 Hz), 8.90 (1H, d, J 2.5 Hz), 8.41 (1H, d, J 8.6 Hz), 8.37-8.31 (3H, m), 8.09 (1H, d, J 8.5 Hz), 7.75-7.65 (3H, m), 7.23 (2H, t, J 8.6 Hz), 3.97 (3H, s); m/z (ES$^+$) 423 [MH$^+$].

Example 35

(1S)-1-(2-{[6-(2-Fluorophenyl)-2-naphthyl]sulfonyl}phenyl)ethanol

A mixture of (1S)-1-{2-[(6-bromo-2-naphthyl)sulfonyl]phenyl}ethanol [Example 10 Step 2] (102 mg, 0.26 mmol), 2-fluorophenylboronic acid (75 mg, 0.53 mmol), palladium (II) acetate (3 mg, 0.013 mmol), tri(o-tolyl)phosphine (9 mg, 0.028 mmol), sodium carbonate (83 mg, 0.787 mmol) and water (0.5 mL) in 1,2-dimethoxyethane (3 mL) was degassed and stirred at 80° C. (oil bath temperature) under nitrogen for 16 hours. The cooled reaction mixture was diluted with ethyl acetate and filtered. The filtrate was evaporated and the residue purified by flash chromatography, eluting with 60-75% diethyl ether/isohexane, to afford the title compound as a foam (86 mg, 81%). $^1$H NMR (500 MHz, CDCl$_3$) δ 8.56 (1H, s), 8.17 (1H, dd, J 1.0, 8.0 Hz), 8.06 (2H, m), 7.98 (1H, d, J 8.6

Hz), 7.83 (1H, m), 7.77 (2H, m), 7.66 (1H, t, J 7.5 Hz), 7.54 (1H, dt, J 1.6, 7.7 Hz), 7.49 (1H, t, J 7.7 Hz), 7.42-7.38 (1H, m), 7.28 (1H, m), 7.21 (1H, m), 5.68-5.62 (1H, m), 2.51 (1H, d, J 3.2 Hz), 1.36 (3H, d, J 6.3 Hz); m/z (ES$^+$) 389 [(M-OH)$^+$].

Example 36

6-{[6-(4-Fluorophenyl)-2-naphthyl]sulfonyl}-9H-purine

A mixture of sodium 6-(4-fluorophenyl)naphthalene-2-sulfinate [prepared according to the method of Example 10(a) Steps 1-2] (104 mg, 0.34 mmol) and 6-bromopurine (70 mg, 0.35 mmol) in dimethylsulfoxide (4 mL) was stirred at 80° C. (oil bath temperature) under nitrogen for 22 hours. The cooled reaction mixture was diluted with water (20 mL), the preciptate formed collected under suction, washed with water and dried in vacuo. Purification by flash chromatography, eluting with 5% methanol in dichloromethane, gave the title compound as a white solid (33 mg, 25%). $^1$H NMR (500 MHz, DMSO-d$_6$) δ 14.06 (1H, br s), 9.04 (1H, s), 8.92 (1H, s), 8.86 (1H, s), 8.38 (1H, s), 8.35 (1H, d, J 8.7 Hz), 8.23 (1H, d, J 8.7 Hz), 8.05 (2H, m), 7.92 (2H, m), 7.38 (2H, m); m/z (ES$^+$) 405 [MH$^+$].

Example 37

2-(2-{[6-(4-Fluorophenyl)-2-naphthyl]sulfonyl}phenyl)pyrazine

Step 1: 2-(2-Iodophenyl)-pyrazine

1-Bromo-2-iodobenzene (0.32 mL, 2.4 mmol), copper(I) iodide (50 mg, 0.26 mmol) and bis(triphenylphosphine)palladium(II) chloride (88 mg, 0.12 mmol) were added to a degassed solution of 2-tributylstannylpyrazine (1.0 g, 2.4 mmol) in tetrahydrofuran (10 mL) and stirred at 90° C. under nitrogen for 22 hours. Diethyl ether was added to the cooled mixture, filtered through 'Hyflo' silica and concentrated in vacuo. Purification by flash column chromatography eluting with a 10-100% diethyl ether/isohexane gradient gave a pale yellow oil of 2-(2-iodophenyl)pyrazine (0.11 g, 16%) which contained some 2-(2-bromophenyl)pyrazine. $^1$H NMR (500 MHz, CDCl$_3$) δ 8.85 (1H, d, J=1.4 Hz), 8.71-8.65 (1H, m), 8.59 (1H, d, J=2.5 Hz), 8.00 (1H, d, J=7.9 Hz), 7.49-7.46 (2H, m), 7.19-7.11 (1H, m); m/z (ES$^+$) 283 [MH$^+$].

Step 2: 2-(2-{[6-(4-Fluorophenyl)-2-naphthyl]sulfonyl}phenyl)pyrazine

The title compound was prepared from sodium 6-(4-fluorophenyl)naphthalene-2-sulfinate (145 mg, 0.47 mmol) and 2-(2-iodophenyl)pyrazine (0.11 g, 0.46 mmol) according to the methods of Example 6 Step 4. Purification by flash column chromatography eluting with a 10-60% ethyl acetate/isohexane gradient gave 2-(2-{[6-(4-fluorophenyl)-2-naphthyl]sulfonyl}phenyl)pyrazine (79 mg, 38%). $^1$H NMR (500 MHz, CDCl$_3$) δ 8.77 (1H, d, J=1.2 Hz), 8.51 (1H, d, J=2.4 Hz), 8.44-8.38 (1H, m), 8.28-8.23 (1H, m), 8.03 (1H, s), 7.98 (1H, s), 7.87 (2H, t, J=8.8 Hz), 7.79 (1H, dd, J=1.6, 8.5 Hz), 7.74-7.62 (4H, m), 7.56 (1H, dd, J=1.7, 8.6 Hz), 7.42-7.35 (1H, m), 7.23-7.15 (2H, m); m/z (ES$^+$) 441 [MH$^+$].

Example 38

Methyl 2-{[6-(4-fluorophenyl)-2-naphthyl]sulfonyl}benzoate

The title compound was prepared from sodium 6-(4-fluorophenyl)naphthalene-2-sulfinate (2.2 g, 7.13 mmol) and methyl 2-iodobenzoate (1.06 mL, 7.0 mmol) according to the methods of Example 6 Step 4. Purification by flash column chromatography eluting with a 20-50% ethyl acetate/isohexane gradient gave methyl 2-{[6-(4-fluorophenyl)-2-naphthyl]sulfonyl}benzoate (1.7 g, 58%). $^1$H NMR (500 MHz, CDCl$_3$) δ 8.58 (1H, s), 8.25-8.16 (1H, m), 8.06 (1H, d, J=8.5 Hz), 8.01 (1H, s), 8.00-7.92 (2H, m), 7.81 (1H, dd, J=1.7, 8.5 Hz), 7.71-7.54 (5H, m), 7.23-7.13 (2H, m), 3.96 (3H, s); m/z (ES$^+$) 421 [MH$^+$].

Example 39

2-(2-{[6-(4-Fluorophenyl)-2-naphthyl]sulfonyl}phenyl)-1,3,4-oxadiazole

Hydrazine hydrate (2.25 mL, 46 mmol) was added to a solution of methyl 2-{[6-(4-fluorophenyl)-2-naphthyl]sulfonyl}benzoate (Example 38, 0.42 g, 1.0 mmol) in 1,4-dioxane (1 mL), stirred for 1 hour at room temperature then heated at 90° C. overnight. Solvent was removed in vacuo and the residue azeotroped using toluene. Triethyl orthoformate (10 mL) and a catalytic quantity of (±)-10-camphorsulfonic acid were added to the resultant crude hydrazide then stirred and heated at 90° C. overnight. Solvent was removed in vacuo, water (100 mL) added and extracted with ethyl acetate (2×75 mL). Extracts were washed with water and saturated brine then dried (MgSO$_4$), filtered and evaporated to a yellow residue. Purification by flash column chromatography eluting with a 20-60% ethyl acetate/isohexane gradient gave 2-(2-{[6-(4-fluorophenyl)-2-naphthyl]sulfonyl}phenyl)-1,3,4-oxadiazole (0.22 g, 51%). $^1$H NMR (500 MHz, d$_6$-DMSO) δ 9.46 (1H, s), 8.59 (1H, s), 8.40 (1H, dd, J=1.0, 8.0 Hz), 8.37 (1H, s), 8.30 (1H, d, J=8.7 Hz), 8.20 (1H, d, J=8.8 Hz), 8.05 (1H, dd, J=1.7, 8.6 Hz), 8.00-7.96 (1H, m), 7.93-7.91 (3H, m), 7.87-7.85 (2H, m), 7.42-7.33 (2H, m); m/z (ES$^+$) 431 [MH$^+$].

Example 40

(2-{[6-(4-Fluorophenyl)-2-naphthyl]sulfonyl}phenyl)(1H-imidazol-2-yl)methanol

Step 1: 1H-Imidazol-2-yl(2-iodophenyl)methanol n-Butyl lithium solution (2.5M in hexanes, 0.84 mL, 2.10 mmol) was added to 1-(dimethylaminomethyl)imidazole (prepared by the method detailed in JOC 1988, 53, 5685-5689; 0.25 g, 2.0 mmol) in tetrahydrofuran (8 mL) at ≦−65° C. with stirring under nitrogen. After 1 hour at this temperature a solution of 2-iodobenzaldehyde (0.50 g, 2.09 mmol) in tetrahydrofuran (1 mL) was added and the mixture allowed to return to ambient temperature overnight. Dilute hydrochloric acid (2N, 10 mL) was then added and organic solvent removed in vacuo before neutralising with sodium bicarbonate. Dichloromethane (3×30 mL) extracts were washed with saturated brine then dried (MgSO$_4$), filtered and concentrated in vacuo to give a yellow oil. Purification by flash column chromatography eluting with 50% ethyl acetate/isohexane gave a white solid of 1H-imidazol-2-yl(2-iodophenyl)methanol (0.22 g, 38%). $^1$H NMR (500 MHz, d$_6$-DMSO) δ 11.94 (1H, s), 7.80 (1H, dd, J=1.0, 7.8 Hz), 7.53 (1H, dd, J=1.7, 7.8 Hz), 7.41-7.37 (1H, m), 7.04-7.00 (2H, m), 6.74 (1H, s), 6.20 (1H, d, J=4.7 Hz), 5.83 (1H, d, J=4.7 Hz); m/z (ES$^+$) 301 [MH$^+$].

Step 2: (2-{[6-(4-Fluorophenyl)-2-naphthyl]sulfonyl}phenyl)(1H-imidazol-2-yl)methanol The title compound was prepared from sodium 6-(4-fluorophenyl)naphthalene-2-sulfinate (193 mg, 0.62 mmol) and 1H-imidazol-2-yl(2-iodophenyl)methanol (171 mg, 0.57 mmol) according to the method of Example 6 Step 4. Purification by flash column chromatography eluting with ethyl acetate gave solid (2-{[6-(4-fluorophenyl)-2-naphthyl]sulfonyl}phenyl)(1H-imidazol-2-yl)methanol (135 mg, 51%). $^1$H NMR (500 MHz, d$_6$-DMSO) δ 11.94 (1H, s), 8.54 (1H, s), 8.30 (1H, s), 8.19 (1H, d, J=8.6 Hz), 8.11 (1H, d, J=7.9 Hz), 8.07 (1H, d, J=8.7 Hz), 8.02-7.97 (1H, m), 7.94-7.86 (2H, m), 7.84 (1H, d, J=7.7 Hz), 7.78-7.67 (2H, m), 7.61-7.53 (1H, m), 7.41-7.32 (2H, m), 6.88 (1H, s), 6.84 (1H, d, J=5.2 Hz), 6.52 (1H, s), 6.12 (1H, d, J=5.2 Hz); m/z (ES$^+$) 459 [MH$^+$].

Example 41

N-(2-{[6-(4-Fluorophenyl)-2-naphthyl]sulfonyl}phenyl)-N'-methylurea

Step 1: N-(2-Iodophenyl)-N'-methylurea

A solution of methylamine in THF (2 M, 19 mL, 39 mmol) was cooled to 0° C. and 2-iodophenylisocyanate (0.68 g, 12.6 mmol) was added dropwise over 5 minutes. The solution was stirred for 30 minutes, after which it was evaporated to dryness in vacuo to yield a white solid (2.05 g) $^1$H NMR (400 MHz, d$_6$-DMSO): δ 7.81-7.77 (2H, m), 7.53 (1H, s), 7.30-7.26 (1H, m), 6.87 (1H, d, J=4.3 Hz), 6.77-6.73 (1H, m), 2.65 (3H, d, J=4.6 Hz).

Step 2: N-(2-{[6-(4-Fluorophenyl)-2-naphthyl]sulfonyl}phenyl)-N'-methylurea

Prepared according to the method of Example 6 Step 4 using N-(2-iodophenyl)-N'-methylurea and sodium 6-(4-fluorophenyl)naphthalene-2-sulfinate, to give the title compound as a white solid (81 mg). $^1$H NMR (500 MHz, d$_6$-DMSO): δ 8.81 (1H, s), 8.34 (2H, s), 8.18 (2H, dd, J=8.6, 21.9 Hz), 8.08-8.02 (2H, m), 7.97 (1H, d, J=8.3 Hz), 7.90 (2H, dd, J=5.5, 8.7 Hz), 7.84 (1H, dd, J=1.7, 8.6 Hz), 7.61-7.57 (1H, m), 7.52 (1H, s), 7.37 (2H, t, J=8.8 Hz), 7.25 (1H, t, J=7.6 Hz), 2.56 (3H, d, J=4.4 Hz); m/z (ES$^+$) 411 [MH$^+$].

Example 42

2-{[6-(4-Fluorophenyl)-2-naphthyl]sulfonyl}-1-methyl-1H-imidazole

Step 1: 2-{[6-(4-Fluorophenyl)-2-naphthyl]thio}-1-methyl-1H-imidazole

A mixture of 6-(4-fluorophenyl)-2-naphthyl trifluoromethanesulfonate (Ex 1 Step 2, 150 mg, 0.41 mmol), 1-methyl-1H-imidazole-2-thiol (47 mg, 0.41 mmol), tris(dibenzylideneacetone)dipalladium(0) (16 mg), 4,5-bis(diphenylphosphino)-9,9-dimethylxanthene (20 mg) and diisopropylethylamine (0.15 mL, 0.82 mmol) in dioxane (3 mL) was heated to 125° C. under nitrogen for 15 h. The cooled reaction mixture was poured into water and extracted with ethyl acetate (x3). The combined organic layers were washed with water and brine, dried (MgSO$_4$) and evaporated in vacuo. The residue was purified by flash column chromatography on silica, eluting with 25% ethyl acetate/isohexane, to give the title compound as an oil (125 mg). $^1$H NMR (500 MHz, CDCl$_3$): δ 7.90 (1H, s), 7.75 (2H, t, J=8.6 Hz), 7.66-7.59 (4H, m), 7.27 (2H, m), 7.15 (2H, m), 7.10 (1H, s), 3.65 (3H, s); m/z (ES$^+$) 335 [MH$^+$].

Step 2: 2-{[6-(4-Fluorophenyl)-2-naphthyl]sulfonyl}-1-methyl-1H-imidazole

2-{[6-(4-Fluorophenyl)-2-naphthyl]thio}-1-methyl-1H-imidazole (125 mg, 0.4 mmol) was dissolved in CH$_2$Cl$_2$ (1 mL) and was cooled to 0° C. 3-Chloroperbenzoic acid (224 mg, 1.0 mmol) was added and the solution stirred at ambient temperature for 1.5 h. The solution was diluted with CH$_2$Cl$_2$ (1 mL) and calcium hydroxide (277 mg, 0.6 mmol) was added. The suspension was stirred for 30 minutes before filtering through a pad of Hyflo; the liquors were evaporated in vacuo. The residue was purified by flash column chromatography on silica, eluting with 55% ethyl acetate/isohexane, to give the title compound as a white solid (67 mg). $^1$H NMR (500 MHz, d$_6$-DMSO): δ 8.74 (1H, s), 8.36 (2H, m), 8.22 (1H, d, J=8.7 Hz), 8.04 (1H, d, J=8.6 Hz), 7.93-7.91 (3H, m), 7.50 (1H, s), 7.38 (2H, t, J=8.8 Hz), 7.12 (1H, s), 3.97 (3H, s); m/z (ES$^+$) 367 [MH$^+$].

Example 43

1-(2-{[6-(4-Fluorophenyl)-2-naphthyl]sulfonyl}benzyl)-1H-1,2,4-triazole

Step 1: 1-(2-Iodobenzyl)-1H-1,2,4-triazole

To a stirring solution of 1,2,4-triazole (1.02 g, 14.8 mmol) and 2-iodobenzyl bromide (6.05 g, 20.3 mmol) in THF (10 mL) was added a solution of DBU (2.65 g, 17.4 mmol) in THF (2 mL) dropwise over a 1 hour period. The mixture was stirred at ambient temperature for 12 hours after which it was filtered. The filtrate was concentrated in vacuo and the resultant residue was dissolved in ethyl acetate. The organic layer was washed with water and brine, dried (MgSO$_4$) and evaporated in vacuo. The residue was purified by flash column chromatography on silica, eluting with 50-60% ethyl acetate/isohexane to give the title compound as a white solid (1.45 g). $^1$H NMR (360 MHz, CDCl$_3$): δ 8.15 (1H, s), 8.00 (1H, s), 7.89 (1H, d, J=7.9 Hz), 7.36 (1H, t, J=7.6 Hz), 7.13 (1H, d, J=7.7 Hz), 7.08-7.04 (1H, m), 5.43 (2H, s).

Step 2: 1-(2-{[6-(4-Fluorophenyl)-2-naphthyl]sulfonyl}benzyl)-1H-1,2,4-triazole

Prepared according to the method of Example 6 Step 4 using 1-(2-iodobenzyl)-1H-1,2,4-triazole and sodium 6-(4-fluorophenyl)naphthalene-2-sulfinate, to give the title compound as a white solid (11 mg). $^1$H NMR (500 MHz, d$_6$-DMSO): δ 8.78 (1H, s), 8.59 (1H, s), 8.37 (1H, s), 8.32 (1H, d, J=8.6 Hz), 8.25-8.19 (2H, m), 8.05 (1H, dd, J=1.7, 8.5 Hz), 7.94-7.90 (3H, m), 7.86 (1H, dd, J=1.8, 8.6 Hz), 7.71-7.65 (2H, m), 7.38 (2H, t, J=8.8 Hz), 6.88 (1H, d, J=6.8 Hz), 5.81 (2H, s); m/z (ES$^+$) 444 [MH$^+$].

Example 44

(1S)-1-(2-{[6-(4-Fluorophenyl)-2-naphthyl]sulfonyl}-3-methyl-phenyl)ethanol

Step 1: (1S)-1-(2-Iodo-3-methylphenyl)ethanol 1-(2-Iodo-3-methylphenyl)ethanone (500 mg, 1.92 mmol) (prepared according to the procedure of Buchwald, et al., *J. Am. Chem. Soc.* 1987, 109, 7137-7141) was added slowly over a period of 5 minutes to a cooled (−25° C.) solution of (−)-DIP-Chloride™ (691 mg, 2.15 mmol) in THF (2 mL). The reaction was stirred at −20° C. for 6 hours. MeOH (0.8 mL)

was added, then the reaction was warmed to ambient temperature and concentrated in vacuo. The resultant residue was taken up in ethyl acetate (1 mL) and ethanolamine (0.4 mL, 4.2 mmol) was added. As the solution stirred vigorously, a precipitate formed. The precipitate was filtered off; the liquors were diluted with hexane (1 mL) and filtered again. The liquors were concentrated in vacuo and the resultant residue was purified by flash column chromatography on silica, eluting with 10% ethyl acetate/isohexane, followed by recrystallisation with isohexane to give the title compound as a white solid (120 mg). SFC (10% MeOH, chiralpak AD-H) e.e. 100%; $^1$H NMR (400 MHz, $d_6$-DMSO): δ 7.33 (1H, dd, J=1.6, 7.3 Hz); 7.27 (1H, t, J=7.5 Hz); 7.21 (1H, dd, J=1.5, 7.2 Hz); 5.36 (1H, d, J=4.1 Hz); 4.92-4.88 (1H, m); 2.40 (3H, s); 1.26 (3H, d, J=6.3 Hz).

Step 2: (1S)-1-(2-{[6-(4-Fluorophenyl)-2-naphthyl]sulfonyl}-3-methyl-phenyl)ethanol Prepared according to the method of Example 6 Step 4 using (1S)-1-(2-iodo-3-methylphenyl)ethanol and sodium 6-(4-fluorophenyl)naphthalene-2-sulfinate to give the title compound as a white solid (58 mg). SFC (10% MeOH, chiralpak AD-H) e.e. >99%; $^1$H NMR (400 MHz, $d_6$-DMSO): δ 8.6 (1H, s), 8.35 (1H, s), 8.31 (1H, d, J=8.7 Hz), 8.17 (1H, d, J=8.7 Hz), 8.03 (1H, d, J=9.4 Hz), 7.93-7.89 (2H, m), 7.85 (1H, d, J=7.7 Hz), 7.75 (1H, m) 7.6 (1H, t, J=8.7 Hz), 7.4-7.35 (2H, t, J=7.5 Hz), 7.3 (1H, d, J=7.4 Hz) 5.9 (1H, m), 5.35 (1H, d, J=7.3 Hz), 2.5 (3H, s) 1.3 (3H, d, J=6.3 Hz); m/z (ES$^+$) 403 [(M-OH)$^+$].

Example 45

N-[(2-{[6-(4-Fluorophenyl)-2-naphthyl]sulfonyl}pyridin-3-yl)methyl]-2-methylpropane-2-sulfinamide Step 1: 2-{[6-(4-Fluorophenyl)-2-naphthyl]sulfonyl}nicotinaldehyde A suspension of 2-chloronicotinaldehyde (228 mg, 1.62 mmol) and sodium 6-(4-fluorophenyl)naphthalene-2-sulfinate (500 mg, 1.62 mmol) in DMSO (2.5 mL) was heated for 12 hours at 80° C. The reaction was poured into water (10 mL) and extracted with ethyl acetate (3×10 mL). The combined organic layers were washed with water and brine, dried (Na$_2$SO$_4$) and evaporated in vacuo. The residue was purified by flash column chromatography on silica, eluting with 35-60% ethyl acetate/isohexane, to give the title compound as solid (349 mg). $^1$H NMR (400 MHz, $d_6$-DMSO): δ 11.00 (1H, s), 8.84-8.82 (2H, m), 8.40-8.34 (3H, m), 8.25 (1H, d, J=8.7 Hz), 8.06-8.02 (2H, m), 7.94-7.84 (3H, m), 7.38 (2H, t, J=8.8 Hz).

Step 2: N-[(1E)-(2-{[6-(4-Fluorophenyl)-2-naphthyl]sulfonyl}pyridin-3-yl)methylene]-2-methylpropane-2-sulfinamide To a solution of 2-{[6-(4-fluorophenyl)-2-naphthyl]sulfonyl}nicotinaldehyde (300 mg, 0.77 mmol) in THF (1.6 mL) was added 2-methylpropane-2-sulfinamide (102 mg, 0.84 mmol) and titanium tetraethoxide (0.32 mL, 1.54 mmol). The reaction was heated for 8 hours at 80° C. The reaction mixture was poured into brine, ethyl acetate was added and the mixture stirred for 10 minutes. The organic layer was separated and washed with water and brine, filtered through Hyflo and the volatiles evaporated in vacuo to give the title compound as solid (170 mg). $^1$H NMR (400 MHz, $d_6$-DMSO): δ 9.60 (1H, s), 8.75 (1H, s), 8.72 (1H, d, J=4.6 Hz), 8.57 (1H, d, J=7.9 Hz), 8.40 (1H, s), 8.34 (1H, d, J=8.7 Hz), 8.24 (1H, d, J=8.7 Hz), 8.05 (1H, d, J=7.5 Hz), 7.93 (3H, dd, J=6.3, 8.5 Hz), 7.82 (1H, dd, J=4.6, 7.9 Hz), 7.39 (2H, t, J=8.8 Hz), 1.24 (9H, s).

Step 3: N-[(2-{[6-(4-Fluorophenyl)-2-naphthyl]sulfonyl}pyridin-3-yl)methyl]-2-methylpropane-2-sulfinamide To a solution of N-[(1E)-(2-{[6-(4-fluorophenyl)-2-naphthyl]sulfonyl}pyridin-3-yl)methylene]-2-methylpropane-2-sulfinamide (170 mg, 0.34 mmol) in MeOH (1.2 ml) and CH$_2$Cl$_2$ (2.5 ml) was added NaBH$_4$ (78 mg, 2.06 mmol). The reaction was left for 10 minutes, before addition of water (2 mL). The mixture was extracted with CH$_2$Cl$_2$ dried (Na$_2$SO$_4$) and evaporated in vacuo to give the title compound as a solid (125 mg). $^1$H NMR (400 MHz, $d_6$-DMSO): δ 8.72 (1H, s), 8.43 (1H, t, J=2.3 Hz), 8.38 (1H, s), 8.34 (1H, d, J=8.7 Hz), 8.23 (2H, dd, J=8.2, 10.2 Hz), 8.04 (1H, dd, J=1.8, 8.6 Hz), 7.95-7.91 (3H, m), 7.69 (1H, dd, J=4.6, 8.0 Hz), 7.38 (2H, t, J=8.8 Hz), 5.98 (1H, t, J=6.5 Hz), 4.88-4.78 (2H, m), 1.18 (9H, s). m/z (ES$^+$) 497 [MH$^+$].

Example 46

N'—(2-{[6-(4-Fluorophenyl)naphthalen-2-yl]sulfonyl}pyridin-3-yl)-N,N-dimethylimidoformamide Step 1: 2-{[6-(4-Fluorophenyl)naphthalen-2-yl]sulfonyl}-3-nitropyridine Sodium 6-(4-fluorophenyl)naphthalene-2-sulfinate (154 mg, 0.50 mmol), 2-chloro-3-nitropyridine (79 mg, 0.50 mmol) and DMSO (2.5 mL) were combined and the resulting solution stirred at ambient temperature for 19 hours. The solution was partitioned between EtOAc (25 mL) and water (25 mL) and the organic layer was subsequently washed with brine (15 mL), dried (MgSO$_4$), filtered and concentrated in vacuo to afford semi-pure 2-{[6-(4-fluorophenyl)naphthalen-2-yl]sulfonyl}-3-nitropyridine as a yellow solid (189 mg) which was used directly in the following step. $^1$H NMR (500 MHz, $d_6$-DMSO): δ 8.85 (1H, dd, J=1.3, 4.6 Hz), 8.75-8.73 (1H, m), 8.63 (1H, dd, J=1.3, 8.1 Hz), 8.38 (2H, t, J=7.7 Hz), 8.25 (1H, d, J=8.8 Hz), 8.06 (1H, dd, J=1.7, 8.6 Hz), 7.98-7.92 (4H, m), 7.39 (2H, t, J=8.8 Hz).

Step 2: N'—(2-{[6-(4-fluorophenyl)naphthalen-2-yl]sulfonyl}pyridin-3-yl)-N,N-dimethylimidoformamide Iron filings (127 mg, 2.27 mmol) were added to a stirred suspension of 2-{[6-(4-fluorophenyl)naphthalen-2-yl]sulfonyl}-3-nitropyridine (Step 1; 184 mg, 0.45 mmol) in AcOH (1.4 mL). The mixture was heated to 70° C. under nitrogen for 3 hours, cooled, then partitioned between saturated aqueous NaHCO$_3$ (30 mL) and EtOAc (30 mL). The organic fraction was washed with brine (15 mL), dried (MgSO$_4$), filtered and concentrated in vacuo. The resulting white solid was then dissolved in DMF (2 mL) and NaH (60% dispersion in mineral oil; 151 mg, 3.78 mmol) and methansulfonyl chloride (0.15 mL, 1.94 mmol) was added. The mixture was stirred at ambient temperature for 3 hours, then partitioned between water (25 mL) and EtOAc (25 mL). The organic fraction was washed with brine (15 mL), dried (MgSO$_4$), filtered and concentrated in vacuo. Purification of the crude material by flash column chromatography on silica yielded the title product as an off-white solid (15 mg). $^1$H NMR (500 MHz, d$_6$-DMSO): δ 8.61 (1H, s), 8.33 (1H, s), 8.26 (1H, d, J=8.6 Hz), 8.20 (1H, dd, J=1.2, 4.2 Hz), 8.11 (1H, d, J=8.7 Hz), 7.99 (1H, dd, J=1.6, 8.5 Hz), 7.91 (2H, dd, J=5.4, 8.7 Hz), 7.79 (1H, dd, J=1.6, 8.6 Hz), 7.68 (1H, s), 7.52 (1H, dd, J=4.3, 8.1 Hz), 7.47 (1H, d, J=8.1 Hz), 7.37 (2H, t, J=8.8 Hz), 2.93 (3H, s), 2.87 (3H, s); m/z (ES$^+$) 434 [MH$^+$].

Example 47

(1E)-1-(2-{[6-(4-Fluorophenyl)naphthalen-2-yl] sulfonyl}phenyl)ethanone O-methyloxime Step 1: (1E)-1-(2-Iodophenyl)ethanone O-methyloxime 1-(2-Iodophenyl)ethanone (0.14 mL, 1 mmol), sodium acetate (205 mg, 2.5 mmol) and methoxylamine hydrochloride (84 mg, 1 mmol) were combined in MeOH (5 mL) and stirred at room temperature for 1 hour, then at 75° C. for 18 hours. On cooling, the mixture was diluted with water (20 mL) and extracted with EtOAc (50 mL). The organic extracts were washed with brine (20 mL), dried (MgSO$_4$), filtered and concentrated in vacuo. Purification by column chromatography on silica afforded to presumed product (1E)-1-(2-iodophenyl)ethanone O-methyloxime as a white solid, which was used directly in the following step.

Step 2: (1E)-1-(2-{[6-(4-Fluorophenyl)naphthalen-2-yl]sulfonyl}phenyl)ethanone O-methyloxime Prepared according to the method of Example 6, Step 4 using (1E)-1-(2-iodophenyl)ethanone O-methyloxime and sodium 6-(4-fluorophenyl)naphthalene-2-sulfinate. $^1$H NMR (400 MHz, d$_6$-DMSO): δ 8.56 (1H, s), 8.35 (1H, s), 8.29-8.27 (2H, m), 8.17 (1H, d, J=8.8 Hz), 8.02 (1H, dd, J=1.7, 8.6 Hz), 7.91 (2H, dd, J=5.5, 8.8 Hz), 7.83-7.71 (3H, m), 7.44 (1H, dd, J=1.7, 7.4 Hz), 7.37 (2H, t, J=8.8 Hz), 3.56 (3H, s), 2.14 (3H, s); m/z (ES$^+$) 434 [MH$^+$].

Example 48

(2-{[6-(4-Fluorophenyl)naphthalen-2-yl]sulfonyl}-3-thienyl)methanol

Prepared according to the method of Example 6 Step 4 using (2-bromo-3-thienyl)methanol (itself prepared according to WO2004/065384A1) and sodium 6-(4-fluorophenyl) naphthalene-2-sulfinate. $^1$H NMR (400 MHz, d$_6$-DMSO): δ 8.72 (1H, s), 8.36 (2H, d, J=7.9 Hz), 8.21 (1H, d, J=8.8 Hz), 8.04 (2H, dd, J=3.2, 8.4 Hz), 7.93-7.87 (3H, m), 7.38 (2H, t, J=8.9 Hz), 7.26 (1H, d, J=5.1 Hz), 5.47 (1H, t, J=5.9 Hz), 4.70 (2H, d, J=5.9 Hz). m/z (ES$^+$) 384 [(M-OH)$^+$].

Example 49

(4-{[6-(4-Fluorophenyl)naphthalen-2-yl]sulfonyl}-3-thienyl)methanol

Step 1: 4-{[6-(4-Fluorophenyl)naphthalen-2-yl] sulfonyl}thiophene-3-carbaldehyde Prepared according to the method of Example 6 Step 4 using 4-bromothiophene-3-carbaldehyde and sodium 6-(4-fluorophenyl)naphthalene-2-sulfinate. The product 4-{[6-(4-fluorophenyl)naphthalen-2-yl]sulfonyl}thiophene-3-carbaldehyde was used directly in the following step without characterisation.

Step 2: (4-{[6-(4-Fluorophenyl)naphthalen-2-yl] sulfonyl}-3-thienyl)methanol

Sodium borohydride (21 mg, 0.53 mmol) was added to a solution of 4-{[6-(4-fluorophenyl)naphthalen-2-yl] sulfonyl}thiophene-3-carbaldehyde (42 mg, 0.11 mmol) in MeOH (5 mL) and CH$_2$Cl$_2$ (2 mL) and the mixture stirred at ambient temperature. After 40 minutes, the mixture was partitioned between water (20 mL) and CH$_2$Cl$_2$ (20 mL) and the organic fraction washed with brine (10 mL), dried (MgSO$_4$), filtered and concentrated in vacuo to afford solid material which was washed with Et$_2$O and further dried in vacuo to yield (4-{[6-(4-fluorophenyl)naphthalen-2-yl]sulfonyl}-3-thienyl)methanol as a white solid (40 mg). $^1$H NMR (400 MHz, d$_6$-DMSO): δ 8.70 (1H, s), 8.59 (1H, d, J=3.4 Hz), 8.34 (2H, t, J=6.2 Hz), 8.19 (1H, d, J=8.8 Hz), 8.03 (1H, dd, J=1.7, 8.6 Hz), 7.93-7.85 (3H, m), 7.53 (1H, d, J=3.4 Hz), 7.38 (2H, t, J=8.9 Hz), 5.31 (1H, t, J=5.6 Hz), 4.53 (2H, d, J=5.7 Hz). m/z (ES$^+$) 384 [(M-OH)$^+$].

Example 50

1-(3-{[6-(4-Fluorophenyl)naphthalen-2-yl] sulfonyl}pyridin-4-yl)cyclobutanol

Step 1: 1-(3-Bromopyridin-4-yl)cyclobutanol

3-Bromopyridine (1 g, 6.3 mmol) was added in a dropwise fashion to a stirred, −78° C. solution of lithium diisopropylamide (1.8 M commercial solution; 3.7 mL, 6.7 mmol) in THF (16 mL). After 10 minutes, cyclobutanone (0.52 mL, 7.0 mmol) was added dropwise and stirring was continued for 1 hour at −78° C., prior to warming to ambient temperature. After stirring for a further 30 minutes, the reaction was quenched by addition of saturated aqueous NH$_4$Cl (10 mL) and the mixture partitioned between EtOAc (100 mL) and water (100 mL). The organic fraction was washed with brine, dried (MgSO$_4$), filtered and concentrated in vacuo. The resulting crude product was purified by flash column chromatography on silica (eluent 50% EOAc/isohexane) to afford 1-(3-bromopyridin-4-yl)cyclobutanol as an off-white solid (412 mg). m/z (ES$^+$) 228/230 [MH$^+$].

Step 2: (1-(3-{[6-(4-Fluorophenyl)naphthalen-2-yl] sulfonyl}pyridin-4-yl)cyclobutanol Prepared according to the method of Example 6 Step 4 using 1-(3-bromopyridin-4-yl)cyclobutanol and sodium 6-(4-fluorophenyl)naphthalene-2-sulfinate. $^1$H NMR (500 MHz, CDCl$_3$): δ 8.91 (1H, s), 8.77 (1H, d, J=4.9 Hz), 8.54 (1H, s), 8.08-8.02 (3H, m), 7.88-7.82 (2H, m), 7.69 (2H, dd, J=5.2, 8.7 Hz), 7.42 (1H, d, J=5.1 Hz), 7.21 (2H, t, J=8.6 Hz), 4.74 (1H, s), 2.59-2.45 (4H, m), 2.35-2.27 (1H, m), 1.76-1.68 (1H, m). m/z (ES$^+$) 434 [MH$^+$].

Example 51

4-{[6-(4-Fluorophenyl)-2-naphthyl]sulfonyl}-1H-benzimidazole

Step 1: 1,2-Diamino-3-bromobenzene

To a stirring slurry of tin(II) chloride dihyrate (11.8 g, 52.3 mmol) in conc. hydrochloric acid (55 mL) was added 2-bromo-6-nitroaniline (2.84 g, 13.1 mmol), and the resulting mixture was stirred at room temperature for 5 minutes—an exotherm was observed. The mixture was then stirred at reflux for 30 minutes. After cooling to room temperature, the slurry was poured onto crushed ice (200 mL), and the pH was adjusted to 14 by the addition of sodium hydroxide pellets. The resulting mixture was washed with diethyl ether (5×100 mL), then the combined organic layers were dried (MgSO$_4$) and concentrated in vacuo. The crude product was purified by chromatography on a Biotage SP1 apparatus, on a 40S silica gel column, eluting with 5% to 50% ethyl acetate in dichloromethane, yielding the product as a yellow-brown oil, which solidified upon standing (2.02 g, 87%) $^1$H NMR (400 MHz, CDCl$_3$): δ 6.97 (1H, dd, J=1.4, 8.0 Hz), 6.64 (1H, dd, J=1.4, 7.8 Hz), 6.56 (1H, t, J=7.9 Hz), 3.61 (3H, s); m/z (ES$^+$) 187, 189 [MH$^+$].

Step 2: 4-Bromo-1H-benzimidazole

A solution of 1,2-diamino-3-bromobenzene (2.00 g, 10.7 mmol) in formic acid (10 mL) was stirred at 100° C. for 1 hour. The pH of the mixture was adjusted to 14 by the addition of 4 M sodium hydroxide solution, precipitating the product as a solid. This was separated by filtration, washed with water and air-dried affording the product as an off-white solid. A further crop of equally pure material precipitated from the filtrate upon standing at room temperature for a few days. Total yield=1.98 g, 94%. $^1$H NMR (500 MHz, d$_6$-DMSO): δ 12.83 (1H, s), 8.30 (1H, s), 7.58 (1H, d, J=7.9 Hz), 7.41 (1H, d, J=7.1 Hz), 7.14 (1H, t, J=7.8 Hz); m/z (ES$^+$) 197, 199 [MH$^+$].

Step 3: 4-Iodo-1H-benzimidazole

Two reactions were set up as follows: A mixture of 4-bromo-1H-benzimidazole (725 mg, 3.68 mmol), sodium iodide dihydrate (1.37 g, 7.36 mmol), copper(I) iodide (70 mg, 0.37 mmol) and N,N'-dimethylethylenediamine (78 μL, 65 mg, 0.74 mmol) in dioxane (8 mL) was irradiated at 150° C. in a microwave reactor for 2.5 hours. The two reaction mixtures were combined, diluted with water (90 mL) and conc. ammonia (20 mL), then extracted with ethyl acetate (3×50 mL). The combined organic layers were washed with water (20 mL), then with saturated sodium chloride solution (50 mL), dried (MgSO$_4$) and concentrated in vacuo. The crude product was purified by flash chromatography on silica gel, eluting with ethyl acetate, yielding the product as a yellow-white solid (1.40 g, 78%). $^1$H NMR (400 MHz, d$_6$-DMSO): δ 12.72 (1H, s), 8.28 (1H, s), 7.61-7.53 (2H, m), 7.01 (1H, t, J=7.8 Hz); m/z (ES$^+$) 245 [MH$^+$].

Step 4: 4-Iodo-1-{[2-(trimethylsilyl)ethoxy]methyl}-1H-benzimidazole

To a stirring solution of 4-iodo-1H-benzimidazole (1.00 g, 4.1 mmol) in DMF (12 mL) was added sodium hydride (180 mg of a 60% dispersion in mineral oil; 4.5 mmol), and the resulting mixture was stirred at room temperature under nitrogen for 50 minutes. 2-(Trimethylsilyl)ethoxymethyl chloride (870 μL, 4.92 mmol) was added dropwise over 5 minutes at room temperature, then the mixture was stirred overnight. Water (50 mL) was added, and the mixture was washed with ethyl acetate (3×25 mL). The combined organic layers were washed with water (2×30 mL), then with saturated sodium chloride solution (30 mL), then dried (MgSO$_4$) and concentrated in vacuo. The crude product was purified by flash chromatography on silica gel, eluting with 0 to 20% ethyl acetate in dichloromethane, affording the product as a white solid (1.20 g, 78%). $^1$H NMR (400 MHz, CDCl$_3$): δ 8.05 (1H, s), 7.74 (1H, dd, J=0.6, 7.5 Hz), 7.52 (1H, t, J=4.2 Hz), 7.09 (1H, t, J=7.9 Hz), 5.51 (2H, s), 3.50 (2H, t, J=8.2 Hz), 0.90 (2H, dd, J=8.3, 16.4 Hz), −0.05 (9H, s); m/z (ES$^+$) 375 [MH$^+$].

Step 5: 4-{[6-(4-Fluorophenyl)-2-naphthyl]sulfonyl}-1-{[2-(trimethylsilyl)ethoxy]methyl}-1H-benzimidazole Prepared according to the method of Example 6 Step 4 using 4-iodo-1-{[2-(trimethylsilyl)ethoxy]methyl}-1H-benzimidazole (0.46 g, 1.23 mmol) and sodium 6-(4-fluorophenyl)naphthalene-2-sulfinate (0.42 g, 1.36 mmol), to give the title compound as a colourless solid (260 mg, 39%). $^1$H NMR (500 MHz, CDCl$_3$): δ 8.92 (1H, s), 8.21 (1H, dd, J=1.4, 8.6 Hz), 8.16 (1H, d, J=7.7 Hz), 8.07 (2H, d, J=9.9 Hz), 7.96 (1H, s), 7.91 (1H, d, J=8.7 Hz), 7.77 (2H, d, J=7.3 Hz), 7.64 (2H, dd, J=5.3, 8.5 Hz), 7.47 (1H, t, J=7.9 Hz), 7.17 (2H, t, J=8.6 Hz), 5.51 (2H, s), 4.12 (2H, q, J=7.1 Hz), 3.47 (2H, t, J=8.1 Hz), 2.04 (3H, s), 1.26 (3H, t, J=7.1 Hz), 0.86 (2H, t, J=8.1 Hz), −0.08 (9H, s); m/z (ES$^+$) 534 [MH$^+$].

Step 6: 4-{[6-(4-Fluorophenyl)-2-naphthyl]sulfonyl}-1H-benzimidazole

To a stirring solution of 4-{[6-(4-fluorophenyl)-2-naphthyl]sulfonyl}-1-{[2-(trimethylsilyl)ethoxy]methyl}-1H-benzimidazole (260 mg, 0.49 mmol) in THF (5 mL) was added tetrabutylammonium fluoride (0.60 mL of 1 M solution in THF; 0.6 mmol), and the resulting mixture was heated at reflux for 5 hours. The mixture was allowed to cool to room temperature, then was diluted with water (100 mL) and washed with ethyl acetate (2×50 mL), The combined organic layers were washed with water, then with saturated sodium chloride solution, were dried (MgSO$_4$) and concentrated in vacuo. The crude product was purified by flash chromatography on silica gel, eluting first with 1:1 ethyl acetate:isohexane, then with 100% ethyl acetate. The resulting material was purified further by flash chromatography on silica gel, eluting with 50% to 70% ethyl acetate in isohexane, and the resulting material was triturated using a 1:1 mixture of diethyl ether and isohexane, to afford the product as a white amorphous solid (85 mg, 43%). $^1$H NMR (500 MHz, d$_6$-DMSO): δ 12.96 (1H, s), 8.89 (1H, s), 8.38 (1H, s), 8.30 (1H, s), 8.26 (1H, d, J=8.6 Hz), 8.14-8.08 (2H, m), 8.00 (1H, d, J=8.6 Hz), 7.95 (2H, t, J=6.8 Hz), 7.88 (2H, dd, J=5.4, 8.7 Hz), 7.45 (1H, t, J=7.9 Hz), 7.36 (2H, t, J=8.8 Hz); m/z (ES$^+$) 403 [MH$^+$].

Example 52

(1S)-1-(2-{[6-(5-Fluoropyridin-2-yl)-2-naphthyl]sulfonyl}phenyl) ethanol

Step 1: (1S)-1-(2-{[6-(4,4,5,5-Tetramethyl-1,3,2-dioxaborolan-2-yl)-2-naphthyl]sulfonyl}phenyl)ethanol A mixture of (1S)-1-{2-[(6-bromo-2-naphthyl)sulfonyl]phenyl}ethanol (Example 10 Step 2) (527 mg, 1.35 mmol), potassium acetate (268 mg, 2.73 mmol), bis(pinacolato)diboron (396 mg, 1.56 mmol) and DMSO (0.1 mL) in dioxane (5 mL) was degassed by bubbling nitrogen through for 10 minutes. 1,1'-Bis(diphenylphosphino)ferrocene]dichloropalladium(II) complex with dichloromethane (38 mg, 47 μmol) was added, the mixture was degassed as before for 5 minutes, then was stirred at reflux under nitrogen for 1 hour. The solvent was removed in vacuo, and the crude product was taken up in ice cold 2 M sodium hydroxide solution (10 mL) and stirred for 30 minutes at 0° C. The resulting slurry was filtered, and the filtrate was washed with diethyl ether (2×5 mL). The pH of the aqueous phase was adjusted to 7 by the addition of conc. hydrochloric acid. The mixture was washed with diethyl ether (2×10 mL), then these combined organic layers were dried (MgSO$_4$) and concentrated in vacuo, to afford the product as a brown solid (188 mg, 32%). $^1$H NMR (400 MHz, CDCl$_3$): δ 8.51 (1H, s), 8.39 (1H, s), 8.17 (1H, dd, J=1.2, 8.0 Hz), 7.99-7.95 (3H, m), 7.76-7.72 (2H, m), 7.67-7.63 (1H, m), 7.51-7.47 (1H, m), 5.65-5.59 (1H, m), 2.48 (1H, d, J=3.1 Hz), 1.39 (12H, s), 1.30 (3H, d, J=6.4 Hz).

Step 2: (1S)-1-(2-{[6-(5-Fluoropyridin-2-yl)-2-naphthyl]sulfonyl}phenyl)ethanol

A mixture of 2-bromo-5-fluoropyridine (38 mg, 0.22 mmol), (1S)-1-(2-{[6-(4,4,5,5-tetramethyl-1,3,2-dioxaborolan-2-yl)-2-naphthyl]sulfonyl}phenyl)ethanol (96 mg, 0.22 mmol), palladium(II) acetate (2.6 mg, 11 µmol), tri(o-tolyl)phosphine (5.2 mg, 17 µmol) and sodium carbonate (51 mg, 0.48 mmol) in DME (2 mL) and water (0.3 mL) was degassed by bubbling nitrogen through for 5 minutes, then was heated at reflux under nitrogen for 3 hours. The slurry was filtered, and the filtrate was washed with saturated sodium hydrogen carbonate solution (10 mL), with saturated sodium chloride solution (10 mL), dried (MgSO$_4$) and concentrated in vacuo. The crude product was purified by flash chromatography on silica gel, eluting with 40% ethyl acetate in isohexane, then further purified by preparative TLC on silica gel, eluting with 50% ethyl acetate in isohexane. The product was isolated as a colourless solid, which solidified upon trituration with isohexane (13 mg, 15%). $^1$H NMR (400 MHz, CDCl$_3$): δ 8.61 (1H, d, J=2.7 Hz), 8.55 (1H, s), 8.48 (1H, s), 8.21 (2H, dd, J=8.7, 21.9 Hz), 8.06 (2H, dd, J=8.7, 22.5 Hz), 7.90 (1H, dd, J=4.1, 8.7 Hz), 7.77 (2H, d, J=7.6 Hz), 7.66 (1H, t, J=7.5 Hz), 7.57-7.49 (2H, m), 5.65 (1H, m), 2.48 (1H, s), 1.34 (3H, d, J=6.4 Hz). m/z (ES$^+$) 408 [MH$^+$].

Examples 53(a)-(kkk)

Using analogous procedures, the following were also prepared:

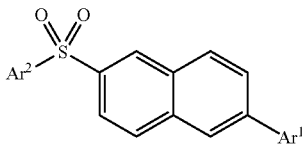

| Ex. | Ar$^1$ | Ar$^2$ | m/z (ES$^+$) (M + H)$^+$ |
|---|---|---|---|
| a | 4-fluorophenyl | pyridin-3-yl | 364 |
| b | 4-fluorophenyl | 4-(hydroxymethyl)pyridin-3-yl | 394 |
| c | 4-fluorophenyl | 2-acetylpyridin-3-yl | 406 |
| d | 4-fluorophenyl | 4-[(1R,S)-1-hydroxyethyl]pyridin-3-yl | 408 |
| e | 4-fluorophenyl | 2-[(methylsulfonyl)amino]phenyl | 456 |
| f | 4-fluorophenyl | 2-[(aminocarbonyl)amino]phenyl | 421 |
| g | 4-fluorophenyl | 2-[(dimethylaminocarbonyl)amino]phenyl | 449 |

-continued

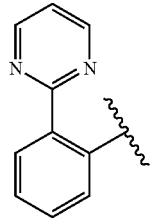

| Ex. | Ar$^1$ | Ar$^2$ | m/z (ES$^+$) (M + H)$^+$ |
|---|---|---|---|
| h | phenyl | 2-(1H-imidazol-2-yl)phenyl | 411 |
| i | 4-fluorophenyl | 2-[(1R)-1-hydroxyethyl]pyridin-3-yl | 408 |
| j | 4-fluorophenyl | 2-[(1S)-1-hydroxyethyl]pyridin-3-yl | 408 |
| k | 4-fluorophenyl | thiophen-2-yl | 369 |
| l | 4-fluorophenyl | 1-(2-hydroxyethyl)-1H-imidazol-2-yl | 397 |
| m | 4-fluorophenyl | 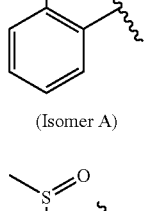 | 441 |
| n | 4-fluorophenyl | 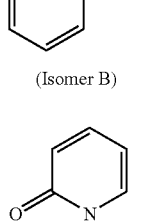<br>(Isomer A) | 425 |
| o | 4-fluorophenyl | (Isomer B) | 425 |
| p | 4-fluorophenyl | 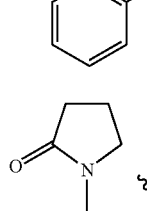 | 455 |
| q | 4-fluorophenyl | | 446 |

-continued
| | | | m/z (ES+) (M + H)+ |
|---|---|---|---|
| Ex. | Ar¹ | Ar² | |
| r | 4-fluorophenyl | 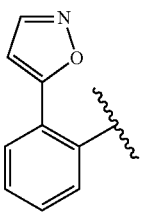 | 430 |
| s | 4-fluorophenyl | 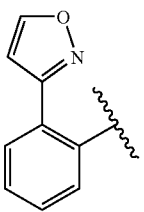 | 430 |
| t | 4-fluorophenyl | 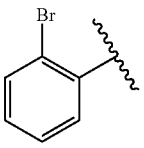 | 441/443 |
| u | 4-fluorophenyl | 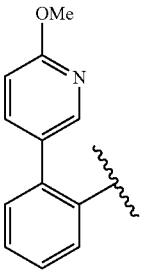 | 470 |
| v | 4-fluorophenyl | 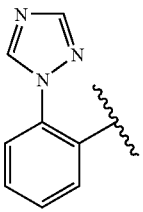 | 430 |
| w | 4-fluorophenyl | 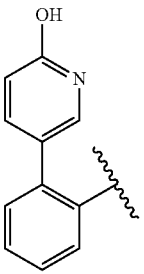 | 456 |
-continued
| | | | m/z (ES+) (M + H)+ |
|---|---|---|---|
| Ex. | Ar¹ | Ar² | |
| x | 4-fluorophenyl | 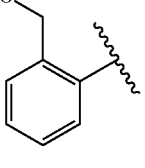 | 393 |
| y | 2,4-difluorophenyl | 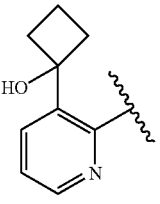 | 434 (M − OH)+ |
| z | 2,4-difluorophenyl | 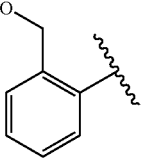 | 411 |
| aa | 4-fluorophenyl | 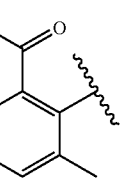 | 419 |
| bb | 4-fluorophenyl | 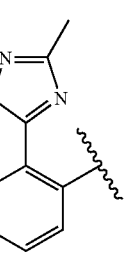 | 445 |
| cc | 2-chlorophenyl | 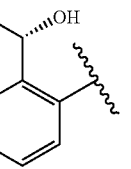 | 405 (M − OH)+ |
| dd | 4-fluoro-2-methylphenyl | 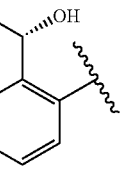 | 403 (M − OH)+ |

-continued
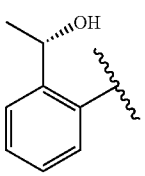
| Ex. | Ar¹ | Ar² | m/z (ES⁺) (M + H)⁺ |
|---|---|---|---|
| ee | thien-2-yl | 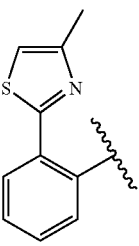 | 377 (M − OH)⁺ |
| ff | phenyl | 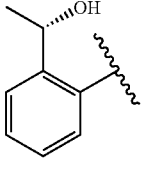 | 371 (M − OH)⁺ |
| gg | 4-fluorophenyl | 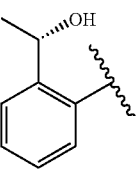 | 445 |
| hh | 4-fluorophenyl | 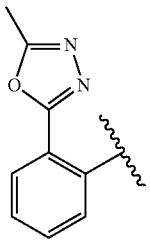 | 444 |
| ii | 4-fluorophenyl | 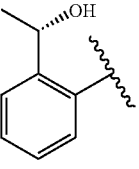 | 463 |
| jj | 4-fluorophenyl | 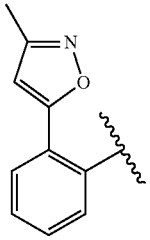 | 444 |
| kk | 4-fluorophenyl | 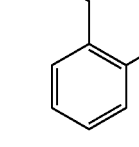 | 460 |
| ll | 2-fluoro-4-methylphenyl | 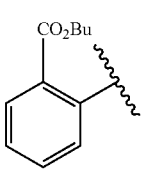 | 403 (M − OH)⁺ |
| mm | 4-methylphenyl | 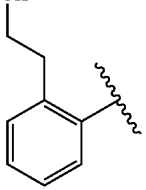 | 385 (M − OH)⁺ |
| nn | 4-fluorophenyl | 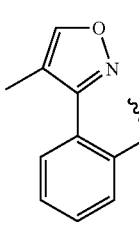 | 435 |
| oo | 4-fluorophenyl | 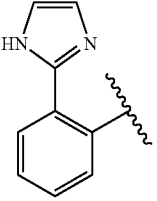 | 407 |
| pp | 4-fluorophenyl |  | 429 |

-continued

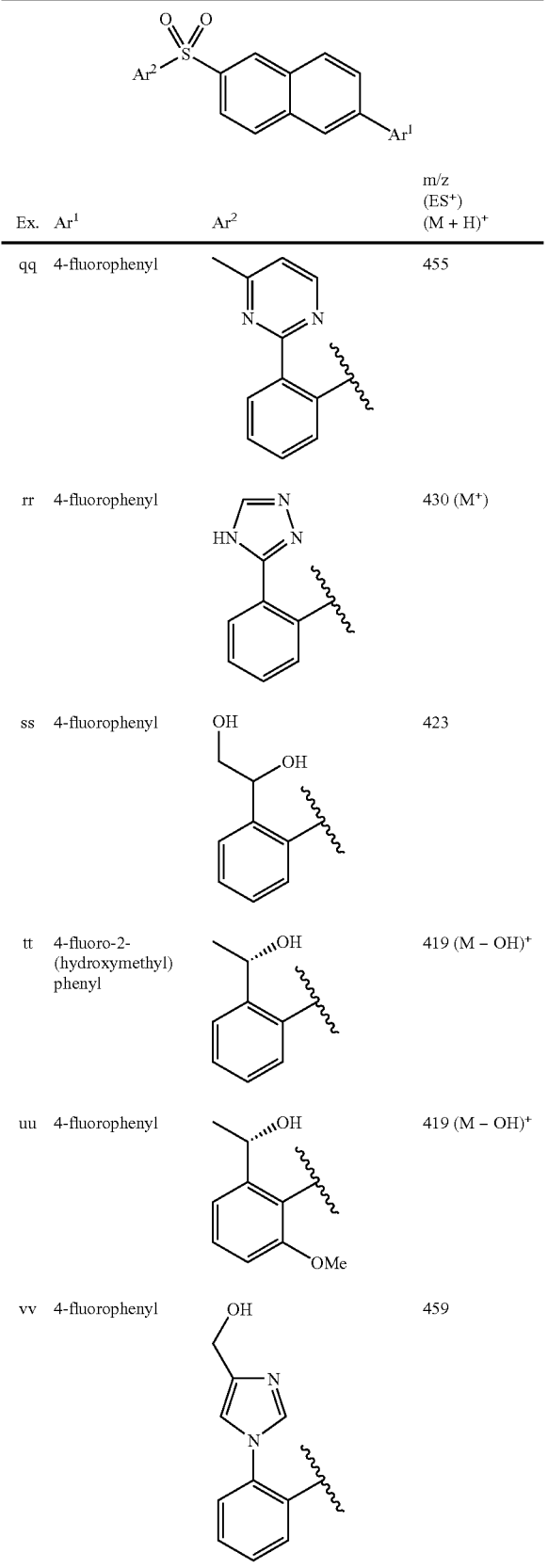

| Ex. | Ar¹ | Ar² | m/z (ES⁺) (M + H)⁺ |
|---|---|---|---|
| qq | 4-fluorophenyl | 4-methyl-pyrimidin-2-yl-phenyl | 455 |
| rr | 4-fluorophenyl | 1H-1,2,4-triazol-3-yl-phenyl | 430 (M⁺) |
| ss | 4-fluorophenyl | 1,2-dihydroxyethyl-phenyl | 423 |
| tt | 4-fluoro-2-(hydroxymethyl)phenyl | 1-hydroxyethyl-phenyl | 419 (M − OH)⁺ |
| uu | 4-fluorophenyl | 1-hydroxyethyl-3-methoxyphenyl | 419 (M − OH)⁺ |
| vv | 4-fluorophenyl | (hydroxymethyl)imidazolyl | 459 |

-continued

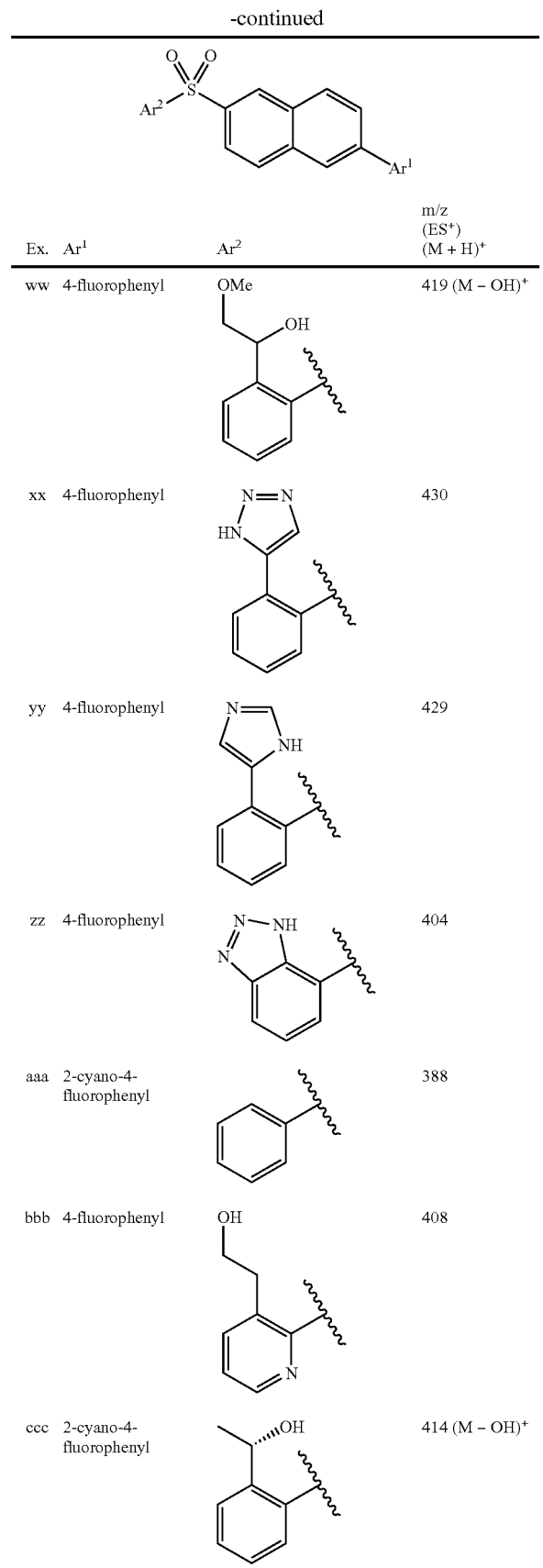

| Ex. | Ar¹ | Ar² | m/z (ES⁺) (M + H)⁺ |
|---|---|---|---|
| ww | 4-fluorophenyl | 2-methoxy-1-hydroxyethyl-phenyl | 419 (M − OH)⁺ |
| xx | 4-fluorophenyl | 1H-1,2,3-triazol-4-yl-phenyl | 430 |
| yy | 4-fluorophenyl | 1H-imidazol-5-yl-phenyl | 429 |
| zz | 4-fluorophenyl | 1H-benzotriazol-7-yl | 404 |
| aaa | 2-cyano-4-fluorophenyl | phenyl | 388 |
| bbb | 4-fluorophenyl | 2-hydroxyethyl-pyridinyl | 408 |
| ccc | 2-cyano-4-fluorophenyl | 1-hydroxyethyl-phenyl | 414 (M − OH)⁺ |

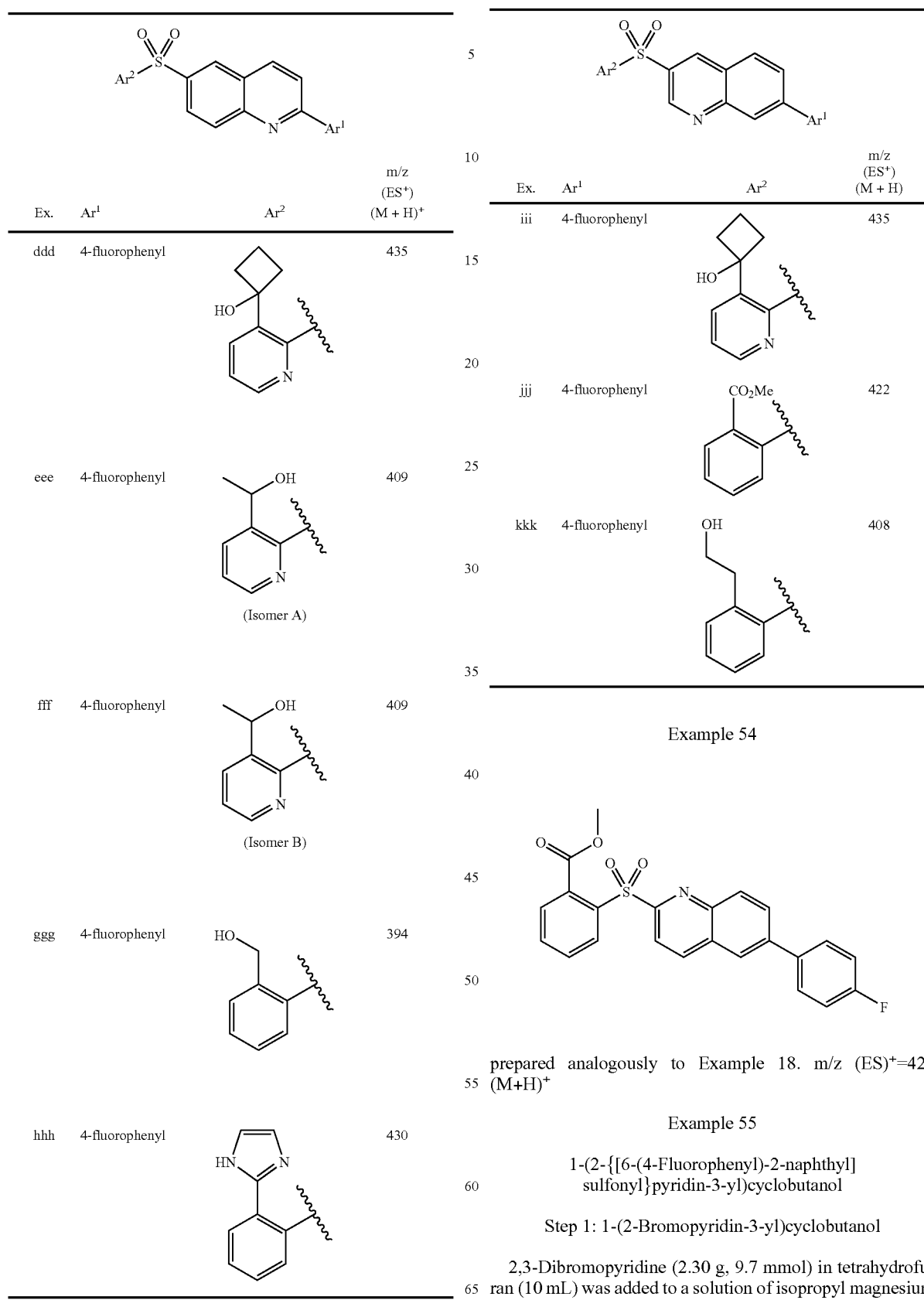

Example 54 prepared analogously to Example 18. m/z (ES)$^+$=422 (M+H)$^+$

Example 55

1-(2-{[6-(4-Fluorophenyl)-2-naphthyl]sulfonyl}pyridin-3-yl)cyclobutanol

Step 1: 1-(2-Bromopyridin-3-yl)cyclobutanol 2,3-Dibromopyridine (2.30 g, 9.7 mmol) in tetrahydrofuran (10 mL) was added to a solution of isopropyl magnesium chloride/lithium chloride (1M in tetrahydrofuran, 10 mL, prepared according to the method of Krasovskiy and Knochel, Angew. Chem. Int. Ed. 2004, 43, 3333-3336) at approximately −15° C. under nitrogen. This mixture was cooled to −78° C. and cyclobutanone (0.74 mL, 9.9 mmol) added. It was stirred for 1 hour before allowing to warm to 0° C. for a further 1 hour then quenched with saturated ammonium chloride solution. Water (150 mL) was added and extracted with diethyl ether (2×75 mL). These extracts were washed with water and brine then dried (MgSO$_4$), filtered and the solvent removed in vacuo. Purification by flash column chromatography eluting with a 0-10% diethyl ether/dichloromethane gradient gave 1-(2-bromopyridin-3-yl)cyclobutanol (0.57 g, 26%). $^1$H NMR (400 MHz, CDCl$_3$) δ 8.28 (1H, dd, J=1.9, 4.7 Hz), 7.68 (1H, dd, J=1.9, 7.6 Hz), 7.30-7.26 (1H, m), 3.00 (1H, s), 2.70-2.60 (2H, m), 2.55-2.47 (2H, m), 2.30-2.16 (1H, m), 1.77-1.65 (1H, m); m/z (ES$^+$) 228, 230 [MH$^+$].

Step 2: 1-(2-{[6-(4-Fluorophenyl)-2-naphthyl]sulfonyl}pyridin-3-yl)cyclobutanol

The title compound was prepared from sodium 6-(4-fluorophenyl)naphthalene-2-sulfinate (340 mg, 1.1 mmol) and 1-(2-bromopyridin-3-yl)cyclobutanol (228 mg, 1.0 mmol) according to the method of Example 6 Step 4. Purification by flash column chromatography eluting with a 0-10% diethyl ether/dichloromethane gradient gave 1-(2-{[6-(4-fluorophenyl)-2-naphthyl]sulfonyl}pyridin-3-yl)cyclobutanol (200 mg, 46%). $^1$H NMR (500 MHz, CDCl$_3$) δ 8.61 (1H, s), 8.29 (1H, d, J=2.2 Hz), 8.10-8.04 (2H, m), 8.01 (1H, d, J=8.7 Hz), 7.95 (1H, dd, J=1.6, 8.6 Hz), 7.88-7.81 (2H, m), 7.73-7.64 (2H, m), 7.40 (1H, dd, J=4.5, 7.8 Hz), 7.23-7.15 (2H, m), 5.01 (1H, s), 2.78-2.68 (4H, m), 2.42-2.34 (1H, m), 1.86-1.78 (1H, m); m/z (ES$^+$) 434 [MH$^+$].

Example 56

2-{[6-(4-Fluorophenyl)-2-naphthyl]sulfonyl}pyridine

The title compound was prepared from sodium 6-(4-fluorophenyl)naphthalene-2-sulfinate (250 mg, 0.81 mmol) and 2-bromopyridine (76 μL, 0.79 mmol) according to the method of Example 6 Step 4. Purification by flash column chromatography eluting with a 20-40% ethyl acetate/isohexane gradient gave 2-{[6-(4-fluorophenyl)-2-naphthyl]sulfonyl}pyridine (0.10 g, 34%). $^1$H NMR (400 MHz, CDCl$_3$) δ 8.70 (1H, s), 8.68-8.65 (1H, m), 8.33-8.22 (1H, m), 8.07 (1H, d, J=8.6 Hz), 8.04-7.92 (4H, m), 7.82 (1H, dd, J=1.8, 8.6 Hz), 7.69-7.65 (2H, m), 7.46-7.44 (1H, m), 7.22-7.16 (2H, m); m/z (ES$^+$) 364 [MH$^+$].

Example 57

2-{[6-(4-Fluorophenyl)-2-naphthyl]sulfonyl}pyridine 1-oxide

The title compound was prepared from 2-{[6-(4-fluorophenyl)-2-naphthyl]sulfonyl}pyridine (Example 56) according to the method of Example 31). Purification by flash column chromatography eluting with 50% ethyl acetate/isohexane gave 2-{[6-(4-fluorophenyl)-2-naphthyl]sulfonyl}pyridine 1-oxide (12 mg, 16%). $^1$H NMR (500 MHz, CDCl$_3$) δ 8.78 (1H, s), 8.38-8.36 (1H, m), 8.09-8.07 (3H, m), 8.03 (1H, s), 7.99 (1H, d, J=8.8 Hz), 7.81 (1H, dd, J=1.7, 8.5 Hz), 7.71-7.63 (2H, m), 7.46-7.42 (2H, m), 7.21-7.17 (2H, m); m/z (ES$^+$) 380 [MH$^+$].

Example 58

1-(2-{[6-(4-Fluorophenyl)-2-naphthyl]sulfonyl}phenyl)-1H-imidazole

Step 1: 2-(4-Fluorophenyl)-6-[(2-fluorophenyl)sulfonyl]naphthalene

The title compound was prepared from sodium 6-(4-fluorophenyl)naphthalene-2-sulfinate (2.2 g, 7.13 mmol) and 1-fluoro-2-iodobenzene (820 μL, 7.03 mmol) according to the method of Example 6 Step 4. Purification by flash column chromatography eluting with 60% dichloromethane/isohexane gave 2-(4-fluorophenyl)-6-[(2-fluorophenyl)sulfonyl]naphthalene (0.80 g, 30%). $^1$H NMR (500 MHz, CDCl$_3$) δ 8.66 (1H, s), 8.20-8.18 (1H, m), 8.07 (1H, d, J=8.5 Hz), 8.03 (1H, s), 7.98 (1H, d, J=8.7 Hz), 7.94 (1H, d, J=8.7 Hz), 7.83 (1H, dd, J=1.7, 8.5 Hz), 7.71-7.62 (2H, m), 7.60-7.56 (1H, m), 7.38-7.30 (1H, m), 7.21-7.17 (2H, m), 7.14-7.05 (1H, m).

Step 2: 1-(2-{[6-(4-Fluorophenyl)-2-naphthyl]sulfonyl}phenyl)-1H-imidazole

A mixture of 2-(4-fluorophenyl)-6-[(2-fluorophenyl)sulfonyl]naphthalene (110 mg, 0.29 mmol), imidazole (30 mg, 0.44 mmol), potassium carbonate (100 mg, 0.72 mmol) and dimethyl sulfoxide (1.5 mL) was reacted in a microwave at 150° C. for 20 minutes. The mixture was poured into water (100 mL) and extracted with ethyl acetate (2×50 mL). These extracts were washed with water and saturated brine then dried (MgSO$_4$), filtered and solvent removed in vacuo. Purification by flash column chromatography eluting with 40% ethyl acetate/isohexane then 80% ethyl acetate/isohexane gave 1-(2-{[6-(4-fluorophenyl)-2-naphthyl]sulfonyl}phenyl)-1H-imidazole (104 mg, 84%). $^1$H NMR (500 MHz, CDCl$_3$) δ 8.55 (1H, dd, J=1.7, 7.8 Hz), 7.96 (1H, s), 7.91 (1H, d, J=8.6 Hz), 7.89 (1H, s), 7.83 (1H, d, J=8.7 Hz), 7.80 (1H, dd, J=1.7, 8.5 Hz), 7.75-7.65 (4H, m), 7.42 (1H, dd, J=1.8, 8.6 Hz), 7.29 (1H, s), 7.23-7.17 (3H, m), 6.97 (1H, s), 6.75 (1H, s); m/z (ES$^+$) 429 [MH$^+$].

Example 59

{5-Fluoro-2-[6-(phenylsulfonyl)-2-naphthyl]phenyl}methanol

Step 1: 6-(2-Cyano-4-fluorophenyl)-2-naphthyl trifluoromethanesulfonate

A mixture of 6-bromo-2-naphthol (12.0 g, 52.2 mmol), 5-fluoro-2-(4,4,5,5-tetramethyl-[1,3,2]dioxaborolan-2-yl)benzonitrile (16.7 g, 67.6 mmol, prepared according to the method disclosed in patent WO/2003099816), sodium carbonate solution (2M, 75 mL) and tetrakis(triphenylphosphine)palladium (0) (1.2 g, 1.0 mmol) in 1,4-dioxane (360 mL) was heated at 80° C. for 17 hours. It was allowed to cool then poured into dilute hydrochloric acid (1 M, 360 mL) and extracted with ethyl acetate (3×200 mL). These extracts were washed with water and brine then dried (MgSO$_4$), filtered and the solution concentrated in vacuo to a volume of ~100 mL. Solid was filtered off and sucked dry to give 5-fluoro-2-(6-hydroxy-2-naphthyl)benzamide as a white solid. This solid (6.3 g, 22.4 mmol) was suspended in dichloromethane (130 mL)/pyridine (11 mL) at 0° C. under nitrogen, and trifluoromethane sulfonic anhydride (11 mL, 65.5 mmol) added gradually over 40 minutes before leaving overnight to return to ambient temperature. Solvent was removed in vacuo, water (400 mL) added and extracted into ethyl acetate (2×300 mL). These extracts were washed with water and brine then dried (MgSO$_4$), filtered and solvent removed in vacuo. Purification by flash column chromatography eluting with 10% ethyl acetate/isohexane gave 6-(2-cyano-4-fluorophenyl)-2-naphthyl trifluoromethanesulfonate (8.0 g, 38%). $^1$H NMR (500 MHz, CDCl$_3$) δ 8.06 (1H, s), 8.01 (2H, dd, J=4.0, 9.0 Hz), 7.82 (1H, d, J=2.3 Hz), 7.73 (1H, dd, J=1.7, 8.5 Hz), 7.60 (1H, dd, J=5.2, 8.6 Hz), 7.53 (1H, dd, J=2.6, 7.9 Hz), 7.47-7.41 (2H, m).

Step 2: 5-Fluoro-2-[6-(phenylsulfonyl)-2-naphthyl]benzonitrile

A mixture of 6-(2-cyano-4-fluorophenyl)-2-naphthyl trifluoromethanesulfonate (0.65 g, 1.65 mmol), sodium benzene sulfinate (0.33 g, 1.97 mmol), cesium carbonate (0.81 g, 2.48 mmol), tris(dibenzylideneacetone)dipalladium(0) (38 mg, 0.04 mmol), 4,5-bis(diphenylphosphino)-9,9-dimethylxanthene (49 mg, 0.08 mmol) and tetrabutylammonium chloride (0.55 g, 1.98 mmol) in toluene (15 mL) was heated at 120° C. under nitrogen for 4 hours. It was allowed to cool, poured into water (150 mL) and extracted with ethyl acetate (2×100 mL). These extracts were washed with water and brine then dried (MgSO$_4$), filtered and solvent removed in vacuo. Purification by flash column chromatography eluting with 20% ethyl acetate/isohexane then 40% ethyl acetate/isohexane gave 5-fluoro-2-[6-(phenylsulfonyl)-2-naphthyl]benzonitrile (150 mg, 23%). $^1$H NMR (500 MHz, d$_6$-DMSO) δ 8.82 (1H, s), 8.38 (1H, d, J=8.5 Hz), 8.26 (1H, s), 8.23 (1H, d, J=8.7 Hz), 8.05-8.03 (3H, m), 7.98 (1H, d, J=8.6 Hz), 7.88 (1H, d, J=8.5 Hz), 7.81-7.63 (5H, m); m/z (ES$^+$) 388 [MH$^+$].

Step 3: {5-Fluoro-2-[6-(phenylsulfonyl)-2-naphthyl]phenyl}methanol

A solution of diisobutylaluminium hydride (1M in dichloromethane, 700 μL, 0.70 mmol) was added to 5-fluoro-2-[6-(phenylsulfonyl)-2-naphthyl]benzonitrile (66 mg, 0.17 mmol) in dichloromethane (2 mL) at −78° C. under nitrogen and allowed to warm to 0° C. during 2 hours. It was quenched with ammonium chloride (3 mL), diluted with water (75 mL) and extracted into ethyl acetate (2×50 mL). These extracts were washed with water and brine then dried (MgSO$_4$), filtered and solvent removed in vacuo to give the crude aldehyde as a foam. This foam (67 mg, 0.17 mmol) was suspended in methanol (4 mL) at 0° C. under nitrogen and sodium borohydride (35 mg, 0.92 mmol) added. It was stirred at this temperature for 30 minutes then allowed to return to ambient temperature over 30 minutes. Water (100 mL) was added and the mixture extracted with ethyl acetate (3×30 mL). These extracts were washed with water and brine then dried (MgSO$_4$), filtered and solvent removed in vacuo. Purification by flash column chromatography eluting with a 10-40% ethyl acetate/isohexane gradient gave {5-fluoro-2-[6-(phenylsulfonyl)-2-naphthyl]phenyl}methanol (31 mg, 46%). $^1$H NMR (500 MHz, CDCl$_3$) δ 8.62 (1H, s), 8.03-8.01 (3H, m), 7.94 (1H, d, J=8.6 Hz), 7.90 (1H, dd, J=1.7, 8.7 Hz), 7.82 (1H, s), 7.60-7.50 (4H, m), 7.35 (1H, dd, J=2.5, 9.6 Hz), 7.29 (1H, dd, J=5.6, 8.4 Hz), 7.11-7.05 (1H, m), 4.60 (2H, d, J=5.1 Hz), 1.67 (1H, t, J=5.5 Hz); m/z (ES$^+$) 393 [MH$^+$].

The invention claimed is:

1. A compound of the formula I:

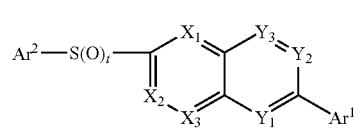

wherein:

t is 2;

each of $X_1$, $X_3$, and $Y_1$ represents CH or N and each of $X_2$, $Y_2$, and $Y_3$ represents CH, provided that $X_1$ and $X_3$ do not both represent N and provided that $X_1$ and $Y_1$ do not both represent N;

Ar$^1$ represents phenyl, said phenyl bearing 0 to 3 substituents selected from halogen, CN, CF$_3$, OCF$_3$, C$_{1-6}$alkyl, OH, C$_{1-6}$alkoxy or hydroxyC$_{1-6}$alkyl;

Ar$^2$ represents phenyl, pyridyl or thienyl, said phenyl, pyridyl or thienyl bearing 0 to 3 substituents selected from halogen, CN, nitro, R$^a$, OR$^a$, SR$^a$, SOR$^a$, SO$_2$R$^a$, SO$_2$NR$^a$R$^b$, (CH$_2$)$_x$NR$^a$R$^b$, (CH$_2$)$_x$NR$^a$COR$^b$, (CH$_2$)$_x$NR$^a$CO$_2$R$^b$, (CH$_2$)$_x$NR$^a$CONR$^a$R$^b$ (CH$_2$)$_x$NR$^a$SOR$^b$, (CH$_2$)$_x$NR$^a$SO$_2$R$^b$, (CH$_2$)$_x$NR$^a$SO$_2$NR$^a$R$^b$, (CH$_2$)$_x$COR$^a$, (CH$_2$)$_x$CO$_2$R$^a$, (CH$_2$)$_x$CONR$^a$R$^b$, N=CHN(CH$_3$)$_2$ or (CH$_2$)$_x$CR$^a$=NOR$^b$, where x is 0 or 1, or said phenyl, pyridyl or thienyl may be substituted with (CH$_2$)$_x$Ar$^3$, COAr$^3$ or CH(OH)Ar$^3$ where Ar$^3$ represents a five- or six-membered heteroaromatic ring optionally bearing up to 2 substituents selected from halogen, CN, CF$_3$, OH, C$_{1-6}$alkyl, C$_{1-6}$alkoxy, C$_{1-6}$alkylthio, amino, C$_{1-6}$alkylamino or di(C$_{1-6}$)alkylamino;

R$^a$ and R$^b$ independently represent H or a hydrocarbon group of up to 7 carbon atoms which is optionally substituted with up to 3 halogen atoms or with up to 2 substituents selected from CN, OH, C$_{1-4}$alkoxy, C$_{1-4}$alkylthio, amino, C$_{1-4}$alkylamino and di(C$_{1-4}$)alkylamino; or R$^a$ or R$^b$, when linked through a nitrogen atom, together represent the residue of a heterocyclic ring of 4, 5 or 6 members, optionally bearing up to 3 substituents selected from halogen, CN, CF$_3$, oxo, OH, C$_{1-4}$alkyl or C$_{1-4}$alkoxy; or two R$^a$ groups, when attached to adjacent carbon atoms of Ar$^2$, may form a fused ring of 5 or 6 members, 0-3 of which are selected from N, O or S while the remainder are carbon, said ring optionally bearing up to 3 substituents selected from halogen CN, CF$_3$, oxo, OH, C$_{1-4}$alkyl or C$_{1-4}$alkoxy;

and wherein any nitrogen atom forming part of a heteroaromatic ring may be in the form of the N-oxide;

or a pharmaceutically acceptable salt thereof.

2. The compound of claim 1 wherein not more than one of $X_1$, $X_3$, and $Y_1$ represents N.

3. The compound of claim 2 wherein $X_1$ or $Y_1$ represents N.

4. The compound of claim 2 wherein each of $X_1$, $X_2$, $X_3$, $Y_1$, $Y_2$ and $Y_3$ represents CH.

5. The compound of claim 1 wherein $X_3$ and $Y_1$ both represent N and each of $X_1$, $X_2$, $Y_2$ and $Y_3$ represents CH.

6. The compound of claim 1 wherein Ar$^1$ represents phenyl bearing 1 or 2 substituents selected from F, Cl, CN, C$_{1-4}$alkyl, hydroxymethyl, OH or C$_{1-4}$alkoxy.

7. The compound of claim 1 of formula II:

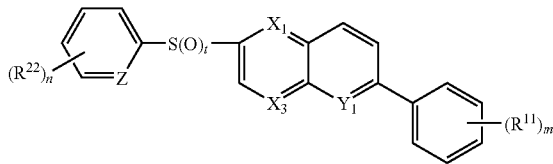

wherein:
m and n are independently 0, 1 or 2;
t is 2;
each of $X_1$, $X_3$, and $Y_1$ represents CH or N, provided that $X_1$ and $X_3$ do not both represent N and provided that $X_1$ and $Y_1$ do not both represent N;
Z represents CH or N, or when n is 1 or more Z may represent $CR^{22}$;
$R^{11}$ represents halogen, CN, $C_{1-4}$alkyl, hydroxymethyl, OH or $C_{1-4}$alkoxy;
$R_{22}$ represents halogen, CN, $R^a$, $OR^a$, $SR^a$, $SOR^a$, $SO_2R^a$, $SO_2NR^aR^b$, $NR^aR^b$, $CH_2NR^aR^b$, $COR^1$, $CO_2R^a$, $CH_2CO_2R^a$, $CONR^aR^b$, $CR^a=NOR^b$, $NR^aCOR^b$, $NR^aSO_2R^b$, $CH_2NR^aSOR^b$, $N=CHN(Me)_2$, $CH(OH)Ar^3$, $Ar^3$ or $CH_2Ar^3$; provided that when n is 2 at least one $R^{22}$ group is halogen or $C_{1-4}$alkyl;
or a pharmaceutically acceptable salt thereof.

8. The compound of claim 7 wherein n is 1 and $R^{22}$ is selected from CN, hydroxy$C_{1-6}$alkyl, 1-hydroxycyclobutyl, $C_{1-6}$alkylthio $C_{1-6}$alkylsulfinyl, $C_{1-6}$alkylsulfonyl, $C_{1-6}$alkylcarbonyl, formyl, $CONH_2$, $CO_2R^a$, $NR^aR^b$ or $Ar^3$.

9. A compound which is selected from the group consisting of:
2-(4-Fluorophenyl)-6-(phenylsulfonyl)naphthalene;
2-{[6-(2,4-Difluorophenyl)-2-naphthyl]sulfonyl}benzonitrile;
2-{[6-(2,4-Difluorophenyl)-2-naphthyl]sulfonyl}benzamide;
(1R,S)-1-(2-{[6-(2,4-Difluorophenyl)-2-naphthyl]sulfonyl}phenyl)ethanol;
(1R,S)-(2-{[6-(4-Fluorophenyl)-2-naphthyl]sulfonyl}phenyl)ethanol;
(1S)-1-(2-{[6-(2,4-Difluorophenyl)-2-naphthyl]sulfonyl}phenyl)ethanol;
(1R)-1-(2-{[6-(2,4-Difluorophenyl)-2-naphthyl]sulfonyl}phenyl)ethanol;
1-(2-{[6-(4-Fluorophenyl)-2-naphthyl]sulfonyl}phenyl)ethanone;
2-(2-{[6-(4-Fluorophenyl)-2-naphthyl]sulfonyl}phenyl)propan-2-ol;
(1S)-1-(2-{[6-(4-Fluorophenyl)-2-naphthyl]sulfonyl}phenyl)ethanol;
(1S)-1-(2-{[6-(4-Fluorophenyl)-2-naphthyl]sulfonyl}phenyl)ethanol;
(1R)-1-(2-{[6-(4-Fluorophenyl)-2-naphthyl]sulfonyl}phenyl)ethanol;
1-(2-{[6-(4-Fluorophenyl)-2-naphthyl]sulfonyl}pyridin-3-yl)ethanol;
2-{[6-(2,4-Difluorophenyl)-2-naphthyl]sulfonyl}benzaldehyde;
2-(4-Fluorophenyl)-6-{[2-(methylthio)phenyl]sulfonyl}naphthalene;
1-(2-{[6-(4-Fluorophenyl)-2-naphthyl]sulfonyl}phenyl)cyclobutanol;
2-(4-Fluorophenyl)-6-{[2-(methylsulfinyl)phenyl]sulfonyl}naphthalene;
2-(4-Fluorophenyl)-6-{[2-(methylsulfonyl)phenyl]sulfonyl}naphthalene;
(2-{[6-(2,4-Difluorophenyl)quinolin-2-yl]sulfonyl}phenyl)methanol;
(1S)-1-(2-{[4-(4-Fluorophenyl)quinolin-6-yl]sulfonyl}phenyl)ethanol;
(1R)-1-(2-{[6-(4-Fluorophenyl)-2-naphthyl]sulfonyl}pyridin-3-yl)ethanol;
(1S)-1-(2-{[6-(4-Fluorophenyl)-2-naphthyl]sulfonyl}pyridin-3-yl)ethanol;
(1S)-1-(2-{[7-(4-Fluorophenyl)quinolin-3-yl]sulfonyl}phenyl)ethanol;
Methyl 2-{[2-(4-fluorophenyl)quinolin-6-yl]sulfonyl}benzoate;
Methyl 2-{[2-(4-fluorophenyl)-1-oxidoquinolin-6-yl]sulfonyl}benzoate;
1-(2-{[2-(4-Fluorophenyl)quinolin-6-yl]sulfonyl}phenyl)ethanone;
(1S)-1-(2-{[7-(4-Fluorophenyl)-1,8-naphthyridin-3-yl]sulfonyl}phenyl)ethanol;
Methyl 2-{[7-(4-fluorophenyl)-1,8-naphthyridin-3-yl]sulfonyl}benzoate;
(1S)-1-(2-{[6-(2-Fluorophenyl)-2-naphthyl]sulfonyl}phenyl)ethanol;
6-{[6-(4-Fluorophenyl)-2-naphthyl]sulfonyl}-9H-purine;
2-(2-{[6-(4-Fluorophenyl)-2-naphthyl]sulfonyl}phenyl)pyrazine;
Methyl 2-{[6-(4-fluorophenyl)-2-naphthyl]sulfonyl}benzoate;
2-(2-{[6-(4-Fluorophenyl)-2-naphthyl]sulfonyl}phenyl)-1,3,4-oxadiazole;
(2-{[6-(4-Fluorophenyl)-2-naphthyl]sulfonyl}phenyl)(1H-imidazol-2-yl)methanol;
N-(2-{[6-(4-Fluorophenyl)-2-naphthyl]sulfonyl}phenyl)-N'-methylurea;
2-{[6-(4-Fluorophenyl)-2-naphthyl]sulfonyl}-1-methyl-1H-imidazole;
1-(2-{[6-(4-Fluorophenyl)-2-naphthyl]sulfonyl}benzyl)-1H-1,2,4-triazole;
(1S)-1-(2-{[6-(4-Fluorophenyl)-2-naphthyl]sulfonyl}-3-methylphenyl)ethanol;
N-[(2-{[6-(4-Fluorophenyl)-2-naphthyl]sulfonyl}pyridin-3-yl)methyl]-2-methylpropane-2-sulfinamide;
N'—(2-{[6-(4-Fluorophenyl)naphthalen-2-yl]sulfonyl}pyridin-3-yl)-N,N-dimethylimidoformamide;
(1E)-1-(2-{[6-(4-Fluorophenyl)naphthalen-2-yl]sulfonyl}phenyl)ethanone O-methyloxime;
(2-{[6-(4-Fluorophenyl)naphthalen-2-yl]sulfonyl}-3-thienyl)methanol;
(4-{[6-(4-Fluorophenyl)naphthalen-2-yl]sulfonyl}-3-thienyl)methanol;
1-(3-{[6-(4-Fluorophenyl)naphthalen-2-yl]sulfonyl}pyridin-4-yl)cyclobutanol;
4-{[6-(4-Fluorophenyl)-2-naphthyl]sulfonyl}-1H-benzimidazole;
(1S)-1-(2-{[6-(5-Fluoropyridin-2-yl)-2-naphthyl]sulfonyl}phenyl}ethanol;
1-(2-{[6-(4-Fluorophenyl)-2-naphthyl]sulfonyl}pyridin-3-yl)cyclobutanol;
2-{[6-(4-Fluorophenyl)-2-naphthyl]sulfonyl}pyridine;
2-{[6-(4-Fluorophenyl)-2-naphthyl]sulfonyl}pyridine 1-oxide;
1-(2-{[6-(4-Fluorophenyl)-2-naphthyl]sulfonyl}phenyl)-1H-imidazole; and
{5-Fluoro-2-[6-(phenylsulfonyl)-2-naphthyl]phenyl}methanol;
or a pharmaceutically acceptable salt thereof.

10. A pharmaceutical formulation comprising a compound of claim 1 or a pharmaceutically acceptable salt thereof and a pharmaceutically acceptable carrier.

* * * * *